US008518677B2

(12) United States Patent
Schmidt et al.

(10) Patent No.: US 8,518,677 B2
(45) Date of Patent: Aug. 27, 2013

(54) MICROBIAL BIOREACTION PROCESS

(75) Inventors: Hans Peter Schmidt, Holte (DK); Michael Katz, Malmö (SE); Bo Stenhuus, København ø (GB); Jochen Förster, Copenhagen V (GB)

(73) Assignee: Evolva Sa, Reinach (CH)

( * ) Notice: Subject to any disclaimer, the term of this patent is extended or adjusted under 35 U.S.C. 154(b) by 471 days.

(21) Appl. No.: 12/670,709

(22) PCT Filed: Jul. 25, 2008

(86) PCT No.: PCT/EP2008/059768
§ 371 (c)(1), (2), (4) Date: Jan. 26, 2010

(87) PCT Pub. No.: WO2009/016108
PCT Pub. Date: Feb. 5, 2009

(65) Prior Publication Data

US 2010/0203603 A1 Aug. 12, 2010

(30) Foreign Application Priority Data

Jul. 27, 2007 (GB) .................................. 0714671.5

(51) Int. Cl.
*C12P 7/22* (2006.01)
*C12N 1/21* (2006.01)

(52) U.S. Cl.
USPC .................................... 435/156; 435/252.33

(58) Field of Classification Search
USPC ............................................ 435/156, 252.33
See application file for complete search history.

(56) References Cited

U.S. PATENT DOCUMENTS

| | | | | |
|---|---|---|---|---|
| 4,865,973 | A | 9/1989 | Kollerup et al. | |
| 2004/0229326 | A1 | 11/2004 | Ben-Bassat et al. | |
| 2005/0208643 | A1 | 9/2005 | Schmidt-Dannert et al. | |
| 2009/0035839 | A1 | 2/2009 | Katz et al. | |
| 2009/0082286 | A1 | 3/2009 | Huang et al. | |
| 2011/0086399 | A1 * | 4/2011 | Smits et al. | 435/156 |

FOREIGN PATENT DOCUMENTS

| | | | |
|---|---|---|---|
| EP | 1715032 | | 10/2006 |
| WO | 0073485 | A1 | 12/2000 |
| WO | WO 200409234 | | 10/2004 |
| WO | 2005012507 | A1 | 2/2005 |
| WO | 2006089898 | A1 | 8/2006 |
| WO | 2006124999 | A2 | 11/2006 |
| WO | 2006125000 | A1 | 11/2006 |

OTHER PUBLICATIONS

Abe, et al., "Enzymatic formation of long-chain polyketide pyrones by plant type III polyketide synthases", *Phytochemistry*, vol. 65, pp. 2447-2453, 2004.

Cochrane, et al., "The Arabidopsis phenylalanine ammonia lyase gene family: kinetic characterization of the four PAL isoforms", *Phytochemistry*, vol. 65, pp. 1557-1564, 2004.

Ehlting, et al., "Three 4-coumarate:coenzyme A ligases in *Arabidopsis thaliana* represent two evolutionarily divergent classes in angiosperms", *The Plant Journal*, vol. 19, pp. 9-20, 1999.

Guerra, et al., "A novel system of genetic transformation allows multiple integrations of a desired gene in *Saccharomyces cerevisiae* chromosomes", *J Microbiol Methods*, vol. 67, pp. 437-445, 2006.

Hain, et al., "Disease resistance results from foreign phytoalexin expression in a novel plant", *Nature*, vol. 361, pp. 153-156, 1993.

Hamberger, et al., "The 4-coumarate:CoA ligase gene family in *Arabidopsis thaliana* comprises one rare, sinapate-activating and three commonly occurring isoenzymes", *Proc Natl Acad Sci U S A*, vol. 101, pp. 2209-2214, 2004.

Kaneko, et al., "A ligase from the Filamentous Bacteria *Streptomyces coelicolor* A3 (2)", *J. Bacteriology*, vol. 185, pp. 20-27, 2003.

Kyndt, et al., "Characterization of a bacterial tyrosine ammonia lyase, a biosynthetic enzyme for the photoactive yellow protein", *FEBS Lett*., vol. 512, pp. 240-244, 2002.

Martin, et al., "Engineering a mevalonate pathway in *Escherichia coli* for production of terpenoids", *Nature biotechnology*, vol. 21 pp. 796-802, 2003.

Mortta, et al., "Novel, polyketides synthesized with a higher plant stilbene synthase", *Eur. J. Biochem*, vol. 268, pp. 3759-3766, 2001.

Mumberg, et al., "Yeast vectors for the controlled expression of heterologous proteins in different genetic backgrounds", *Gene*, vol. 156, pp. 119-122, 1995.

Samappito, et al., "Aromatic and pyrone polyketides synthesized by a stilbene synthase from *Rheum tataricum", Phytochemistry*, vol. 62, pp. 313-323, 2003.

Sikorski, et al., "A System of Shuttle Vectors and Yeast Host for Efficient Manipulation of DNA in *Saccharomyces cerevisiae", Genetics*, vol. 122, pp. 19-27, 1989.

Stark, et al., "Novel Type of In Situ Extraction: Use of Solvent Containing Microcapsules for the Bioconversion of 2-Phenylethanol From $_L$-Phenylalanine by *Saccharomyces cerevisiae*", *Biotechnology and Bioengineering*, vol. 83(4), pp. 376-385, 2003.

Tilburn, et al., "Transformation by integration in *Aspergillus nidulans", Gene*, vol. 26, pp. 205-221, 1983.

Verduyn, et al., "Effect of Benzoic Acid on Metabolic Fluxes in Yeasts: A Continuous-Culture Study on the Regulation of Respiration and Alcoholic Fermentation", *Yeast*, vol. 8, pp. 501-517, 1992.

* cited by examiner

*Primary Examiner* — Chih-Min Kam

(74) *Attorney, Agent, or Firm* — McDonnell Boehnen Hulbert & Berghoff LLP

(57) ABSTRACT

A cis- or trans-stilbenoid of the general formula (1): in which each of $R^1$, $R^2$, $R^3$, $R^4$ and $R^5$ is hydrogen or hydroxy, or a glycosylated or oligomeric form thereof, is produced by cultivating a micro-organism producing said stilbenoid, in a multi-phase system comprising at least an aqueous first phase containing said micro-organism and a second phase immiscible with said aqueous phase in which (e.g. as which) said stilbenoid accumulates. The second phase may be said stilbenoid or a free or encapsulated solvent compatible with the growth of the micro-organism, for instance an ester.

(1)

OH, OH, $R^1$, $R^2$, $R^3$, $R^4$, $R^5$

7 Claims, 11 Drawing Sheets

Figurc 9

MICROBIAL BIOREACTION PROCESS

FIELD OF THE INVENTION

This invention relates generally to a bioreactor process in which a stilbenoid (i.e a hydroxystilbene) is produced using a two phase cultivation medium.

BACKGROUND OF THE INVENTION

There have recently been proposed recombinant micro-organisms that have the capacity to produce certain stilbenoids of the general formula 1:

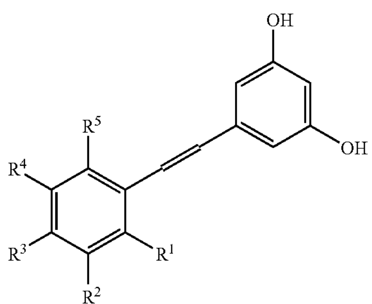

wherein each of $R^1$, $R^2$, $R^3$, $R^4$ and $R^5$ independently is hydrogen or hydroxy. Examples of such compounds include resveratrol (only $R^3$ being hydroxy) and pinosylvin (all of the R groups being hydrogen), see for instance WO2006/089898.

EP1181383 describes the in-situ extraction of a micro-organism fermentation product into an encapsulated organic solvent, the purpose being to prevent inhibition of production of the fermentation product caused by the product itself by sequestering it into the encapsulated solvent. This is therefore an approach to address the problem of a poor yield of the desired product.

U.S. Pat. No. 4,865,973 also tackles the problem of low metabolite yields due to product inhibition, this time by extraction of ethanol during cultivation of *Saccaromyces cerevisiae* yeast into a non-encapsulated solvent such as dodecylacetate.

US2004/0229326 again tackles the problem of product inhibition, this time in relation to aromatic compounds such as cinnamic acid, using a two phase extractive fermentation based on one or more of several defined solvents which include methyl decanoate.

Similarly, EP1715032 discloses a two phase fermentation using yeast to produce aroma compounds such as 2-phenylethanol with propylene glycol as extracting solvent to avoid product inhibition.

In fermentations to produce the stilbenoids with which the invention is concerned there is no problem relating to product inhibition however, as the existing strains of micro-organisms produce these compounds only in very small yields and it is not disclosed that they are secreted into the culture medium. Also, we have found that the solubility limit of the compounds is too low for product inhibition to become a problem.

Teachings such as WO2004/092344 describe biphasic reaction media for carrying out cell free enzymatic or other conversions, but this is of little relevance since there is no exposure of micro-organisms to the biphasic system.

SUMMARY OF THE INVENTION

Previously described micro-organisms have not been disclosed to release stilbenoids into the culture medium, as opposed to accumulating it within the micro-organism cells, although we have found that strains that we have described can do so. Also, a higher yield of stilbenoid compounds is desirable compared to that released into the culture medium by previously described micro-organisms. Strains of yeast and of other fungi or of bacteria which we have developed are such that the concentration of hydroxystilbene secreted into the medium by the micro-organisms is so high as to reach saturation, leading to precipitation of the product.

Accordingly, the invention provides in a first aspect a method for the production of a cis- or trans-stilbenoid of the general formula 1:

Formula 1

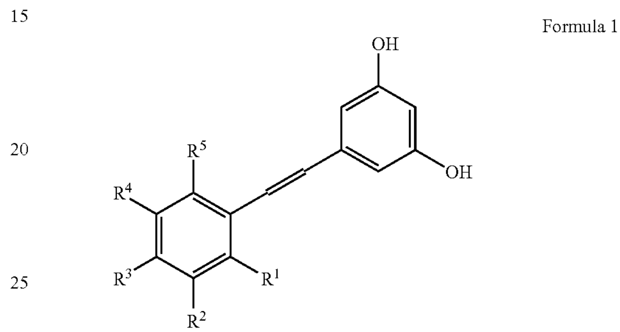

in which each of $R^1$, $R^2$, $R^3$, $R^4$ and $R^5$ independently is hydrogen or hydroxy, or a glycosylated or oligomeric form thereof, comprising cultivating a micro-organism producing said stilbenoid, wherein said cultivation is performed in a multi-phase system comprising at least an aqueous first phase containing said micro-organism and a second phase immiscible with said aqueous phase in which (e.g. as which) said stilbenoid accumulates.

The second phase in which the stilbenoid accumulates may be composed of the stilbenoid itself. The stilbenoid may then be recovered at least in part simply by separating the accumulated solids from the fermentation, normally followed by further purification steps.

However, the stilbenoid may also deposit onto vessel walls, stirrer shafts, sensor, baffles and other apparatus constituents. If it is desired to prevent this, the second phase may be a solvent for the stilbenoid which is compatible with the fermentation requirements of the micro-organism. This will prevent accumulating solids disturbing fermentation process control and down-stream processing, desirably preventing precipitation without reduction of the hydroxystilbene yield.

Preferably, one of said first and second phases is dispersed within the other and preferably the first (aqueous) phase is continuous and the second phase is dispersed.

Said stilbenoid may be resveratrol (only $R^3$=OH), pinosylvin (all R groups are hydrogen) or piceatannol (only $R^3$ and either $R^2$ or $R^4$ is OH). Preferably, not more than 3 of the R groups are hydroxy. Preferably, the stilbenoid is trans.

Said second phase is preferably a liquid. Optionally, said second phase is a micro-encapsulated liquid. Preferably, said liquid or micro-encapsulated liquid comprises or consists of an ester. Said ester is suitably of the general formula $R^6$—COO—$R^7$, and $R^6$ is H or an aliphatic straight or branched chain hydrocarbon moiety of from 1-6 carbon atoms and $R^7$ is an aliphatic straight or branched chain hydrocarbon moiety of from 2-16 carbon atoms, or a heteroatom containing hydrocarbon moiety of from 2 to 16 carbon atoms or an aromatic or heteroaromatic moiety of from 5 to 16 carbon atoms. $R^7$ may have from 3 to 9 carbon atoms. $R^6$ may have from 1 to 4 carbon atoms. Alternatively, $R^6$ may have from 6 to 12 carbon atoms and $R^7$ may have from 1 to 6 carbon atoms. For instance, the solvent may be methyl decanoate, propyl decanoate or butyl decanoate or the corresponding undecanoate or dodecanoate esters.

Preferably, said ester is an octyl acetate, especially n-octyl acetate.

Optionally, said liquid comprises or further comprises an alkane. It may consist of a said alkane and a said ester.

Said alkane may be a $C_6$ to $C_{16}$ straight or branched chain alkane, e.g. a $C_{9-14}$ alkane, e.g. a $C_{1-2}$ alkane. Preferably, said alkane is n-dodecane.

Preferably, said micro-organism, when cultivated in said aqueous phase without said immiscible phase, is capable of producing said stilbenoid in an amount sufficient to reach a saturated concentration thereof in said aqueous phase and to precipitate therefrom.

Methods according to the invention may further comprise separating said second phase and extracting said stilbenoid therefrom.

In a second aspect, the invention provides a method for producing an extraction solvent tolerant micro-organism strain producing a metabolite comprising:

(a) cultivating a starting micro-organism in a multi-phase system comprising at least an aqueous first phase containing said micro-organism and a second phase immiscible with said aqueous phase in which said metabolite accumulates, one of said first and second phases preferably being dispersed within the other, said second phase comprising a first solvent component to which the micro-organism is more tolerant and a first concentration of a second solvent component to which the micro-organism is less tolerant, (b) recovering progeny micro-organism from said cultivation (a), and (c) culturing said progeny micro-organism in a said multi-phase system in which the concentration of said second solvent component is increased above said first concentration.

In a further aspect, the invention provides A method for the production of a cis- or trans-stilbenoid of the general formula 1, comprising cultivating a micro-organism producing said stilbenoid, wherein said cultivation is conducted in a culture medium comprising or consisting of an aqueous phase and produces an amount of said stilbenoid (e.g. resveratrol) released from the micro-organisms into the culture medium which exceeds the solubility limit of said stilbenoid in said aqueous phase.

The method may be operated such that said stilbenoid precipitates from said culture medium. Alternatively, the cultivation is performed in a said culture medium which is a multi-phase system comprising at least said aqueous phase containing said micro-organism and a liquid solvent immiscible with said aqueous phase in which said stilbenoid accumulates.

Then it is optional whether said liquid solvent forms a liquid-liquid interface with said aqueous phase or is separated therefrom by encapsulation. Preferably, one of said aqueous phase and said liquid solvent is dispersed within the other and preferably the aqueous phase is continuous and said liquid solvent is dispersed therein.

All preferred features of the first aspect of the invention also apply in relation to the second aspect and this further aspect also.

DETAILED DESCRIPTION OF PREFERRED EMBODIMENTS

The micro-organisms used may be naturally occurring, or recombinant micro-organisms, or may be micro-organisms obtained by directed evolution from a starting naturally occurring or recombinant micro-organism. Repeated cultivation of micro-organism cells in a two phase system as described herein will generally produce evolved cells more suited to withstanding the conditions.

Micro-organisms that may be employed include fungi, including both filamentous fungi and yeasts, and bacteria. Yeasts are preferred, especially strains of *S. cerevisiae.*

The micro-organism may be one having an operative metabolic pathway comprising at least one enzyme activity, said pathway producing a said stilbenoid or an oligomeric or glycosidically-bound derivative thereof from a precursor aromatic acid of the general formula 2:

Formula 2

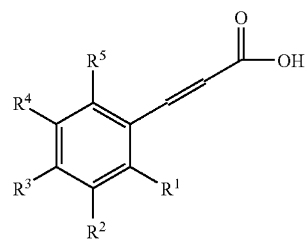

wherein each R group is as defined above.

For instance, the micro-organism may be one producing resveratrol from coumaric acid, producing pinosylvin from cinnamic acid, and/or producing piceatannol from caffeic acid.

The transformation of the said aromatic acid to the compound of Formula 1 may be by the action of an exogenous stilbene synthase expressed in said micro-organism, usually in conjunction with a suitable aromatic acid-CoA ligase serving to form the CoA thioester of the aromatic acid which together with malonyl-CoA acts as a substrate for the stilbene synthase.

Stilbene synthases are rather promiscuous enzymes that can accept a variety of physiological and non-physiological substrates. For instance, addition of various phenylpropanoid CoA starter esters led to formation of several products in vitro in Ikuro Abe et al., 2004 and Morita et al., 2001. Likewise it has been shown that resveratrol synthase from rhubarb (*Rheum tartaricum*) indeed synthesized a small amount of pinosylvin when cinnamoyl-CoA was used as substrate instead of coumaroyl-CoA (Samappito et al., 2003).

Micro-organisms producing resveratrol for use in the invention may be as described in WO2006/089898. In particular, the micro-organism may be one having an operative metabolic pathway comprising at least one enzyme activity, said pathway producing resveratrol, or an oligomeric or glycosidically-bound derivative thereof, from 4-coumaric acid.

Micro-organisms producing pinosylvin for use in the invention may be as described in WO2008/009728 and therefore may be one that has an operative metabolic pathway comprising at least one enzyme activity, said pathway producing pinosylvin, or an oligomeric or glycosidically-bound derivative thereof, from cinnamic acid.

Malonyl-CoA for said stilbenoid forming reaction may be produced endogenously.

The stilbene synthase may be expressed in said micro-organism from nucleic acid coding for said enzyme which is not native to the micro-organism and may be resveratrol synthase (EC 2.3.1.95) from a plant belonging to the genus of *Arachis*, a plant belonging to the genus of Rheum, or a plant belonging to the genus of *Vitus* or any one of the genera

*Artocarpus, Clintonia, Morus, Vaccinium, Pinus, Picea, Lilium, Eucalyptus, Parthenocissus, Cissus, Calochortus, Polygonum, Gnetum, Artocarpus, Nothofagus, Phoenix, Festuca, Carex, Veratrum, Bauhinia* or *Pterolobium* or may be a pinosylvin synthase (EC 2.3.1.146) from a plant belonging to the genus of *Pinus*, e.g. *P. sylvestris, P. strobes, P. densiflora, P. taeda*, a plant belonging to the genus *Picea*, or any one of the genus *Eucalyptus.*

For the preferential production of pinosylvin, the stilbene synthase may be one which exhibits a higher turnover rate with cinnamoyl-CoA as a substrate than it does with 4-coumaroyl-CoA as a substrate, e.g. by a factor of at least 1.5 or at least 2. Thus, in further preferred embodiments, said stilbene synthase is a pinosylvin synthase, suitably from a tree species such as a species of *Pinus, Eucalyptus, Picea* or *Maclura*. In particular, the stilbene synthase may be a pinosylvin synthase (EC 2.3.1.146) from a plant belonging to the genus of *Pinus*, e.g. *P. sylvestris, P. strobes, P. densiflora, P. taeda*, a plant belonging to the genus of *Picea*, or any one of the genus *Eucalyptus.*

The aromatic acid precursor may be produced in the micro-organism or may be supplied externally thereto, production by the micro-organism generally being preferred. Such aromatic acid precursors are generally producible in the micro-organism from a suitable amino acid precursor by the action of an enzyme such as a phenylalanine ammonia lyase or tyrosine ammonia lyase. The genes for the production of these enzymes may be recombinantly expressed in the micro-organism.

Thus, in certain preferred embodiments, said L-phenylalanine ammonia lyase is a L-phenylalanine ammonia lyase (EC 4.3.1.5) from a plant or a micro-organism. The plant may belong to the genus of *Arabidopsis*, e.g. *A. thaliana*, a plant belonging to the genus of *Brassica*, e.g. *B. napes, B. rapa*, a plant belonging to the genus of *Citrus*, e.g. *C. reticulata, C. clementines, C. limon*, a plant belonging to the genus of *Phaseolus*, e.g. *P. coccineus, P. vulgaris*, a plant belonging to the genus of *Pinus*, e.g. *P. banksiana, P. monticola, P. pinaster, P. sylvestris, P. taeda*, a plant belonging to the genus of *Populus*, e.g. *P. balsamifera, P. deltoides, P. Canadensis, P. kitakamiensis, P. tremuloides*, a plant belonging to the genus of *Solanum*, e.g. *S. tuberosum*, a plant belonging to the genus of *Prunus*, e.g. *P. avium, P. persica*, a plant belonging to the genus of *Vitus*, e.g. *Vitus vinifera*, a plant belonging to the genus of *Zea*, e.g. *Z. mays* or other plant genera e.g. *Agastache, Ananas, Asparagus, Bromheadia, Bambusa, Beta, Betula, Cucumis, Camellia, Capsicum, Cassia, Catharanthus, Cicer, Citrullus, Coffea, Cucurbita, Cynodon, Daucus, Dendrobium, Dianthus, Digitalis, Dioscorea, Eucalyptus, Gallus, Ginkgo, Glycine, Hordeum, Helianthus, Ipomoea, Lactuca, Lithospermum, Lotus, Lycopersicon, Medicago, Malus, Manihot, Medicago, Mesembryanthemum, Nicotiana, Olea, Oryza, Pisum, Persea, Petroselinum, Phalaenopsis, Phyllostachys, Physcomitrella, Picea, Pyrus, Quercus, Raphanus, Rehmannia, Rubus, Sorghum, Sphenostylis, Stellaria, Stylosanthes, Triticum, Trifolium, Triticum, Vaccinium, Vigna, Zinnia*. The micro-organism might be a fungus belonging to the genus *Agaricus*, e.g. *A. bisporus*, a fungus belonging to the genus *Aspergillus*, e.g. *A. oryzae, A. nidulans, A. fumigatus*, a fungus belonging to the genus *Ustilago*, e.g. *U. maydis*, a bacterium belonging to the genus *Rhodobacter*, e.g. *R. capsulatus*, a bacterium belonging to the genus *Streptomyces*, e.g. *S. maritimus*, a bacterium belonging to the genus *Photorhabdus*, e.g. *P. luminescens*, a yeast belonging to the genus *Rhodotorula*, e.g. *R. rubra.*

A suitable tyrosine ammonia lyase (EC 4.3.1.5) may be derived from yeast or bacteria. Suitably, the tyrosine ammonia lyase is from the yeast *Rhodotorula rubra* or from the bacterium *Rhodobacter capsulatus.*

Where the immediate product of the conversion of amino acid to aromatic acid is an aromatic acid that is not suitable as the immediate precursor of the desired stilbenoid, it may be converted to a more appropriate aromatic acid enzymatically by the micro-organism. For instance, cinnammic acid may be converted to coumaric acid by a cinnamate-4-hydroxylase (C4H). Thus, said 4-coumaric acid may be produced from trans-cinnamic acid by a cinnamate 4-hydroxylase, which preferably is expressed in said micro-organism from nucleic acid coding for said enzyme which is not native to the micro-organism.

In certain preferred embodiments, said cinnamate-4-hydroxylase is a cinnamate-4-hydroxylase (EC 1.14.13.11) from a plant or a micro-organism. The plant may belong to the genus of *Arabidopsis*, e.g. *A. thaliana*, a plant belonging to the genus of *Citrus*, e.g. *C. sinensis, C.×paradisi*, a plant belonging to the genus of *Phaseolus*, e.g. *P. vulgaris*, a plant belonging to the genus of *Pinus*, e.g. *P. taeda*, a plant belonging to the genus of *Populus*, e.g. *P. deltoides, P. tremuloides, P. trichocarpa*, a plant belonging to the genus of *Solanum*, e.g. *S. tuberosum*, a plant belonging to the genus of *Vitus*, e.g. *Vitus vinifera*, a plant belonging to the genus of *Zea*, e.g. *Z. mays*, or other plant genera e.g. *Ammi, Avicennia, Camellia, Camptotheca, Catharanthus, Glycine, Helianthus, Lotus, Mesembryanthemum, Physcomitrella, Ruta, Saccharum, Vigna*. The micro-organism might be a fungus belonging to the genus *Aspergillus*, e.g. *A. oryzae.*

The conversion of the aromatic acid precursor into its CoA derivative may be performed by a suitable endogenous or recombinantly expressed enzyme. Both cinnamoyl-CoA and coumaroyl-CoA may be formed in a reaction catalysed by an enzyme in which ATP and CoA are substrates and ADP is a product by a 4-coumarate-CoA ligase (also referred to as 4-coumaroyl-CoA ligase). Known 4-coumarate-CoA ligase enzymes accept either 4-coumaric acid or cinnamic acid as substrates and produce the corresponding CoA derivatives. Generally, such enzymes are known as '4-coumarate-CoA ligase' whether they show higher activity with 4-coumaric acid as substrate or with cinnamic acid as substrate. However, we refer here to enzymes having that substrate preference as 'cinnamate-CoA ligase' enzymes (or cinnamoyl-CoA-ligase). One such enzyme is described for instance in Aneko et al., 2003.

Said 4-coumarate-CoA ligase or cinnamate-CoA ligase may be a 4-coumarate-CoA ligase/cinnamate-CoA ligase (EC 6.2.1.12) from a plant, a micro-organism or a nematode. The plant may belong to the genus of *Abies*, e.g. *A. beshanzuensis, B. firma, B. holophylla*, a plant belonging to the genus of *Arabidopsis*, e.g. *A. thaliana*, a plant belonging to the genus of *Brassica*, e.g. *B. napes, B. rapa, B. oleracea*, a plant belonging to the genus of *Citrus*, e.g. *C. sinensis*, a plant belonging to the genus of *Larix*, e.g. *L. decidua, L. gmelinii, L. griffithiana, L. himalaica, L. kaempferi, L. laricina, L. mastersiana, L. occidentalis, L. potaninii, L. sibirica, L. speciosa*, a plant belonging to the genus of *Phaseolus*, e.g. *P. acutifolius, P. coccineus*, a plant belonging to the genus of *Pinus*, e.g. *P. armandii P. banksiana, P. pinaster*, a plant belonging to the genus of *Populus*, e.g. P. balsamifera, *P. tomentosa, P. tremuloides*, a plant belonging to the genus of *Solanum*, e.g. *S. tuberosum*, a plant belonging to the genus of *Vitus*, e.g. *Vitus vinifera*, a plant belonging to the genus of *Zea*, e.g. *Z. mays*, or other plant genera e.g. *Agastache, Amorpha, Cathaya, Cedrus, Crocus, Festuca, Glycine, Juglans, Keteleeria, Lithospermum, Lolium, Lotus, Lycopersicon, Malus, Medicago, Mesembryanthemum, Nicotiana, Nothot-*

*suga, Oryza, Pelargonium, Petroselinum, Physcomitrella, Picea, Prunus, Pseudolarix, Pseudotsuga, Rosa, Rubus, Ryza, Saccharum, Suaeda, Thellungiella, Triticum, Tsuga*. The micro-organism might be a filamentous fungi belonging to the genus *Aspergillus*, e.g. *A. flavus, A. nidulans, A. oryzae, A. fumigatus*, a filamentous fungus belonging to the genus *Neurospora*, e.g. *N. crassa*, a fungus belonging to the genus *Yarrowia*, e.g. *Y. lipolytica*, a fungus belonging to the genus of *Mycosphaerella*, e.g. *M. graminicola*, a bacterium belonging to the genus of *Mycobacterium*, e.g. *M. bovis, M. leprae, M. tuberculosis*, a bacterium belonging to the genus of *Neisseria*, e.g. *N. meningitidis*, a bacterium belonging to the genus of *Streptomyces*, e.g. *S. coelicolor*, a bacterium belonging to the genus of *Rhodobacter*, e.g. *R. capsulatus*, a nematode belonging to the genus *Ancylostoma*, e.g. *A. ceylanicum*, a nematode belonging to the genus *Caenorhabditis*, e.g. *C. elegans*, a nematode belonging to the genus *Haemonchus*, e.g. *H. contortus*, a nematode belonging to the genus *Lumbricus*, e.g. *L. rubellas*, a nematode belonging to the genus *Meilodogyne*, e.g. *M. hapla*, a nematode belonging to the genus *Strongyloidus*, e.g. *S. rattii, S. stercoralis*, a nematode belonging to the genus *Pristionchus*, e.g. *P. pacificus*.

Optionally, one may express, over express, or recombinantly express in said organism an NADPH:cytochrome P450 reductase (CPR). This may be a plant CPR. Alternatively, a native NADPH:cytochrome P450 reductase (CPR) may be overexpressed in said micro-organism. Optionally, said NADPH:cytochrome P450 reductase is a NADPH:cytochrome P450 reductase (EC 1.6.2.4) from a plant belonging to the genus of *Arabidopsis*, e.g. *A. thaliana*, a plant belonging to the genus of *Citrus*, e.g. *C. sinensis, C.×paradisi*, a plant belonging to the genus of *Phaseolus*, e.g. *P. vulgaris*, a plant belonging to the genus of *Pinus*, e.g. *P. taeda*, a plant belonging to the genus of *Populus*, e.g. *P. deltoides, P. tremuloides, P. trichocarpa*, a plant belonging to the genus of *Solanum*, e.g. *S. tuberosum*, a plant belonging to the genus of *Vitus*, e.g. *Vitus vinifera*, a plant belonging to the genus of *Zea*, e.g. *Z. mays*, or other plant genera e.g. *Ammi, Avicennia, Camellia, Camptotheca, Catharanthus, Glycine, Helianthus, Lotus, Mesembryanthemum, Physcomitrella, Ruta, Saccharum, Vigna*.

Because, as described above, for the production of pinosylvin, production of cinnamic acid by a PAL enzyme and also its conversion on to pinosylvin is preferred to either the production of coumaric acid from tyrosine by a substrate promiscuous PAL or by conversion of cinnamic acid by a C4H enzyme, micro-organisms for use in the invention to produce pinosylvin preferably have a PAL which favours phenylalanine as a substrate (thus producing cinnamic acid) over tyrosine (from which it would produce coumaric acid). Preferably, therefore, the ratio $K_m$(phenylalanine)/$K_m$(tyrosine) for the PAL is less than 1:1, preferably less 1:5, e.g. less than 1:10. As usual, $K_m$ is the molar concentration of the substrate (phenylalanine or tyrosine respectively) that produces half the maximal rate of product formation ($V_{max}$).

Except where micro-encapsulation is used, in choosing a solvent to act as the water immiscible phase in the cultivation, there generally will be some tension between opposing requirements for a solvent that does not hamper the growth of the micro-organism and one that successfully extracts the hydroxystilbene product. Generally, the less miscible with water is the solvent, the less it will interfere with the micro-organism growth, but the less effective it will be in extracting the hydroxystilbene.

The rate at which the system is agitated will also have an effect, greater agitation tending to increase the interference of the solvent with the growth of the micro-organism. The toxicity of the water immiscible material for the micro-organism may therefore be regarded as being divided into a direct toxic effect due to the concentration of the immiscible solvent in the aqueous medium and a phase toxicity due to the physical presence of the immiscible phase which can exert effects by nutrient extraction, limited access to nutrients due to emulsion formation, cell coating, attraction to the interface and, the most detrimental effect, disruption of cell membranes.

The rate of agitation employed should therefore be balanced against the nature of the immiscible solvent material.

However, optionally, the solvent is physically separated from the aqueous phase by micro-encapsulation, as described in Stark et al, 2003 and EP1181383 using for instance solvent filled alginate micro-spheres of for instance 1-4 mm diameter. The encapsulating material is chosen to be permeable to the stilbenoid. This can prevent phase toxicity, although the aqueous phase may remain saturated with the solvent. This allows a more free choice of solvent on the basis of its extractive power for the stilbenoid having regard to the stilbenoid solubility therein and its partition coefficient for the stilbenoid.

The solvent is preferably one in which the micro-organism of interest, if necessary after adaptation as described in Example 12, is able to grow in an aqueous phase culture medium in liquid-liquid interface contact with the said solvent at a growth rate of at least 50% of the growth rate obtainable in the aqueous phase culture medium without the solvent being present. Such a solvent may be referred to as a biocompatible solvent.

Preferred solvents have a partition coefficient logP between water and octanol of not more than 4.4, preferably not more than 4.0. Such solvents are generally suitable for all of the stilbenoids. However, for the most hydrophobic stilbenoids, especially pinosylvin, a logP value of up to 7.5 may be used, e.g. up to 6.5.

Having regard particularly for their extraction affinity for more polar hydroxy stilbenes, preferred solvents are esters, especially esters of the general formula $R^6$—COO—$R^7$, where $R^6$ is H or an optionally substituted aliphatic straight or branched chain hydrocarbon moiety of from 1-6 carbon atoms, or an optionally substituted aromatic or heteroaromatic moiety of from 5 to 6 carbon atoms, and $R^7$ is an optionally substituted aliphatic straight or branched chain hydrocarbon moiety of from 2-16 carbon atoms, or an optionally substituted heteroatom containing hydrocarbon moiety of from 2 to 16 carbon atoms or an optionally substituted aromatic or heteroaromatic moiety of from 5 to 16 carbon atoms. Suitably, $R^7$ has from 3 to 9 carbon atoms. Suitably the ester is formed between a short chain acid and a long chain alcohol, e.g. where $R^6$ has from 1 to 4 carbon atoms and $R^7$ has from 6 to 12 carbon atoms.

Said ester is preferably an octyl acetate, e.g. n-octyl acetate (logP=3.7). Alternatives include hexyl, heptyl, nonyl (logP=4.2) and decyl acetates, and the corresponding formates and propionates.

Alternatively, esters formed between long chain acids and short chain alcohols may be used, e.g. where $R^6$ may have from 6 to 12 carbon atoms and $R^7$ may have from 1 to 6 carbon atoms. For instance, the solvent may be methyl decanoate (logP=4.3), propyl decanoate or butyl decanoate or the corresponding undecanoate or dodecanoate esters.

Also, long chain ketones such as a $C_8$ to $C_{12}$ ketones, e.g. undecanone may be used. These may be of the formula $R^8COR^9$ where $R^8$ and $R^9$ independently may be an optionally substituted aliphatic straight or branched chain hydrocarbon moiety, e.g. where $R^8$ is $C_{1-5}$, more preferably $C_{1-3}$, and $R^9$ is $C_{7-12}$.

Other suitable solvents may be as described in U.S. Pat. No. 4,865,973. Except where these overlap with those described above however they are in general less preferred. They include double bond unsaturated aliphatic alcohols having 12 or more carbon atoms, saturated branched chain aliphatic alcohols having 14 or more carbon atoms or mixtures thereof (e.g. guerbet alcohols), double bond unsaturated aliphatic acids having 12 or more carbon atoms, aliphatic and aromatic mono- di- or tri-esters having 12 or more carbon atoms, aliphatic noncyclic ketones and aliphatic aldehydes having 12 or more carbon atoms.

Examples include:

oleyl alcohol, (cis-9-octadecen-1-ol), phytol (3,7,11,15-tetramethyl-2-hexadecen-1-ol), isophytol (3,7,11,15-tetramethyl-1-hexadecen-3-ol), isostearyl alcohol e.g. the commercial product sold under the trademark ADOL 66, isocetyl alcohol e.g. the commercial product sold under the trademark Eutanol G-16, octyl dodecanol e.g. the commercial product sold under the trademark Eutanol G, oleic acid (cis-9-octadecenoic acid), linoleic acid, (9,11-octadecadienoic acid), ricinoleic acid, (12-hydroxy-9-octadecenoic acid), dodecyl acetate ($CH_3$ $COO(CH_2)_{11}$), butyl dodecanoate, ($CH_3$ $(CH_2)_{10}$ $COOC_4H_9$), dibutyl sebacate ($C_4H_9$ $OOC(CH_2)_8$ $H_{17}COOC_4H_9$, di (2-ethylhexyl)sebacate, ($C_8H_{17}OOC$ $(CH_2)_8$ $COOC_8H_{17}$), dibutyl adipate ($C_4H_9$ $OOC(CH_2)_4$ $COOC_4H_9$), di(2-ethylhexyl)adipate, ($C_8H_{17}$ $OOC(CH_2)_4$ $COOC_8H_{17}$), di(2-ethylhexyl)phthalate, ($C_8H_{17}OOCC_6H_4COOC_8H_{17}$), di(3,5,5-trimethyhexyl), phthalate ($C_8H_{17}OOCC_6H_4COOC_8H_{17}$), glyceroltrideca-([$CH_3$ $(CH_2)_8COOCH_2]_2$ $CHOCO(CH_2)_8CH_3$)noate, 2-dodecanone ($CH_3CO(CH_2)_9CH_3$), dodecanal ($CH_3(CH_2)$ 10 CHO). the commercial product sold under the trademark ADOL 85 NF (69 percent oleyl alcohol), the commercial product sold under the trademark ADOL 330 (62 percent oleyl alcohol), and the commercial product sold under the trademark HD oleyl alcohol (commercial oleyl alcohol).

Generally, all the solvents described above may be used in any admixture with one or more others.

For the production of pinosylvin, which is the least polar of the hydroxystilbenes of formula 1, an alkane may be used. This may be a $C_6$ to $C_{16}$ (e.g. $C_9$ to $C_{14}$) straight or branched chain alkane such as a nonane, decane, undecane, dodecane or higher, e.g. n-dodecane. However, used by itself, n-dodecane does not have sufficient polarity to be a good extractant for resveratrol and more hydroxylated compounds.

On the other hand, the esters are less well tolerated by certain micro-organisms as regards toxicity and in some cases can steer hydroxystilbene production towards resveratrol and away from pinosylvin.

For the mixed production of resveratrol and pinosylvin for instance, it is therefore preferred to use a mixture of a said ester and a said alkane, e.g. octyl acetate and n-dodecane.

Micro-organisms that do not fully tolerate a particular solvent such as octyl acetate may be evolved to do so by methods described briefly above.

In the present context the term "micro-organism" relates to microscopic organisms, including bacteria, microscopic fungi, including yeast. More specifically, the micro-organism may be a fungus, and more specifically a filamentous fungus belonging to the genus of *Aspergillus*, e.g. *A. niger, A. awamori, A. oryzae, A. nidulans*, a yeast belonging to the genus of *Saccharomyces*, e.g. *S. cerevisiae, S. kluyveri, S. bayanus, S. exiguus, S. sevazzi, S. uvarum*, a yeast belonging to the genus *Kluyveromyces*, e.g. *K. lactis K. marxianus* var. *marxianus, K. thermotolerans*, a yeast belonging to the genus *Candida*, e.g. *C. utilis C. tropicalis, C. albicans, C. lipolytica, C. versatilis*, a yeast belonging to the genus *Pichia*, e.g. *P. stipidis, P. pastoris, P. sorbitophila*, or other yeast genera, e.g. *Cryptococcus, Debaromyces, Hansenula, Pichia, Yarrowia, Zygosaccharomyces* or *Schizosaccharomyces*. Concerning other micro-organisms a non-exhaustive list of suitable filamentous fungi is: a species belonging to the genus *Penicillium, Rhizopus, Fusarium, Fusidium, Gibberella, Mucor, Mortierella*, and *Trichoderma*.

Concerning bacteria a non-exhaustive list of suitable bacteria is follows: a species belonging to the genus *Bacillus*, a species belonging to the genus *Escherichia*, a species belonging to the genus *Lactobacillus*, a species belonging to the genus *Lactococcus*, a species belonging to the genus *Corynebacterium*, a species belonging to the genus *Acetobacter*, a species belonging to the genus *Acinetobacter*, a species belonging to the genus *Pseudomonas*, etc.

The preferred micro-organisms of the invention may be *S. cerevisiae, A. niger, A. nidulans, A. oryzae, E. coli, L. lactis* or *B. subtilis*.

The constructed and engineered micro-organism can be cultivated using commonly known processes, including chemostat, batch, fed-batch cultivations, etc.

Stilbenoids produced as described herein may optionally be isolated or purified and suitable methods include solvent extraction with n-hexane, followed by sequential extraction with 100% ether, acetone, methanol and water, and chromatographic purification on a silicagel column using a n-hexane/ethyl acetate (2/1) system.

The micro-organism may be fed with a carbon substrate which is optionally selected from the group of fermentable carbon substrates consisting of monosaccharides, oligosaccharides and polysaccharides, e.g. glucose, fructose, galactose, xylose, arabinose, mannose, sucrose, lactose, erythrose, threose, and/or ribose. Said carbon substrate may additionally or alternatively be selected from the group of non-fermentable carbon substrates including ethanol, acetate, glycerol, and/or lactate. Said non-fermentable carbon substrate may additionally or alternatively be selected from the group of amino acids and may be phenylalanine and/or tyrosine.

BRIEF DESCRIPTION OF THE DRAWINGS

To assist in the ready understanding of the above description of the invention reference has been made to the accompanying drawings in which are shown.

EXAMPLES

Example 1

Figure 1A:
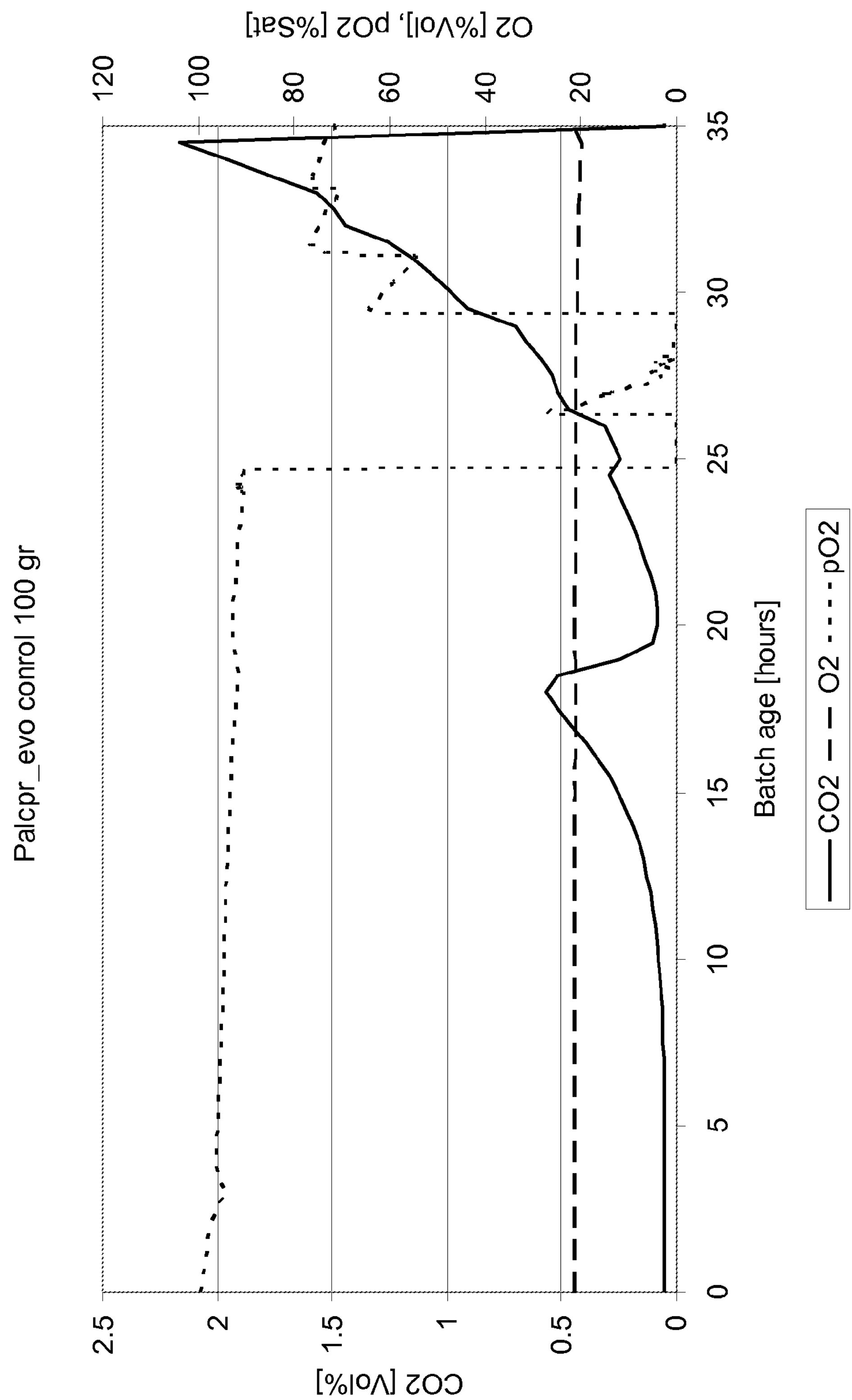
FIG. 1A: Fermentation profile for PALCPR-control (see Example 3): $CO_2$-evolution (CO2 Vol %), $O_2$ consumption ($O_2$ Vol %) and dissolved oxygen ($PO_2$% Sat) are shown.

Expression of the PAL-pathway to Resveratrol in *S. cerevisiae* Strain Overexpressing Native *S. cerevisiae* NADP-cytochrome P450 Reductase (CPR)

A yeast strain FSSC-PAL2C4H4CL2VST1-pADH1CPR1 was used. This is a strain of *S. cerevisiae* having introduced therein genes expressing PAL2 from *A. thaliana*, C4H from *A. thaliana*, 4CL2 from *A. thaliana*, and VST1 from *Vitis vinifera* with overexpressed CPR from *A. thaliana* (see WO2006/089898 and WO2008/009728 for details). In summary construction of the strain is described further below and is divided in parts A, B, C, D and E.

A: Construction of a Strain Overexpressing Native *S. cerevisiae* NADP-cytochrome P450 Reductase (CPR).

The native promoter of *S. cerevisiae* NADP-cytochrome P450 reductase CPR1 gene (encoded by YHR042W) was replaced with the constitutive *S. cerevisiae* alcohol dehydrogenase ADH1 promoter via chromosomal promoter exchange using the “bi-partite” PCR-based allele replacement method. Primers A and B were used to generate fragment CPR1-UP (Table 1) via PCR at a melting temperature of 56° C. using *S. cerevisiae* genomic DNA as template. Primers C and D were then used to generate fragment CPR1-S via PCR at a melting temperature of 56° C. using *S. cerevisiae* genomic DNA as template. Fragments AD1 (klURA 3' end fused to promoter ADH1) and AD2 (promoter ADH1 fused to KlURA 5' end) were generated via PCR using primers AD-fw and Int3' and IntS' and AD-rv at a melting temperature of 56° C. and 56° C., respectively. Plasmid pWAD1 was used as template for generation of fragment AD1 and plasmid pWAD2 was used for generating fragment AD2.

Fragments CPR_UP were then fused to fragment AD2 using fusion PCR with primers A and Int3' at a melting temperature of 56° C. resulting in fusion fragment 1 (bi-partite substrate 1). A second fusion PCR was used to fuse fragments AD1 and CPR-S with IntS' and primer D at a melting temperature of 56° C. resulting in fusion fragment 2 (bi-partite substrate 2).

Fusion fragments 1 and 2 (bi-partite substrates 1 and 2) were purified on agarose gel and used for co-transformation of *S. cerevisiae* strain FS01528 (Mata, ura3 his 3) and the transformants were plated on SC-URA plates and incubated for 2-4 days at 30° C. Transformants were streak purified on SC-ura plates and incubated another 2 days at 30° C. and then plated onto 5-FOA (5-fluoroorotic acid) plates. After incubation for 2 days at 30° C. “pop-out” colonies appeared, which were streak purified on a new 5-FOA-plate and incubated another 2 days at 30° C. and then finally transferred to a rich medium plate YPD. The resulting colonies were analyzed for the presence of fragment of size 1700-1800 base pairs using yeast colony PCR with primers A and AD-rev and a melting temperature at 55° C. and an elongation time of 1 minute and 45 seconds. One of the positive colonies from the colony PCR containing the new replaced ADH1 promoter in front of the CPR1 gene was named FSpADH1-CPR (Mata ura3 his3 pADH1-CPR1) strain.

TABLE 1

Primers and fragments used in the “bi-partite” PCR-based allele replacement method to exchange native *S. cerevisie* CPR1 promoter with *S. cerevisiae* ADH1 promoter

| Primers |
|---|
| A 5'-GTATTCTATATCCACGCCTGCAAAC 3' *[1] |
| B 5'-AGTACATACAGGGAACGTCCCTACAGGAACGCAAACTTAAGCTAC 3' *[2] |
| C 5'-GCATACAATCAACTATCTCATATACAATGCCGTTTGGAATAGACAACACC 3' *[3] |
| D 5'-GCTTCCGCATTACAAATAAAGTCTTCAA 3' *[4] |
| AD-fw 5'-GGACGTTCCCTGTATGTACTAGGGGGATCGAAGAAATGATGG 3' *[5] |
| Int3' 5'-GAGCAATGAACCCAATAACGAAATC 3' *[6] |
| Int5' 5'-CTTGACGTTCGTTCGACTGATGAGC 3' *[7] |
| AD-rv 5'-TGTATATGAGATAGTTGATTGTATGC 3' *[8] |
| **Fragments** |
| CPR-UP generated from primers A and B (CPR1 gene fragment upstream of start codon (ATG)) |
| CPR-S generated from primers C and D (CPR1 gene fragment containing start codon (ATG)) |
| AD1 (ADH1 promoter coupled to two thirds of *K.lactis* URA3 towards the 5' end generated from primers AD-fw and Int3') |
| AD2 (Two thirds of *K.lactis* URA3 towards the 3' end coupled to the ADH1 promoter. Generated from primers Int5' and AD-rv) |
| Fusion fragment 1 (CPR-UP fragment fused to AD2 fragment) |
| Fusion fragment 2 (AD1 fragment fused to CPR-S fragment) |

*[1] SEQ ID NO: 1
*[2] SEQ ID NO: 2
*[3] SEQ ID NO: 3
*[4] SEQ ID NO: 4
*[5] SEQ ID NO: 5
*[6] SEQ ID NO: 6
*[7] SEQ ID NO: 7
*[8] SEQ ID NO: 8

B: Isolation of Genes Encoding PAL, C4H, 4CL, and VST1

Phenylalanine ammonia lyase (PAL2), cinnamate 4-hydroxylase (C4H), 4-coumarate:CoenzymeA ligase (4CL1) were isolated as described previously (WO2006/089898) via PCR from *A. thaliana* cDNA (BioCat, Heidelberg, Germany).

4-coumarate:CoenzymeA ligase (4CL2) (see WO2006/089898 and PCT/EP2007/057484 for details) was isolated via PCR from *A. thaliana* cDNA (BioCat, Heidelberg, Germany) using the forward primer 5'-GCGAATTCTTATGACGACACAAGATGTGATAGTCAATGAT-3' SEQ ID NO: 9 containing an EcoR1 restriction site and reverse primer 5'-GCACTAGTATCCTAGTTCATTAATCCATTTGCTAGT-CTTGCT-3' SEQ ID NO:10 containing a Spe1 restriction site.

The VST1 gene encoding *Vitis vinifera* (grapevine) resveratrol synthase (Hain et al, 1993) was synthesized by GenScript Corporation (Piscataway, N.J.). The amino acid sequence (see WO2006/089898 and WO2008/009728 for details) was used as template to generate a synthetic gene optimized for expression in *S. cerevisiae*. The synthetic VST1 gene was delivered inserted in *E. coli* pUC57 vector flanked by BamH1 and Xho1 restriction sites. The synthetic gene was purified from the pUC57 vector by BamH1/Xho1 restriction and purified from agarose gel using the QiaQuick Gel Extraction Kit (Qiagen).

C: Construction of a Yeast Vector for Expression of PAL and C4H

Plasmid, pESC-URA-PAL-C4H, containing the genes encoding PAL and C4H under the control of the divergent GAL1/GAL10 promoter was constructed as described in Example 3 of WO2006/089898.

D: Construction of a Yeast Vector for Expression of 4CL

The gene encoding 4CL1 and 4CL2 were isolated as described in previously. The amplified 4CL1 PCR-product was digested with Xba1/BamH1 and ligated into Spe1/BglII digested pESC-TRP vector (Stratagene), resulting in vector pESC-TRP-4CL. The amplified 4CL2 PCR-product was digested with EcoR1/Spe1 and ligated into EcoR1/Spe1 digested pESC-HIS vector (Stratagene), resulting in vector pESC-HIS-4CL2. Two different clones of pESC-TRP-4CL1 and pESC-HIS-4CL2 were sequenced to verify the sequence of the cloned gene.

E: Construction of Yeast Vectors for Expression of 4CL and VST

The gene encoding VST from *Vitis vinifera* (grape) was isolated as described previously. The purified BamH1/Xho1 digested VST gene fragment was ligated into BamH1/Xho1 digested pESC-HIS-4CL2 plasmid or pESC-trp-4CL1 plasmid (example 15). The resulting plasmids, pESC-HIS-4CL2-VST and pESC-TRP-4CL1-VST contained the genes encoding 4CL1, 4CL2 and VST under the control of the divergent GAL1/GAL10 promoter. The sequence of the gene encoding VST was verified by sequencing of two different clones of pESC-HIS-4CL2-VST and pESC-TRP-4CL1-VST.

FSpADH1-CPR (Mata ura3 his3 pADH1-CPR1) as described previously was co-transformed with the vectors pESC-URA-PAL-C4H and pESC-HIS-4CL2-VST, resulting in the strain FSSC-PALC4H$_4$CL2VST-pADH1CPR1 (Mata ura3 his3 pADH1-CPR1, pESC-URA-PAL-C4H, pESC-HIS-4CL2-VST).

Example 2

Adaptation of Strain PALCPR to the Presence of Solvents

Figure 5A:
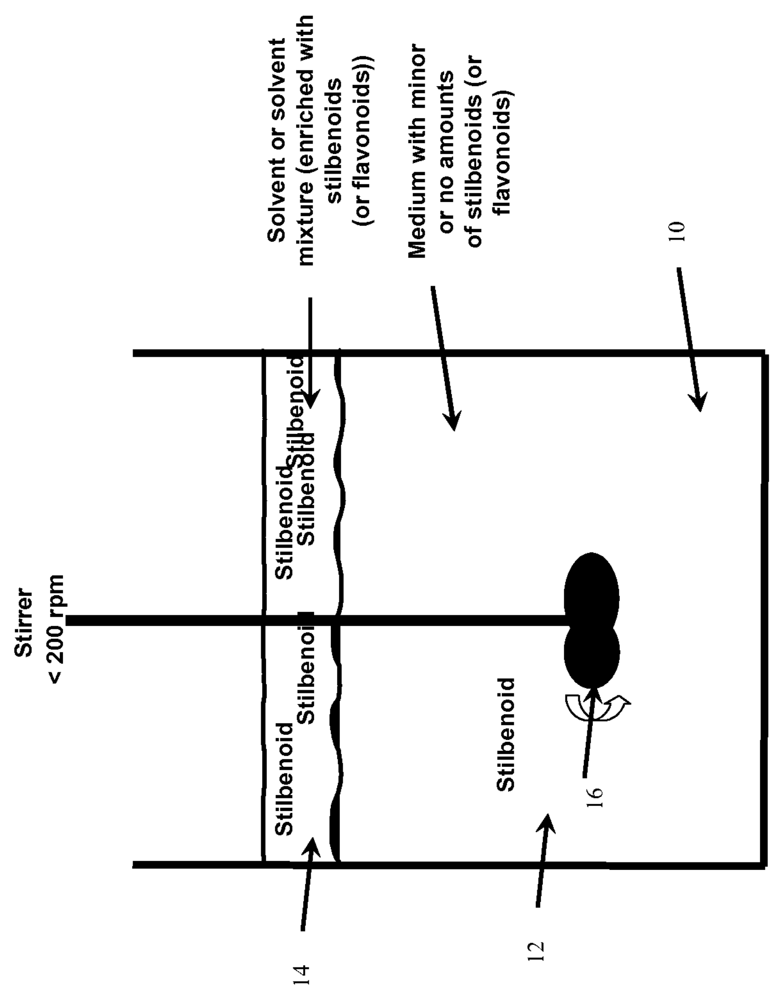
FIG. 5: Principle of two-phase fermentation. A: extraction of stilbenoids into solvent phase with low stirring and hence physical separate phases; B: extraction of stilbenoids into solvent phase with high stirring and hence with mixed phases.
Figure 5B:
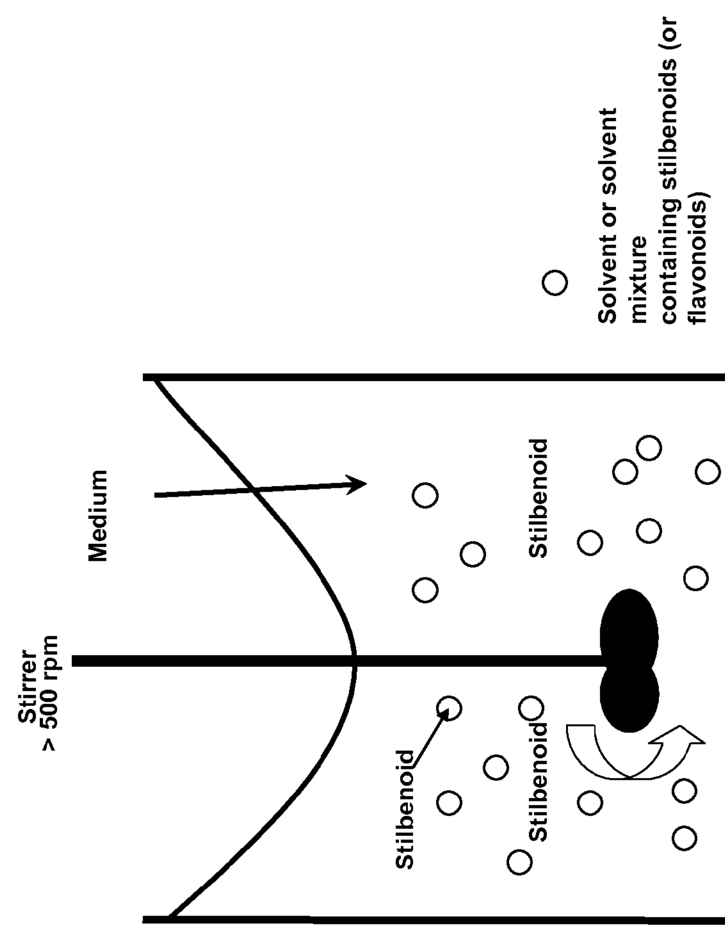
Figure 6:
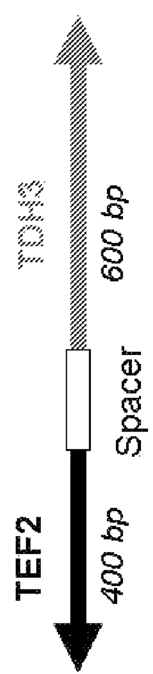
FIG. 6: Structure of the fused divergent TEF1-TDH3 promoters referred to in Example 9.
Figure 7:
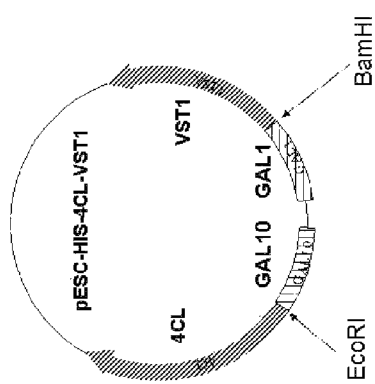
FIG. 7: Structure of a plasmid vector pESC-HIS-4CL-VST1 containing galactose inducible promotors Gal1/Gal10 referred to in Example 9 (VII).
Figure 8:
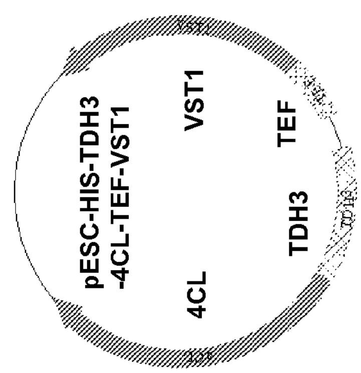
FIG. 8: Structure of a plasmid vector pESC-HIS-TDH3-4CL-TEF-VST1 referred to in Example 9(VII).

Yeast strain FSSC-PAL2C4H4CL2VST1-pADH1CPR1 as described in the previous example was subjected to a train of batch fermentations in a fermentor from Applikon containing defined medium according to Verduyn et al. (1992), containing: 10.0 g/L $(NH_4)_2SO_4$; 3.0 g/L $KH_2PO_4$; 0.5 g/L $MgSO_4$.7H2O; trace metals and vitamins with the aim of adapting it to the presence of solvents. The working volume was 1 L and the gas flowrate was set at 1.5 l/m, temperature was uncontrolled and pH was set at 5.5. The first fermentation contained 10 g/l glucose and 50 g/l galactose, and stirring rate was kept low to prevent mixing of the medium- and solvent phase, as illustrated in FIG. 5A in which is seen a fermentor vessel 10 containing the two separated phases 12 (aqueous) and 14 (solvent) agitated by a stirrer 16 at below 200 rpm. After consumption of the glucose and at the onset of galactose consumption, a mixture of 10 ml octylacetate and 40 ml dodecane was added. Consumption of galactose continued and the strain was harvested and used for a next fermentation. The next fermentation was performed with said harvested strain using similar fermentation conditions as to the previous one, but now with addition of a mixture of 50 ml octylacetate and 100 ml dodecane. Indeed the cells were able to grow in the presence of said solvent mixture, and the strain was harvested and used for a next fermentation. The next fermentation was performed with said harvested strain, using similar conditions as to the previous one, but now the stirring rate was increased to 1000 rpm halfway through the consumption of galactose, causing mixing of the solvent phase with the medium phase as illustrated in FIG. 5B. Indeed the cells remained able to grow when the phases were mixed and the strain was harvested and used for a next fermentation. The next fermentation was performed with said harvested strain using similar conditions as to the previous one, but now with addition of a mixture of 100 ml octylacetate and 100 ml dodecane. The increase of the octylacetate to 100 ml caused the arrest of cell growth, indicated by a halt in galactose consumption, and therefore the amount of dodecane was increased to 200 ml, in order to further obscure the toxic effect of octylacetate. Indeed the cells were now able to grow in the presence of said solvent mixture at high stirring rate. The strain was harvested and stored in 15% glycerol at −80° C.

Example 3

Determination of Intracellular and Extracellular Levels of Stilbenoids in a Batch Culture of Strain PALCPR The last harvested strain as described in previous example was grown in two independent batch cultures with a working volume of 1 liter, containing defined medium according to Verduyn et al. (1992), containing: 10.0 g/L $(NH_4)_2SO_4$; 3.0 g/L $KH_2PO_4$; 0.5 g/L $MgSO_4.7H_2O$; trace metals and vitamins and 10 g/l glucose and 100 g/l galactose as the carbon sources. Antifoam (300 μl/L, Sigma A-8436) was added to avoid foaming. The carbon source was autoclaved separately from the mineral medium and afterwards added to the fermentor. In addition, the vitamin and trace metal solutions were added to the fermentor by sterile filtration following autoclaving and cooling of the medium. The fermentor system was from Sartorius BBI systems and consisted of a baffled 3-liter reactor vessel with 1 liter working volume equipped with Biostat B Plus controller. The reactor vessel was equipped with one lower-fitted Rushton turbine which was rotating eventually at 1000 rpm, the temperature was kept at 30±1° C., and the pH was kept at 5.5±0.2 by automatic addition of 2M KOH. The gasflow was controlled by a mass flow controller and was set to 1.5 vvm (1.5 l/min). The off-gas was led through a cooled condenser, and was analyzed for $O_2$ and $CO_2$ (Model 1308, Innova, Denmark). The initial batch cultures were started by inoculation of the medium with a pre-grown strain that was harvested in the exponential phase and stored at −80° C. in 15% glycerol. The cells were allowed to fully consume the glucose at a stirring speed of 1000 rpm, and the average dissolved oxygen content was kept above 70% of saturated air. After approximately 20 hrs, at the onset of galactose consumption, the stirring rate was turned down to 300 rpm, and to one culture a mixture of 200 ml dodecane and 100 ml of octylacetate was slowly added. This cultivation will further be referred to as PALCPR-solvent, whereas the cultivation without addition of solvent will be referred to as PALCPR-control.

Upon addition of the solvent mixture to the PALCPR-solvent culture the $CO_2$ production halted temporarily, but recovered again after 5 minutes. Moreover, the $CO_2$-production in the PALCPR-control culture also ceased temporarily and recovered soon, indicating that this was more the result of the hampered oxygen transfer imposed by the lowered stirrer speed. The stirrer speed was increased in steps of 100 rpm to 1000 rpm over a period of 5 hours. In order to enable comparison of production of stilbenoids in both cultures, the PALCPR-control culture was subjected to the same conditioning regime. In both cultures the cells kept growing exponentially with concomitant production of $CO_2$.

gradient of acetonitrile and milliq water (both containing 50 ppm trifluoroacetic acid) was used at a flow of 0.4 ml/min. The gradient profile was linear from 15% acetonitrile to 100% acetonitrile over 20 min. The elution time was approximately and 5.0-5.2 minutes for resveratrol and 8.8-8.9 minutes for trans-pinosylvin.

The total concentration of stilbenoid intermediates that was produced was then calculated by multiplying the concentrations in the upper phase with a factor of 0.3 and then adding them to the concentrations that were observed in the lower phase. For the PALCPR-control culture, two aliquots of 10 ml of cell broth were collected, and one aliquot was vigorously mixed with 10 ml of 100% of ethanol. The solubility of stilbenoids in ethanol is far higher than in water and thus ensures the determination of levels of stilbenoids that would normally exceed the aqueous solubility. Furthermore, stilbenoids that possibly would be bound to the cell-membranes would be recovered as well. Thus this ethanol-washed aliquot would represent the total amount of stilbenoids produced in PALCPR-control and can be compared to the total amount of stilbenoids produced in the PALCPR-solvent culture. Indeed, a similar ethanol wash performed on the solvent phase did not result in an increase in the titers of stilbenoid- and stilbenoid intermediates, indicating that the solvent phase truly captured all the polar intermediates present in the medium broth or attached to cell membranes. Both aliquots were directly subjected to centrifugation at 3500 g, and the supernatant was analyzed for their content of stilbenoids and their intermediates.

The results are shown in the following table:

| | Coumaric acid (mg/l; % total) | Resveratrol (mg/l; % total) | Cinnamic acid (mg/l; % total) | Pinosylvin (mg/l; % total) |
|---|---|---|---|---|
| PALCPR-solvent | | | | |
| Upper phase (0.3 L) | — | 24.23; 36.2 | 20.72; 56.9 | 55.84; 95.2 |
| Lower phase (1 L) | — | 12.79; 63.8 | 4.72; 43.1 | 0.85; 4.8 |
| Total produced in 1 L | — | 20.09; 100 | 10.93; 100 | 17.6; 100 |
| PALCPR-control | | | | |
| Supernatant, ethanol | — | 20.01 | 9.70 | 22.63 |
| Supernatant, no ethanol | — | 11.43 | 3.59 | 1.74 |

Figure 1B:
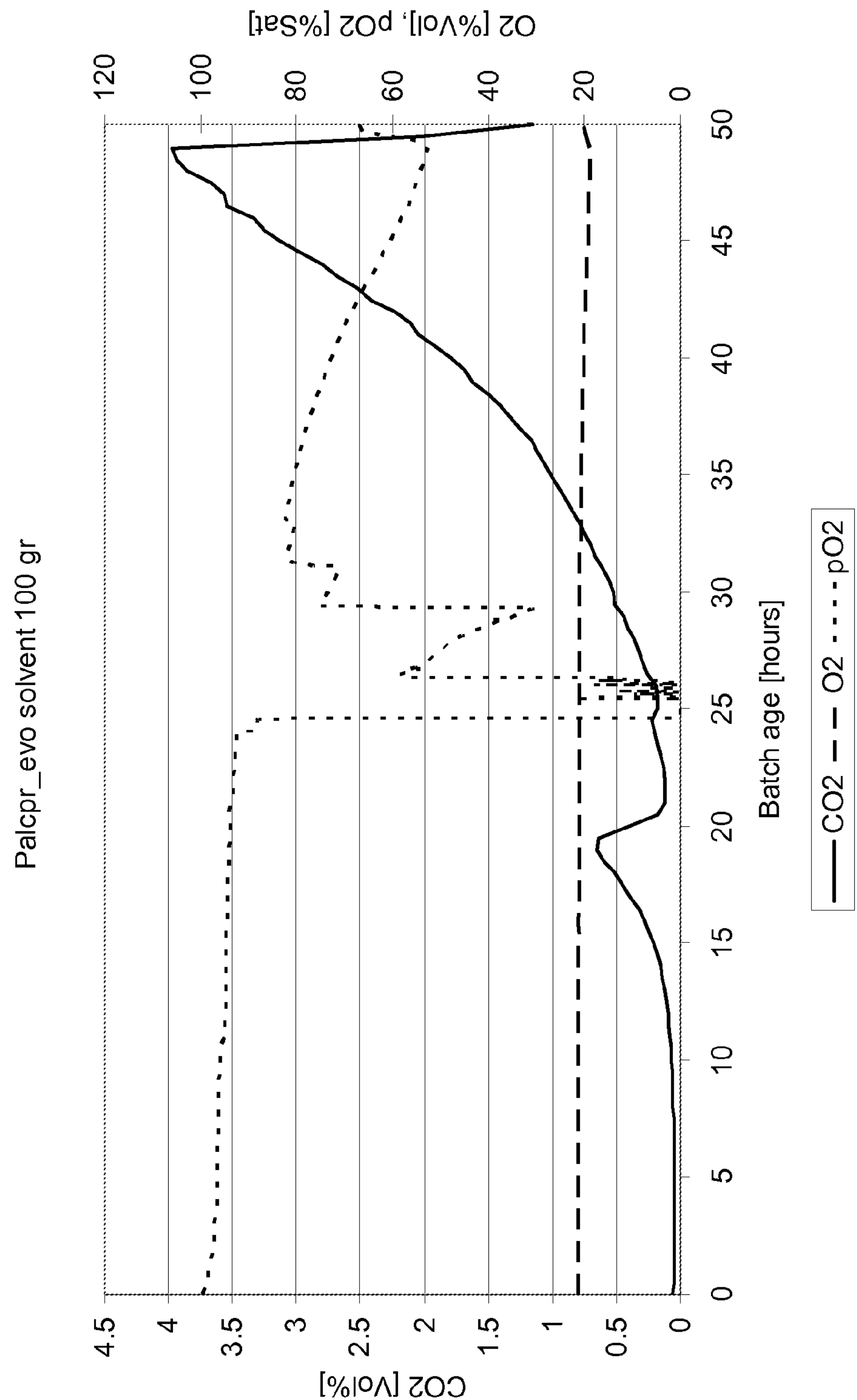
FIG. 1B: Fermentation profile for PALCPR-solvent (see Example 3): $CO_2$-evolution (CO2 Vol %), $O_2$ consumption ($O_2$ Vol %) and dissolved oxygen ($PO_2$% Sat) are shown.

The cells in the PALCPR-control culture consumed the galactose in 17 hours, whereas the galactose in the PALCPR-solvent culture was depleted after a little less than 25 hours. Based upon the $CO_2$ production the specific growth rate was estimated to be 0.23 1/h for the cells in the PALCPR-control culture, and 0.13 1/h for the cells in the PALCPR-solvent culture (FIGS. 1A and 1B). The final biomass content was 27.5 g/l in the PALCPR-control culture and 19.6 g/l in the PALCPR-solvent culture.

For the determination of stilbenoids, samples were taken at the point of galactose depletion. For the PALCPR-solvent culture, an aliquot of 25 ml of cell broth was collected, and phase separation was initiated by centrifugation at 3500 g for 5 minutes. Both the upper octylacetate phase and the lower aqueous medium phase were collected separately with a pipet and directly analyzed for their content of stilbenoids and intermediates by HPLC as follows:

For quantitative analysis of cinnamic acid, coumaric acid, resveratrol and pinosylvin, samples were subjected to separation by high-performance liquid chromatography (HPLC) prior to uv-diode-array detection at $\lambda$=306 nm. A Phenomenex (Torrance, Calif., USA) Luna 3 micrometer C18 (100× 2.00 mm) column was used at 60° C. As mobile phase a The results demonstrated that the PALCPR strain was able to grow in the presence of a solvent mixture containing 200 ml dodecane, and 100 ml octylacetate, growth rate and biomass yield were Blighty impaired compared to the control fermentation without solvents, however, production of stilbenoids and intermediates was not substantially affected and total titers were similar to the control culture. The solvent mixture was able to capture 95% of the stilbenoid pinosylvin and 36% of the more polar stilbenoid resveratrol. Obviously, the non-polar dodecane fraction in the solvent mixture sufficiently obscured the toxic effects on cells of the more polar and hence more toxic octylaceate fraction. The polarity of the mixture was indeed sufficiently high to capture almost all of the stilbenoid pinosylvin, but did not fully capture the more polar stilbenoid resveratrol.

The PALCPR control culture produced a persistent brown precipitate that settled on the inner vessel wall and baffles, and moreover fouled vital fermentor parts such as the stirrer shaft, gas-outlet, pH- and dO probe that would endanger a proper control of the fermentation process parts sstirrer shaf precipitates on said fermentor components. The PALCPR-solvent culture, however, did not show fouling of said fermentor components. Instead, a creamy/gelly substance was formed that remained in the fermentation broth, but manifested as an interface between the medium and the solvent phase after centrifugation. This "third" phase did not contain substantial amounts of stilbenoids or intermediates and could be discarded relatively easily.

Example 4

Determination of Intracellular and Extracellular Levels of Stilbenoids in a Batch Culture of an Evolved Strain of PALCPR The solvent mixture described in the previous example was not capable to capture all resveratrol produced, therefore a fermentation was initiated to adapt the cells to grow in the presence of a solvent mixture that contained solely the more polar and thus more toxic solvent octylacetate. The cells of the PALCPR-solvent culture described in the previous example were taken as starting point because the presence of the solvent mixture would possibly have already evoked adaptation of cells to solvents. For that, cells of the culture described in the previous example were harvested during mid-exponential-phase and stored at −80° C. in 15% glycerol and subsequently a fermentor, containing the same medium as described in the previous example with 10 g/l glucose and 100 g/l galactose, was then inoculated with cells of said PALCPR-solvent culture. The cells were allowed to fully consume the glucose at a stirring speed of 1000 rpm with an average dissolved oxygen content of above 70% of saturated air. At the onset of galactose consumption, the stirring rate was turned down to 300 rpm, after which slowly 100 ml of octylacetate was added.

Figure 2:
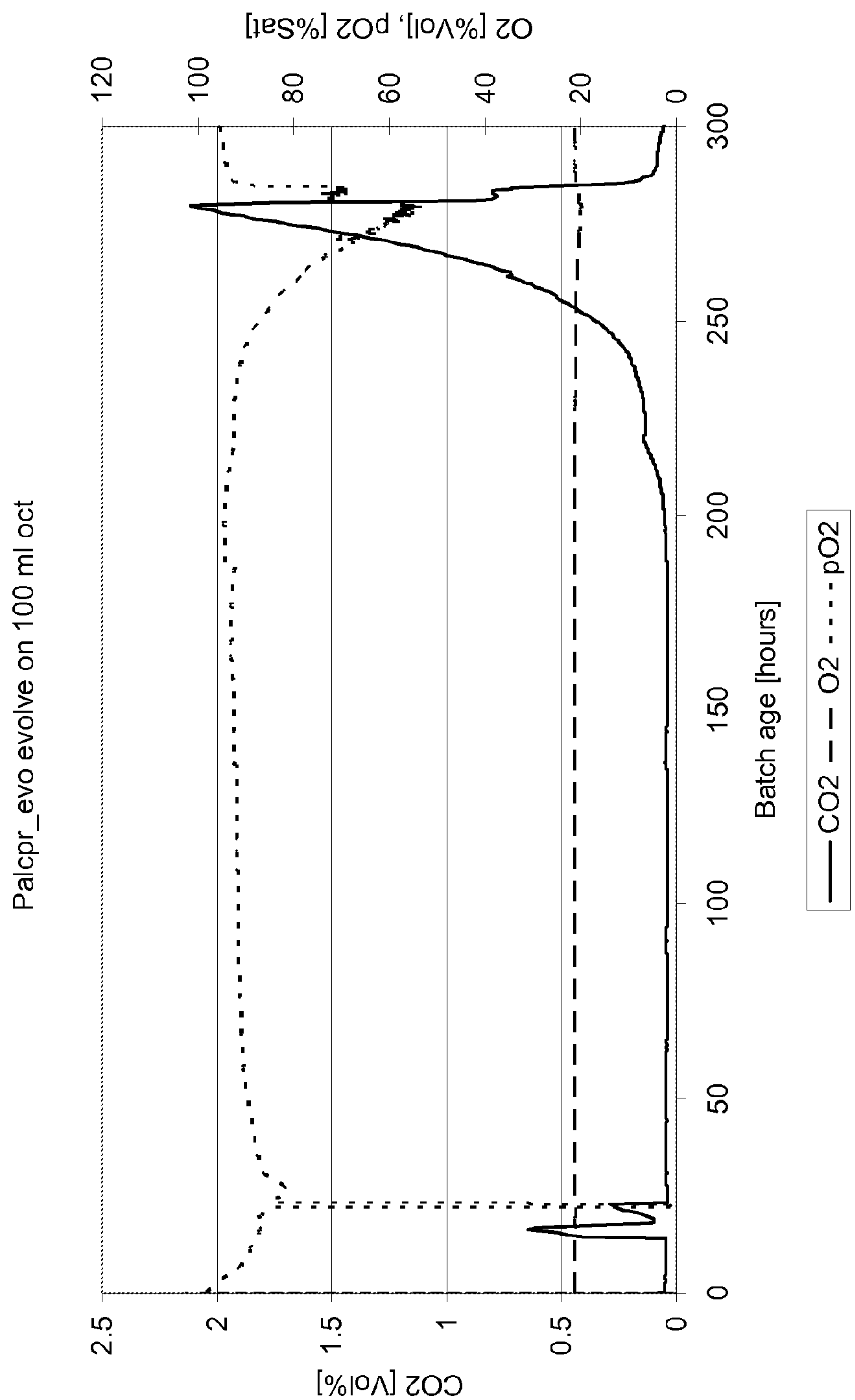
FIG. 2: Fermentation profile for PALCPR-evolved-I (Example 4): $CO_2$-evolution (CO2 Vol %), $O_2$ consumption ($O_2$ Vol %) and dissolved oxygen ($PO_2$% Sat) are shown.

Upon addition of octylacetate consumption of galactose was immediately arrested, the dissolved oxygen content increased to almost 99% of saturated air, $O_2$— consumption and $CO_2$ production halted, all indicating that proliferation of cells arrested. However after approximately 170 hours, the $CO_2$ signal slowly increased, Dissolved oxygen slowly decreased, indicating that cells started to grow. Galactose consumption indeed commenced again. A small arrest in $CO_2$ production again occurred after 20 hours which, however, recovered after 5 hours, after which the cells grew exponentially with concomitant production of $CO_2$, consumption of galactose within less than 40 hours. Based upon the $CO_2$ production the specific growth rate was estimated to be 0.062 1/h (FIG. 2). The final biomass concentration was 21.6 g/l.

For the determination of stilbenoids, an aliquot of 25 ml of cell broth was collected, and phase separation was initiated by centrifugation at 3500 g for 5 minutes. Both the upper octylacetate phase and the lower aquous medium phase were collected separately with a pipet and directly analyzed for their content of stilbenoids and intermediates by HPLC. The total concentration of stilbenoid intermediates that was produced was then calculated by dividing the concentrations in the upper phase with a factor of 10 and then adding them to the concentrations that were observed in the lower phase. The results are shown in the following table:

| Evolved PALCPR in 2-phase fermentation | Coumaric acid (mg/l; % total) | Resveratrol (mg/l; % total) | Cinnamic acid (mg/l; % total) | Pinosylvin (mg/l; % total) |
|---|---|---|---|---|
| Upper phase (0.1 L) | 233.4; 18.0 | 163.0; 92.6 | 408.0; 52.5 | 32.0; 100 |
| Lower phase (1 L) | 106.3; 82.0 | 1.3; 7.4 | 36.9; 47.5 | 0; 0 |
| Total produced in 1 L | 129.64; 100 | 17.6; 100 | 77.7; 100 | 3.2; 100 |

The results demonstrated clearly that strain PALCPR was able to adapt after 170 hours to the presence of 100 ml octylacetate. Though the growth rate was indeed lower than the PALCPR-control- and PALCPR-solvent culture in the previous example, the final biomass concentration was similar to said cultures.

The solvent mixture was now able to capture 100% of the stilbenoid pinosylvin and 92% of the more polar stilbenoid resveratrol. That result demonstrated that the polarity of the mixture was indeed sufficiently high to capture both the stilbenoids pinosylvin and resveratrol almost fully to completion. The total amount of resveratrol produced was comparable with the PALCPR-control and PALCPR-solvent cultures in the previous example, however, the culture now produced relatively high amounts of the intermediate coumaric acid, substantial amounts of cinnamic acid and very minor amounts of the stilbenoid pinosylvin. Possibly the observed change in product profile could be the result of the solvent that drained the intermediates away from the cells, thereby changing the intracellular concentrations in the cells and with that influence the product pattern through the kinetic properties of the enzymes. In case that a resveratrol producing strain is preferred, the addition of a solvent clearly could simplify down-stream processing by capturing the resveratrol, and at the same time impairing production of other similar stilbenoids.

Moreover, similar to the PALCPR-solvent culture in previous example, no persistent brown precipitate was produced that would otherwise have fouled vital fermentor parts, but a creamy/gelly substance was formed that manifested as a "third" phase and which could easily be discarded.

Example 5

Figure 3:
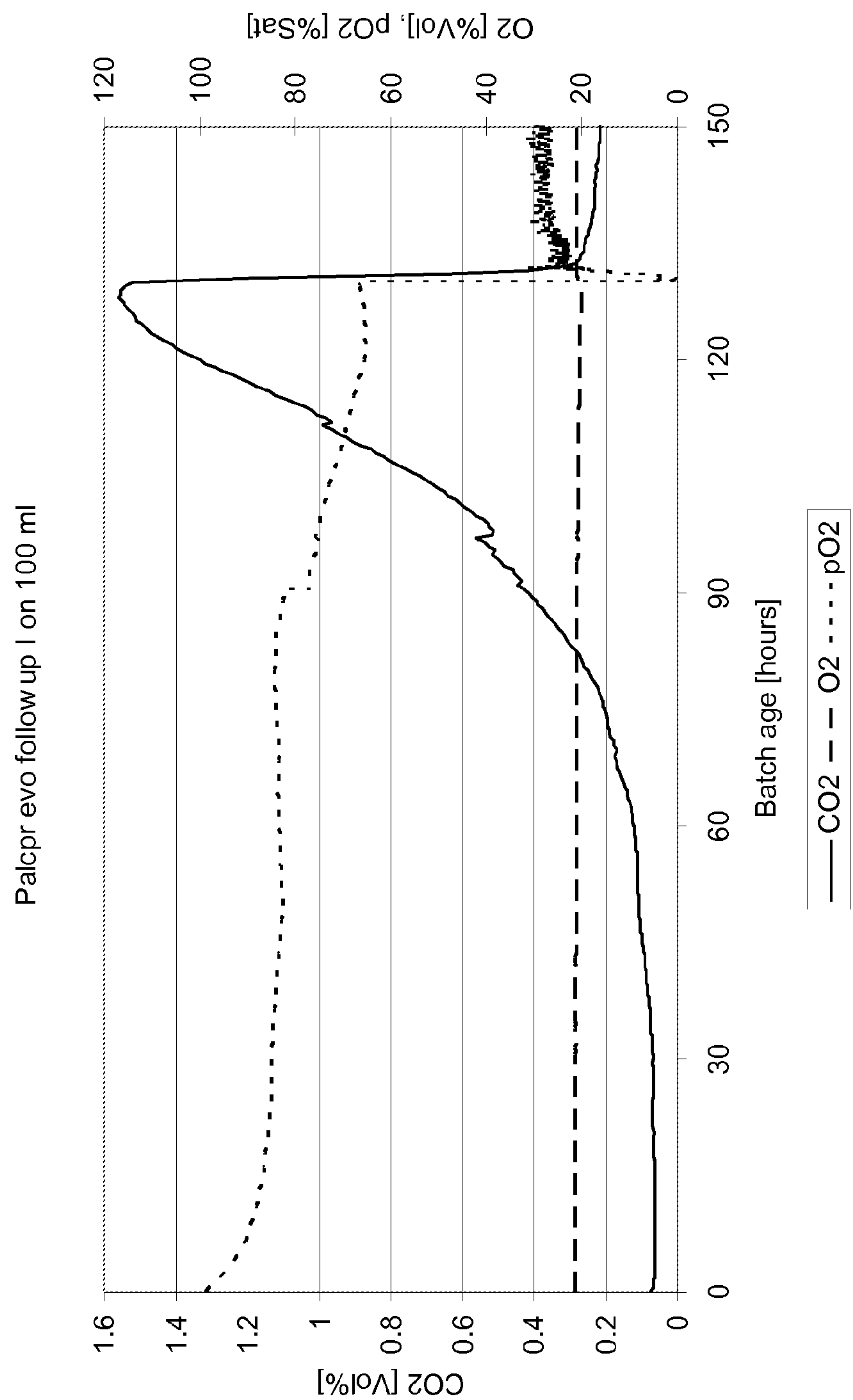
FIG. 3: Fermentation profile for PALCPR-evolved-II (Example 5): $CO_2$-evolution (CO2 Vol %), $O_2$ consumption ($O_2$ Vol %) and dissolved oxygen ($PO_2$% Sat) are shown.

Determination of Intracellular and Extracellular Levels of Stilbenoids in a Batch Culture of a Further Evolved Strain of PALCPR The evolved PALCPR-evolved-I strain described in the previous example still displayed a long lag-phase to adapt to the solvent phase. In order to further improve said strain in terms of length of lag-phase and growth rate, a 25 ml aliquot of the exponentional growing PALCPR-evolved-I strain was used to inoculate a fermentor, containing a similar medium as described in the previous example. However, the medium now only contained 100 g/l galactose and did contain 100 ml of octylacetate from the beginning of the fermentation. In addition, the stirrer speed was instantly set at 800 rpm. Upon inoculation of the fermentor, consumption of galactose only commenced after approximately 40 hours, indicated by a slow increase in $CO_2$ signal, a decrease in dissolved oxygen and addition of base. Indeed the cells continued to grow exponentially with concomitant production of $CO_2$, and consumed the galactose within less than 90 hours. Based upon the $CO_2$ production the specific growth rate was estimated to be 0.041 1/h (FIG. 3). The final biomass concentration was 21.5 g/l. The strain is referred to as PALCPR-evolved-II.

For the determination of stilbenoids, an aliquot of 25 ml of cell broth was collected, and phase separation was initiated by centrifugation at 3500 g for 5 minutes. Both the upper octylacetate phase and the lower aquous medium phase were collected separately with a pipet and directly analyzed for their content of stilbenoids and intermediates by HPLC. The total concentration of stilbenoid intermediates that was produced was then calculated by multiplying the concentrations in the upper phase with a factor of 0.3 and then adding them up to the concentrations that were observed in the lower phase. The results are shown in the following table:

| Evolved PALCPR in 2-phase fermentation | Coumaric acid (mg/l; % total) | Resveratrol (mg/l; % total) | Cinnamic acid (mg/l; % total) | Pinosylvin (mg/l; % total) |
|---|---|---|---|---|
| Upper phase (0.1 L) | 383.9; 59.3 | 210.4; 91.3 | 163.4; 88.6 | 30.7; 100 |
| Lower phase (1 L) | 26.3; 40.7 | 2.0; 8.7 | 2.1; 11.4 | 0; 0 |
| Total produced in 1 L | 64.7; 100 | 23.0; 100 | 18.4; 100 | 3.1; 100 |

The results demonstrated clearly that strain PALCPR-evolved-II was able to grow on a medium that contained 100 ml of octyl acetate from the beginning with a stirring speed immediately set at 800 rpm. The lag-phase of 40 hours was already considerably shorter than the 170 hrs described in the previous example, though at the expense of the growth rate that decreased to 0.041 1/h and with that galactose was depleted only after approximately 90 hours. Though the growth rate was indeed lower than the PALCPR-evolved-I culture in the previous example, the final biomass concentration was similar to said culture.

The solvent mixture was able to capture 100% of the stilbenoid pinosylvin and 91% of the more polar stilbenoid resveratrol. The total amount of resveratrol produced was higher than the PALCPR-evolved-I culture and the PALCPR-control and PALCPR-solvent cultures in the previous examples. However, the culture now produced lower amounts of the intermediates coumaric acid and cinnamic acid, which could be a result of the adaptation of the cells to the solvent.

Moreover, no persistent brown precipitate was produced that would otherwise have fouled vital fermentor parts, but a creamy/gelly substance was formed that manifested as a “third” phase and which could easily be discarded.

Example 6

Figure 4:
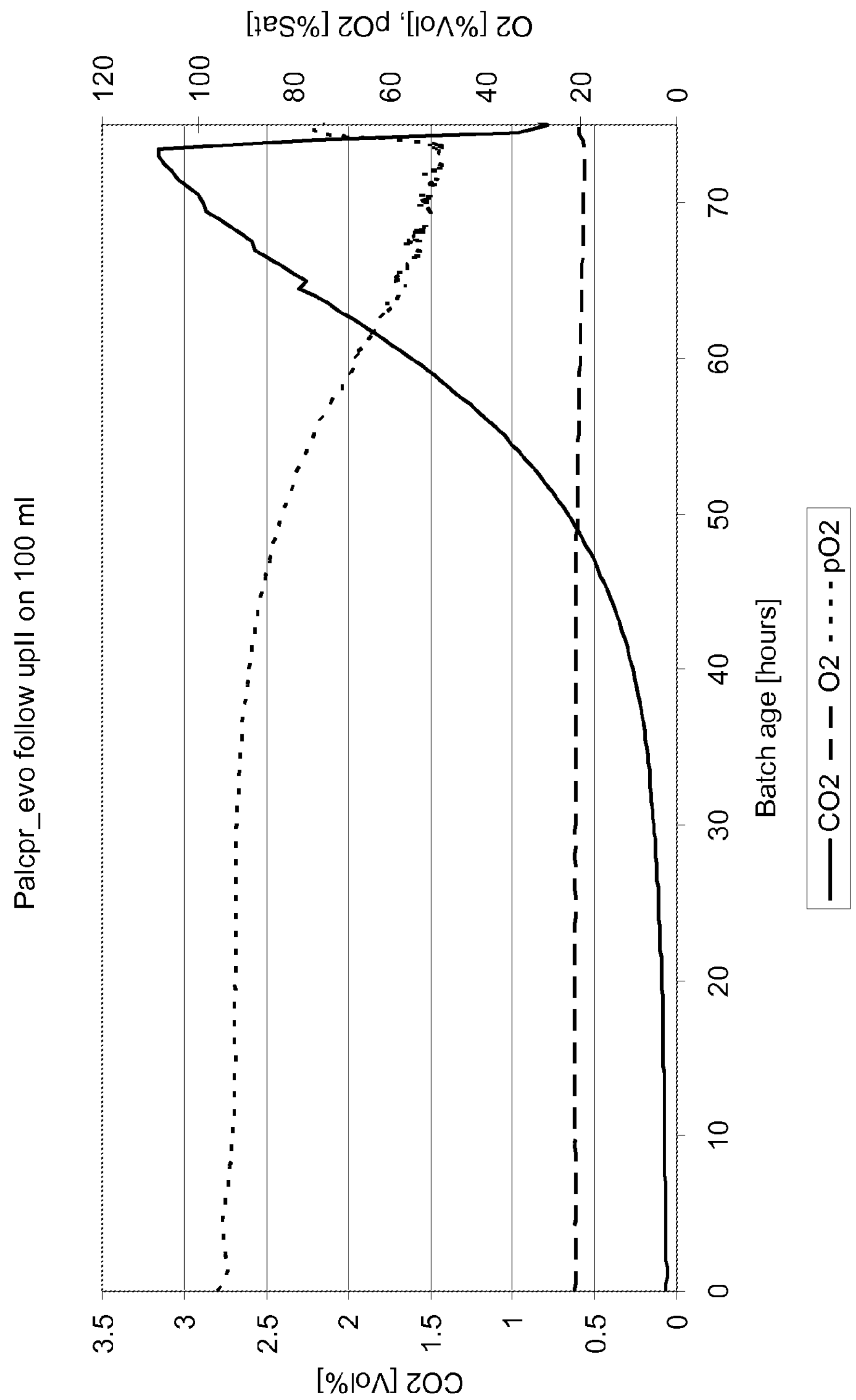
FIG. 4: Fermentation profile for PALCPR-evolved-III (Example 6): $CO_2$-evolution (CO2 Vol %), $O_2$ consumption ($O_2$ Vol %) and dissolved oxygen ($PO_2$% Sat) are shown.

Determination of Intracellular and Extracellular Levels of Stilbenoids in a Batch Culture of an Even Further Evolved Strain of PALCPR The evolved PALCPR-evolved-II strain described in the previous example still displayed a shorter lag-phase than PALCPR-evolved-I but the growth rate was rather low with 0.041 1/h. Therefore, to further improve said strain in terms of both length of lag-phase and growth rate, a 50 ml aliquot of the exponentional growing PALCPR-evolved-II strain was used to inoculate a fermentor, containing a similar medium as described in the previous example (thus containing 100 g/l galactose 100 ml of octylacetate from the beginning of the fermentation). The stirrer speed was instantly set at 800 rpm. Upon inoculation of the fermentor, consumption of galactose already commenced after less then 20 hours, indicated by a slow increase in $CO_2$ signal, a decrease in dissolved oxygen and addition of base. Indeed the cells further grew exponentially with concomitant production of $CO_2$, and now consumed the galactose within approximately 50 hours. Based upon the $CO_2$ production the specific growth rate was estimated to be 0.091 1/h (FIG. 4). The final biomass concentration was 18.9 g/l. The strain is referred to as PALCPR-evolved-III.

For the determination of stilbenoids, an aliquot of 25 ml of cell broth was collected, and phase separation was initiated by centrifugation at 3500 g for 5 minutes. Both the upper octylacetate phase and the lower aquous medium phase were collected separately with a pipet and directly analyzed for their content of stilbenoids and intermediates by HPLC. The total concentration of stilbenoid intermediates that was produced was then calculated by dividing the concentrations in the upper phase with a factor of 10 and then adding them to the concentrations that were observed in the lower phase. The results are shown in the following table:

| Evolved PALCPR in 2-phase fermentation | Coumaric acid (mg/l; % total) | Resveratrol (mg/l; % total) | Cinnamic acid (mg/l; % total) | Pinosylvin (mg/l; % total) |
|---|---|---|---|---|
| Upper phase (0.1 L) | 105.8; 40.0 | 223.6; 90.3 | 298.7; 71.3 | 167.9; 90.3 |
| Lower phase (1 L) | 15.9; 60.0 | 2.4; 9.7 | 12.0; 28.7 | 1.8; 9.7 |
| Total produced in 1 L | 26.5; 100 | 24.8; 100 | 41.9; 100 | 18.6; 100 |

The results demonstrated clearly that strain PALCPR-evolved-III was able to grow on a medium that contained 100 ml of octyl acetate from the beginning with the stirring speed immediately set at 800 rpm. The lag-phase of 20 hours was shortened further compared to the 40 hours lag-phase described in the previous example, and this time the growth rate increased from 0.041 1/h to 0.091 1/h. Concommitantly the galactose was depleted only after approximately 90 hours. Though the growth rate was indeed lower than the PALCPR-evolved-I culture in the previous example, the final biomass concentration was similar to said culture.

The solvent mixture was able to capture 100% of the stilbenoid pinosylvin and 91% of the more polar stilbenoid resveratrol. The total amount of resveratrol produced was similar to the PALCPR-evolved-II culture but higher than the PALCPR-control and PALCPR-solvent cultures in the previous examples. However, compared to the PALCPR-evolved-III culture, the PALCPR-evolved-III culture produced lower amounts of coumaric acid, higher amounts of cinnamic acid, and considerably higher amounts of pinosylvin. The change in the overall product profile of the phenylpropanoid intermediates could be the result of a further adaptation of the cells to the solvent.

Moreover, no persistent brown precipitate was produced that would otherwise have fouled vital fermentor parts, but a creamy/gelly substance was formed that manifested as a "third" phase and which could easily be discarded.

Example 7

Stilbenoid Production in *Aspergillus nidulans* AR1 *Aspergillus nidulans* AR1 has Deleted the Following Genes Genes argB2, pyrG89, veA a) Construction of a Filamentous Fungal Expression Vector, with argB (ornithine carbamoyltransferase) Marker.

The gene encoding argB including the homologous promoter and terminator sequence was amplified from *Aspergillus nidulans* AR1 genomic DNA using forward primer 5-CG GAATTC ATA CGC GGT TTT TTG GGG TAG TCA-3 (SEQ ID NO: 11) and the reverse primer 5-CG CCCGGG TAT GCC ACC TAC AGC CAT TGC GAA-3 (SEQ ID NO: 12) with the 5' overhang containing the restriction sites EcoRI and XmaI respectively. The incorporated restriction sites in the PCR product allowed insertion into pUC19 (New England biolabs, Ipswich, Mass.) digested with EcoRI and XmaI giving pUC19-argB.

The trpC (Indole-3-glycerol phosphate synthase) terminator was amplified from *A. nidulans* genomic DNA using forward primer 5-GC GGATCC ATA GGG CGC TTA CAC AGT ACA CGA-3 (SEQ ID NO: 13) and the reverse primer 5-CGGAGAGGGCGCGCCCGTGGCGGCCGC GGA TCC ACT TAA CGT TAC TGA-3 SEQ ID NO: 14 with the 5' overhang containing the restriction site BamHI and a 27 base pair adaptamer respectively.

The gpdA (glyceraldehyde-3-phosphate dehydrogenase) promoter was amplified from *A. nidulans* AR1 genomic DNA using forward primer 5-GCGGCCGCCACGGGCGCGCCCTCTCCG GCG GTA GTG ATG TCT GCT CAA-3 (SEQ ID NO: 15) and the reverse primer 5-CG AAGCTT TAT AAT TCC CTT GTA TCT CTA CAC-3 SEQ ID NO:16 with the 5' overhang containing a 27 base pair adaptamer and the restriction site HindIII respectively.

The fusion PCR product of fragment trpC and gpdA with the incorporated restriction sites allow insertion into pUC19-argB digested with BamHI and HindIII yielding pAT3.

b) Construction of a Filamentous Fungal Expression Vector with pyrG (orotidine-5'-monophosphate decarboxylase) Marker for expression of C4H (Cinnamate-4-hydroxylase) in *A. nidulans* AR1.

The gene encoding C4H was reamplified from the yeast plasmid pESC-URA-PAL2-C4H (WO2006089898) using the forward primer 5-CG G CGCG C ATA ATG GAC CTC CTC TTG CTG GAG-3 SEQ ID NO:17 and the reverse primer 5-GG GC GGCC GC TTA TTA ACA GTT CCT TGG TTT CAT AAC G-3 SEQ ID NO: 18 with the 5' overhang containing the restriction sites BssHII and NotI respectively. The incorporated restriction sites in the PCR product allowed insertion into pAT3 digested with BssHII and NotI giving pAT3-C4H. The construct was verified by restriction enzyme cut and sequencing. The argB marker was removed by using the two following restriction enzymes BsiWI and PciI.

The gene encoding pyrG including the homologous promoter and terminator sequence was reamplified from *Aspergillus fumigatus* genomic DNA using the forward primer 5-CGT GTAC AATA TTA AT TAA CGAGA GCG AT CGC AAT AAC CGT ATT ACC GCC TTT GAG-3 SEQ ID NO: 19 and reverse primer 5-CGA CATG TAT TCC CGG GAA GAT CTC ATG GTC A-3 SEQ ID NO: 20 with the 5' overhang containing the restriction sites BsrGI, PacI, AsiSI in the forward primer and PciI in the reverse primer. The incorporated restriction sites in the PCR product allowed insertion into pAT3 digested with BsiWI and PciI giving pAT3-C4H-pyrG. The construct was verified by restriction enzyme cut and sequencing.

c) Construction of a Filamentous Fungal Expression Vector with argB Marker for Expression of 4CL1 (4-coumarate-CoA ligase) in *A. nidulans* AR1

The gene encoding 4CL1 was reamplified from the yeast plasmid pESC-TRP-4CL1-VST1 using the forward primer 5-GCGGAGAGGGCGCG ATG GCG CCA CAA GAA CAA GCA-3 SEQ ID NO: 21 and the reverse primer 5-TGGATCCGCGGCCGC TCA CAA TCC ATT TGC TAG TTT TGC-3 SEQ ID NO: 22. The 4CL1 gene was inserted into a pAT3 vector digested with BssHII and NotI using the Infusion™ PCR cloning Technology (Clontech, Mountain View, Calif.) to yield pAT3-4CL1. The construct was verified by restriction enzyme cut and sequencing.

d) Construction of a Filamentous Fungal Expression Vector with argB Marker for Expression of VST1 (resveratrol synthase) in *A. nidulans* AR1

The gene encoding VST1 was reamplified from the yeast plasmid pESC-TRP-4CL1-VST1 using the forward primer 5-CG G CGCG C ATA ATG GCA TCC GTA GAG GAG TTC-3 SEQ ID NO: 23 and the reverse primer 5-GG GC GGCC GC TTA TCA TTA GTT AGT GAC AGT TGG AA-3 SEQ ID NO: 24 with the 5' overhang containing the restriction sites BssHII and NotI respectively. The incorporated restriction sites in the PCR product allowed insertion into pAT3 digested with BssHII and NotI giving pAT3-VST1. The construct was verified by restriction enzyme cut and sequencing.

e) Expression of the Pathway Leading to pinosylvin in *A. nidulans* AR1 (The strain has deletions (argB2, pyrG89, veA1)) using C4H, 4CL1 and VST1.

The transformation of the *A. nidulans* AR1 fungal cell was conducted in accordance with methods known in the art by protoplastation using cell wall lysing enzymes (glucanex, novozymes) Tilburn et al., 1983. Random integration of C4H, 4CL1 and VST1 was conducted in two steps. Plasmid pAT3-4CL1 and pAT3-VST1 were linearized using restriction enzyme BmrI and integrated in the genome by co-transformation according to Guerra et al., 2006 utilizing the auxotrophic marker argB. A transformant containing a 4CL1 and VST1 expression cassette was isolated and a successive transformation with pAT3-C4H-pyrG, which was linearized with BmrI, gave a recombinant *A. nidulans* strain containing C4H, 4CL1 and VST1.

Example 8

Stilbenoid Production in *Escherichia coli* a) Construction of a Bacterial Vector for Expression of PAL2 in *Escherichia coli.*

The plasmids that were used in the following examples contained one or more marker genes to allow the microorganism that harbour them to be selected from those which do not. The selection system is based upon dominant markers, e.g. resistance against ampicillin and kanamycin. In addition, the plasmids contained promoter- and terminator sequences that allowed the expression of the recombinant genes. Furthermore, the plasmids contained suitable unique restriction sites to facilitate the cloning of DNA fragments and subsequent identification of recombinants. In this example the plasmids contained either the ampicillin resistance gene, designated as pET16b (Novagen), or the kanamycin resistance gene, designated as pET26b (Novagen).

The gene encoding PAL2, isolated as described previously, was reamplified by PCR from the plasmid pESC-URA-PAL2 using forward- and reverse primers, with 5' overhangs containing suitable restriction sites. The introduction of said restriction sites at the 5' and 3' ends of the gene allowed ligation of the restricted PCR product into a digested pET16B vector that contained the T7 promoter. The resulting plasmid, pET16B-PAL2, contained the gene encoding PAL2 under the control of the T7 promoter.

b) Construction of a Bacterial Vector for Expression of 4CL1 and VST1 in *Escherichia coli*.

The gene encoding 4CL1, isolated as described previously, was reamplified by PCR from the plasmid pESC-URA-4CL1-VST1, using forward- and reverse primers, with 5' overhangs containing suitable restriction sites. The introduction of said restriction sites at the 5' and 3' ends of the gene allowed ligation of the restricted PCR product into a digested pET26B vector. The resulting plasmid, pET26B-4CL1, contained the gene encoding for 4CL1 under the control of the T7 promoter from *Lactobacillus* lactis.

The gene encoding VST1, isolated as described in previously, was reamplified by PCR from the plasmid pESC-URA-4CL1-VST1 using forward- and reverse primers, with 5' overhangs containing suitable restriction sites. The introduction of said restriction sites at the 5' and 3' ends of the gene allowed ligation of the restricted PCR product into a digested pET16B vector. The resulting plasmid, pET16B-VST1, contained the gene encoding VST1 under the control of the T7 promoter. The T7 promoter and the gene encoding VST1 were reamplified as one fragment by PCR from the plasmid pET16B-VST1 using forward and reverse primers, with 5' overhangs containing suitable restriction sites.

The introduction of said restriction sites at the 5' and 3' ends of the DNA fragment allowed ligation of the restricted PCR product into the digested plasmid pET26B-4CL1. The resulting plasmid, pET26B-4CL1-VST1, contained the genes encoding 4CL1 and VST1, each under the control of their individual T7 promoter. The sequence of the genes encoding 4CL1 and VST1 was verified by sequencing of two different clones of pET26B-4CL1-VST1.

c) Expression of the Pathway to pinosylvin in *Escherichia coli*

*Escherichia coli* strains were transformed with the vectors described in (a) and (b), separately or in combination. The transformation of the bacterial cell was conducted in accordance with methods known in the art, for instance, by using competent cells or by electroporation (see, e.g., Sambrook et al., 1989). Transformants were selected on medium containing the antibiotics ampicillin and kanamycin and streak purified on the same medium.

*Escherichia coli* strain BL21 (DE3) was transformed separately with the vector pET16B-PAL2 (a), yielding the strain FSEC-PAL2; and with pET26B-4CL1-VST1 (b), yielding strain FSEC-4CL1VST1. In addition, *Escherichia coli* strain BL21 (DE3) was co-transformed with pET16B-PAL2 (a) and pET26B-4CL1-VST1 (n), and the transformed strain was named FSEC-PAL24CL1VST1.

Example 9

Construction of Strain FS09229, Containing the Phenylpropanoid Pathway with Glucose-constitutive Promoters I) Isolation of Genes Encoding PAL C4H, 4CL2 and VST1

4-coumarate:CoenzymeA ligase (4CL2) SEQ ID NO: 25 (Hamberger and Hahlbrock 2004; Ehlting et al., 1999;) was isolated via PCR from *A. thaliana* cDNA (BioCat, Heidelberg, Germany) using suitable primers.

The PAL2 gene encoding *Arabidopsis thaliana* resveratrol phenylalanine ammonia lyase (Cochrane et al., 2004) was synthesized by GenScript Corporation (Piscataway, N.J.). The amino acid sequence was used as template to generate a synthetic gene codon (SEQ ID NO: 26) optimized for expression in *S. cerevisiae*. The synthetic PAL2 gene was delivered inserted in *E. coli* pUC57 vector. The synthetic gene was purified from the pUC57 vector by amplifying it by forward primer 5-CAC TAA AGG GCG GCC GCA TGG ACC AAA TTG AAG CA-3 SEQ ID NO: 27 and reverse primer 5-AAT TAA GAG CTC AGA TCT TTA GCA GAT TGG AAT AGG TG-3 SEQ ID NO: 28 and purified from agarose gel using the QiaQuick Gel Extraction Kit (Qiagen).

The C4H gene encoding *Arabidopsis thaliana* cinnamate-4-hydroxylase (Hamberger and Hahlbrock 2004; Ehlting et al., 1999) was synthesized by GenScript Corporation (Piscataway, N.J.). The amino acid sequence was used as template to generate a synthetic gene (SEQ ID NO: 29) (S codon optimized for expression in *S. cerevisiae*. The synthetic C4H gene was delivered inserted in *E. coli* pUC57 vector. The synthetic gene was purified from the pUC57 vector by amplifying it by forward primer 5-ATT TCC GAA GAA GAC CTC GAG ATG GAT TTG TTA TTG CTG G-3 SEQ ID NO:30 and reverse primer 5-AGT AGA TGG AGT AGA TGG AGT AGA TGG AGT AGA TGG ACA ATT TCT GGG TTT CAT G-3 SEQ ID NO: 31 and purified from agarose gel using the QiaQuick Gel Extraction Kit (Qiagen).

The ATR2 gene encoding *Arabidopsis thaliana* P450 reductase was synthesized by GenScript Corporation (Piscataway, N.J.). The amino acid sequence was used as template to generate a synthetic gene (SEQ ID NO: 32) codon optimized for expression in *S. cerevisiae*. The synthetic C4H gene was delivered inserted in *E. coli* pUC57 vector. The synthetic gene was purified from the pUC57 vector by amplifying it by forward primer 5-CCA TCT ACT CCA TCT ACT CCA TCT ACT CCA TCT ACT AGG AGG AGC GGT TCG G-3 SEQ ID NO:33 and reverse primer 5-ATC TTA GCT AGC CGC GGT ACC TTA CCA TAC ATC TCT CAG ATA TC-3 SEQ ID NO:34 and purified from agarose gel using the QiaQuick Gel Extraction Kit (Qiagen).

The VST1 gene encoding *Vitis vinifera* (grapevine) resveratrol synthase (Hain et al., 1993) was synthesized by GenScript Corporation (Piscataway, N.J.). The amino acid sequence was used as template to generate a synthetic gene codon optimized for expression in *S. cerevisiae*. The synthetic VST1 gene (SEQ ID NO: 35) was delivered inserted in *E. coli* pUC57 vector flanked by BamH1 and Xho1 restriction sites. The synthetic gene was amplified using forward primer 5-CCG GAT CCT CAT GGC ATC CGT CGA AGA GTT CAG G-3 SEQ ID NO: 36 and reverse primer 5-CGC TCG AGT TTT AGT TAG TAA CTG TGG GAA CGC TAT GC-3 SEQ ID NO:37 and purified from agarose gel using the QiaQuick Gel Extraction Kit (Qiagen).

II) Construction of a Yeast Vector for Galactose Induced Expression of 4CL2 and VST1

The gene encoding 4CL2 was isolated as described in section I. The amplified 4CL2 PCR-product using forward primer 5-GCG AAT TCT TAT GAC GAC ACA AGA TGT GAT AGT CAA TGA T-3 SEQ ID NO:38 and reverse primer 5-GCA CTA GTA TCC TAG TTC ATT AAT CCA TTT GCT AGT CTT GC-3 SEQ ID NO:39 was digested with EcoR1/Spe1 and ligated into EcoR1/Spe1 digested pESC-HIS vector (Stratagene), resulting in vector pESC-HIS-4CL2.

Two different clones of pESC-HIS-4CL2 were sequenced to verify the sequence of the cloned gene.

The gene encoding VST1 was isolated as described in section I. The amplified synthetic VST1 gene was digested with BamH1/Xho1 and ligated into BamH1/Xho1 digested pESC-HIS-4CL2. The resulting plasmid, pESC-HIS-4CL2-VST1, contained the genes encoding 4CL2 and VST1 under the control of the divergent galactose induced <=GAL1/GAL10=> promoters. The sequence of the gene encoding VST1 was verified by sequencing of two different clones of pESC-HIS-4CL2-VST1 (SEQ ID NO: 40).

III) Construction of a Yeast Vector for Galactose Induced Expression of PAL2 and C4H:ATR2 Fusion Gene The gene encoding PAL2 was isolated as described in section I. The amplified PAL2 PCR-product was inserted into NotI/BglII digested pESC-URA vector Stratagene), resulting in vector pESC-URA-PAL2. Two different clones of pESC-URA-PAL2 were sequenced to verify the sequence of the cloned gene.

The genes encoding C4H and ATR2 were isolated as described in section I. C4H was amplified using forward primer 5-ATT TCC GAA GAA GAC CTC GAG ATG GAT TTG TTA TTG CTG G-3 SEQ ID NO:41 and reverse primer 5-AGT AGA TGG AGT AGA TGG AGT AGA TGG AGT AGA TGG ACA ATT TCT GGG TTT CAT G-3 SEQ ID NO:42. ATR2 was amplified using forward primer 5-CCA TCT ACT CCA TCT ACT CCA TCT ACT CCA TCT ACT AGG AGG AGC GGT TCG G-3 SEQ ID NO:43 and reverse primer 5-ATC TTA GCT AGC CGC GGT ACC TTA CCA TAC ATC TCT CAG ATA TC-3 SEQ ID NO:44.

The amplified PCR products C4H and ATR2 were used as templates for the creation of the fusion gene C4H:ATR2 using the forward primer 5-ATT TCC GAA GAA GAC CTC GAG ATG GAT TTG TTA TTG CTG G-3 SEQ ID NO:41 and the reverse primer 5-ATC TTA GCT AGC CGC GGT ACC TTA CCA TAC ATC TCT CAG ATA TC-3 SEQ ID NO:44.

The Fusion gene C4H:ATR2 gene was inserted into XhoI/KpnI digested pESC-URA-PAL2 by Infusion™ technology (stratagene, La jolla, USA). The resulting plasmid, pESC-URA-PAL2-C4H:ATR2, contained the genes encoding PAL2 and C4H:ATR2 under the control of the divergent galactose induced <=GAL1/GAL10=> promoters. The sequence of the gene encoding C4H:ATR2 was verified by sequencing of two different clones of pESC-URA-PAL2-C4H:ATR2(SEQ ID NO: 45).

IV) Construction of Strong Constitutive Promoter Fragment TDH3

The 600 base pair TDH3 (GPD) promoter was amplified from *S. cerevisiae* genomic DNA using the forward primer 5'GC GAGCTC AGT TTA TCA TTA TCA ATA CTC GCC ATT TCA AAG SEQ ID NO: 46 containing a Sad restriction site and the reverse primer 5'-CG TCTAGA ATC CGT CGA AAC TAA GTT CTG GTG TTT TAA AAC TAA AA SEQ ID NO:47 containing a Xba1 restriction site. The amplified TDH3 fragment was digested with Sac1/Xba1 and ligated into Sac1/Xba1 digested plasmid pRS416 (Sikorski and Hieter, 1989) as described previously (Mumberg et al, 1995) resulting in plasmid pRS416-TDH3.

V) Construction of Constitutive Strong Promoter Fragment TEF1

The 400 base pair TEF1 promoter was amplified from *S. cerevisiae* genomic DNA using the forward primer 5'-GC GAGCTC ATA GCT TCA AAA TGT TTC TAC TCC TTT TTT ACT CTT SEQ ID NO:48 containing a Sad restriction site and the reverse primer 5'-CG TCTAGA AAA CTT AGA TTA GAT TGC TAT GCT TTC TTT CTA ATG A SEQ ID NO:49 containing a Xba1 restriction site. The amplified TEF1 fragment was digested with Sac1/Xba1 and ligated into Sac1/Xba1 digested plasmid pRS416 (Sikorski and Hieter, 1989) as described previously (Mumberg et al, 1995) resulting in plasmid pRS416-TEF1.

VI) Construction of Fused Divergent Constitutive TEF1 and TDH3 Promoter Fragment A divergent fusion fragment (FIG. 1) between TEF1 promoter and TDH3 promoter was constructed starting from PRS416-TEF1 and PRS416-TDH3.

The 600 base pair TDH3 fragment was reamplified from PRS416-TDH3 using the forward primer 5' TTGCGTATTGGGCGCTCTTCC GAG CTC AGT TTA TCA TTA TCA ATA CTC GC SEQ ID NO: 50 containing the underlined overhang for fusion PCR to TEF1 fragment and the reverse primer 5' AT GGATCC TCT AGA ATC CGT CGA AAC TAA GTT CTG SEQ ID NO: 51 containing the underlined BamH1 restriction site. This resulted in a fragment ready for fusion to the below TEF1 fragment.

The 400 base pair TEF1 fragment including a 277 base pair spacer upstream of the Sad restriction site was reamplified from PRS416-TEF1 using the forward primer 5' AT GAATTC TCT AGA AAA CTT AGA TTA GAT TGC TAT GCT TTC SEQ ID NO: 52 containing the underlined EcoR1 restriction site and the reverse primer 5' TGA TAA TGA TAA ACT GAG CTC GGA AGA GCG CCC AAT ACG CAA AC SEQ ID NO: 53 containing the underlined overhang for fusion to the TDH3 fragment. This resulted in a 680 base pair fragment ready for fusion to the TDH3 fragment.

The 600 base pair TEF1 fragment and the 600 base pair TDH3 fragments were joined together (fused) using fusion PCR with the forward primer 5' AT GAATTC TCT AGA AAA CTT AGA TTA GAT TGC TAT GCT TTC SEQ ID NO: 54 and the reverse primer 5' AT GGATCC TCT AGA ATC CGT CGA AAC TAA GTT CTG SEQ ID NO: 55, resulting in the divergent fragment <=TEF1/TDH3=> (SEQ ID NO: 56).

VII) Construction of a Yeast Vector for Constitutive Expression Induced of 4CL2 and VST1 pesc-HIS-TDH3-4CL2-TEF-VST1

The vector pESC-HIS-4CL2-VST1 (FIG. 2) with divergent galactose inducible promoters GAL1/GAL10 was sequentially digested with EcoR1 and BamH1 to remove the GAL1/GAL10 promoters.

The divergent constitutive <=TEF1/TDH3=> promoter fragment (Sequence ID 56) was reamplified with forward primers 5' ATGAATTC TCT AGA ATC CGT CGA AAC TAA GTT CTG SEQ ID NO: 57 and reverse primers AT GGA TCC TCT AGA AAA CTT AGA TTA GAT TGC TAT GCT TTC TTT CTA A SEQ ID NO: 58 to reverse the orientation of TEF and TDH3 promoters in the final construct, that is to revert construct pESC-HIS-TEF1-4CL2-TDH3-VST1 into pESC-HIS-TDH3-4CL2-TEF1-VST1. The reamplified fragment was sequentially digested with EcoR1 and BamH1 and ligated into the above vector without the GAL1/Gal10 fragment. This resulted in a vector pesc-HIS-TDH3-4CL2-TEF1-VST1 (FIG. 3) with replaced promoters, from GAL1/Gal10 to TDH3/TEF1 (SEQ ID NO: 59).

VIII) Marker Exchange of the Expression Vector pesc-HIS-TDH3-4CL2-TEF-VST1

The vector pesc-HIS-TDH3-4CL2-TEF-VST1 with divergent constitutive TDH3/TEF1 promoters was used as template for amplification by PCR with forward primer 5-TCG ACG GAT CTA TGC GGT GTG AAA TAC C-3 (SEQ ID NO: 60) and reverse primer 5-ACT CTC AGT ACA ATC TGC TCT GAT GCC G-3 (SEQ ID NO: 61) removing the His3 expression cassette.

The Ura3 expression cassette was amplified by PCR using forward primer 5-AGA GCAGATTGTA CTGAGAGT CAT CAG AGC AGA TTG TAC TGA GAG TGC-3 (SEQ ID NO: 62) and reverse primer 5-CAC ACC GCA TAG ATC CGT CGA GGA TTT TGC CGA TTT CGG CCT ATT GG-3 (SEQ ID NO: 63) and template pESC-URA-PAL2-C4H:ATR2. The two PCR fragments were fused by Infusion™ technology (stratagene, La Jolla, USA). This resulted in vector pesc-URA-TDH3-4CL2-TEF-VST1 with replaced auxotrophic marker, from his3 to ura3 (SEQ ID NO: 64).

IX) Construction of a Yeast Vector for Constitutive Expression of PAL2 and C4H:ATR2 Fusion Gene The vector pESC-URA-PAL2-C4H:ATR2 with divergent galactose inducible promoters GAL1/GAL10 was sequentially digested with NotI and XhoI to remove the GAL1/GAL10 promoters.

The divergent constitutive <=TEF1/TDH3=> promoter fragment was re-amplified with forward primer 5-TTC CAG CAA TAA CAA ATC CAT TTT GTA TCT AGA AAA CTT AGA TTA GAT TG-3 SEQ ID NO: 65 and reverse primer 5-CAT TGC TTC AAT TTG GTC CAT TTT GTA TCT AGA ATC CGT CGA AAC TAA GT-3 SEQ ID NO: 66. The PCR product was sequentially inserted into the above vector without the GAL1/Gal10 fragment using Infusion™ technology (stratagene, La Jolla, USA). This resulted in a vector pESC-URA-TDH3-PAL2-TEF1-C4H:ATR2 with replaced promoters, from GAL1/Gal10 to TEF1/TDH3 (SEQ ID NO: 67).

X) Marker Exchange of the Expression Vector pESC-URA-TDH3-PAL2-TEF1-C4H:ATR2

The vector pESC-URA-TDH3-PAL2-TEF1-C4H:ATR2 with divergent constitutive TDH3/TEF1 promoters was used as template for amplification by PCR with forward primer 5-TGA AAT ACC GCA CAG ATG-3 (SEQ ID NO: 68) and reverse primer 5-CTC TCA GTA CAA TCT GCT-3 (SEQ ID NO: 69) removing the Ura3 expression cassette.

The His3 expression cassette was amplified by PCR using forward primer 5-AGC AGA TTG TAC TGA GAG GAG CTT GGT GAG CGC TAG GA-3 (SEQ ID NO: 70) and reverse primer 5-C ATC TGT GCG GTA TTT CAC GGT ATT TTC TCC TTA CGC ATC-3 (SEQ ID NO: 71) and template pESC-HIS-4CL2-VST1. The two PCR fragments were fused by Infusion™ technology (stratagene, La Jolla, USA). This resulted in vector pESC-HIS-TDH3-PAL2-TEF1-C4H:ATR2 with replaced auxotrophic marker, from his3 to ura3 (SEQ ID NO: 72).

X1) Expression of the Pathway to Resveratrol in the Yeast *S. cerevisiae* Using PAL2, C4H:ATR2, 4CL2 and VST1

Yeast strains FS01529 containing the appropriate genetic markers were transformed with the vectors described in sections VIII and X giving FS09229. The transformation of the yeast cell was conducted in accordance with methods known tions VIII and X giving FS09229. The transformation of the yeast cell was conducted in accordance with methods known in the art by using competent cells, an alternative being for instance, electroporation (see, e.g., Sambrook et al., 1989). Transformants were selected on medium lacking uracil and histidine and streak purified on the same medium.

Example 10

Figure 9:
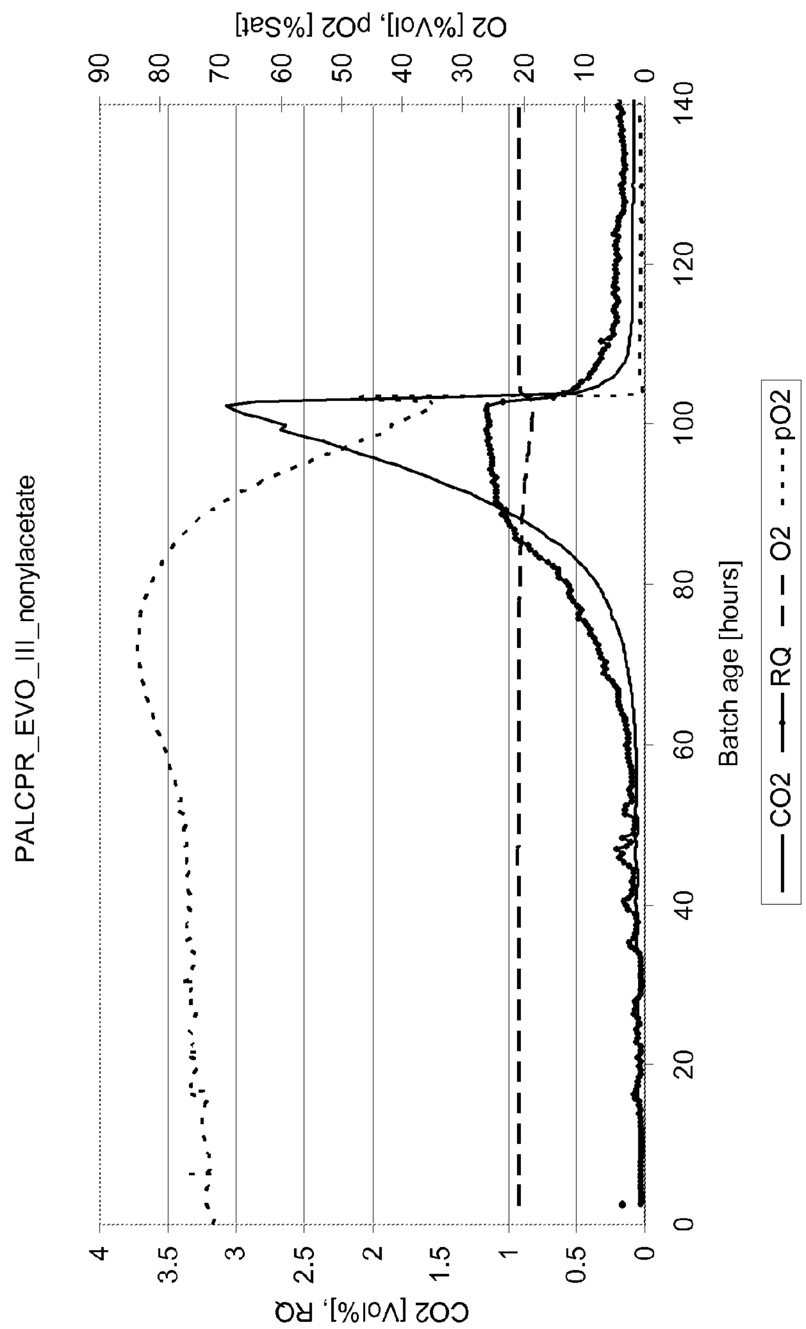
FIG. 9: History plot of parameters of cultivation measured in Example 10.

Determination of Intracellular and Extracellular Levels of Stilbenoids in a Batch Culture of a Further Evolved Strain of PALCPR The evolved PALCPR-evolved-III strain described in the previous example was grown in the presence of nonyl-acetate, a similar solvent as octylacetate with one additional carbon atom. A 1 ml aliquot of a glycerol stock that was made from an exponentional growing PALCPR-evolved-III strain was used to inoculate a fermentor, containing a similar medium as described in the previous example, containing only 100 g/l galactose and 100 ml of nonyl-acetate from the beginning of the fermentation. The stirrer speed was instantly set at 800 rpm. Upon inoculation of the fermentor, consumption of galactose only commenced after approximately 70 hours, indicated by a slow increase in $CO_2$ signal, a decrease in dissolved oxygen and addition of base. Indeed the cells continued to grow exponentially with concomitant production of $CO_2$, and consumed the galactose within less than 40 hours. Based upon the $CO_2$ production the specific growth rate was estimated to be 0.098 1/h (FIG. 9). The final biomass concentration was 36.7 g/l. The cultivation will be referred to as PALCPR-solvent. As a control-experiment said strain was grown in the similar medium without the addition of nonylacetate. Upon inoculation of the fermentor, consumption of galactose commenced already after approximately 40 hours, indicated by an increase in $CO_2$ signal, a decrease in dissolved oxygen and addition of base. Indeed the cells continued to grow exponentially with concomitant production of $CO_2$, and consumed the galactose within less than 30 hours. Based upon the $CO_2$ production the specific growth rate was estimated to be 0.17 1/h. The final biomass concentration was 25.4 g/l. The cultivation will be referred to as PALCPR-control.

For the determination of stilbenoids, an aliquot of 25 ml of cell broth was collected, and phase separation was initiated by centrifugation at 3500 g for 5 minutes. Both the upper nonylacetate phase and the lower aqueous medium phase were collected separately with a pipette and directly analyzed for their content of stilbenoids and intermediates by HPLC. The total concentration of stilbenoid intermediates that was produced was then calculated by dividing the concentrations in the upper phase with a factor of 10 and then adding them to the concentrations that were observed in the lower phase. The results are shown in the following table:

| | Coumaric acid (mg/l; % total) | Resveratrol (mg/l; % total) | Cinnamic acid (mg/l; % total) | Pinosylvin (mg/l; % total) |
|---|---|---|---|---|
| PALCPR-solvent | | | | |
| Upper phase (0.1 L) | — | 8.27; 100 | 252.82; 29.6 | — |
| Lower phase (1 L) | — | 0.0; 0.0 | 60.05; 70.4 | — |
| Total produced in 1 L | — | 0.83; 100 | 85.33; 100 | — |
| PALCPR-control | | | | |
| Supernatant | — | 0.48 | 76.36 | — |

The results demonstrated that strain PALCPR-evolved-III was able to grow on a medium that contained 100 ml of nonyl acetate from the beginning with a stirring speed immediately set at 800 rpm. The lag-phase of 70 hours was already considerably longer than the lag-phase of the PALCPR-control fermentation and also a bit longer then a similar fermentation in the presence of octylacetate described in a previous example. The growth rate of 0.098 l/h was similar to the cultivation in the presence of octylacetate and considerably lower than the PALCPR-control fermentation. Surprisingly the biomass concentration was higher than both PALCPR-control and the octylacetate fermentation.

In both the PALCPR-solvent and PALCPR-control fermentation, only cinnamic acid and resveratrol was produced. The stilbenoid profiles differ therewith previous described control- and solvent fermentations, which could be due to the difference between inocculating with either a fresh culture (previous examples) or with a glycerol stock (this example). Nevertheless, the solvent mixture was able to capture 100% of the stilbenoid resveratrol whereas only 25% of cinnamic acid was captured. The total amount of resveratrol produced was slightly higher than the PALCPR-control in this example Moreover, the culture produced none of the intermediates coumaric acid and pinosylvin, which could be a result of a further adaptation of the cells to the solvent.

Example 11

Figure 10:
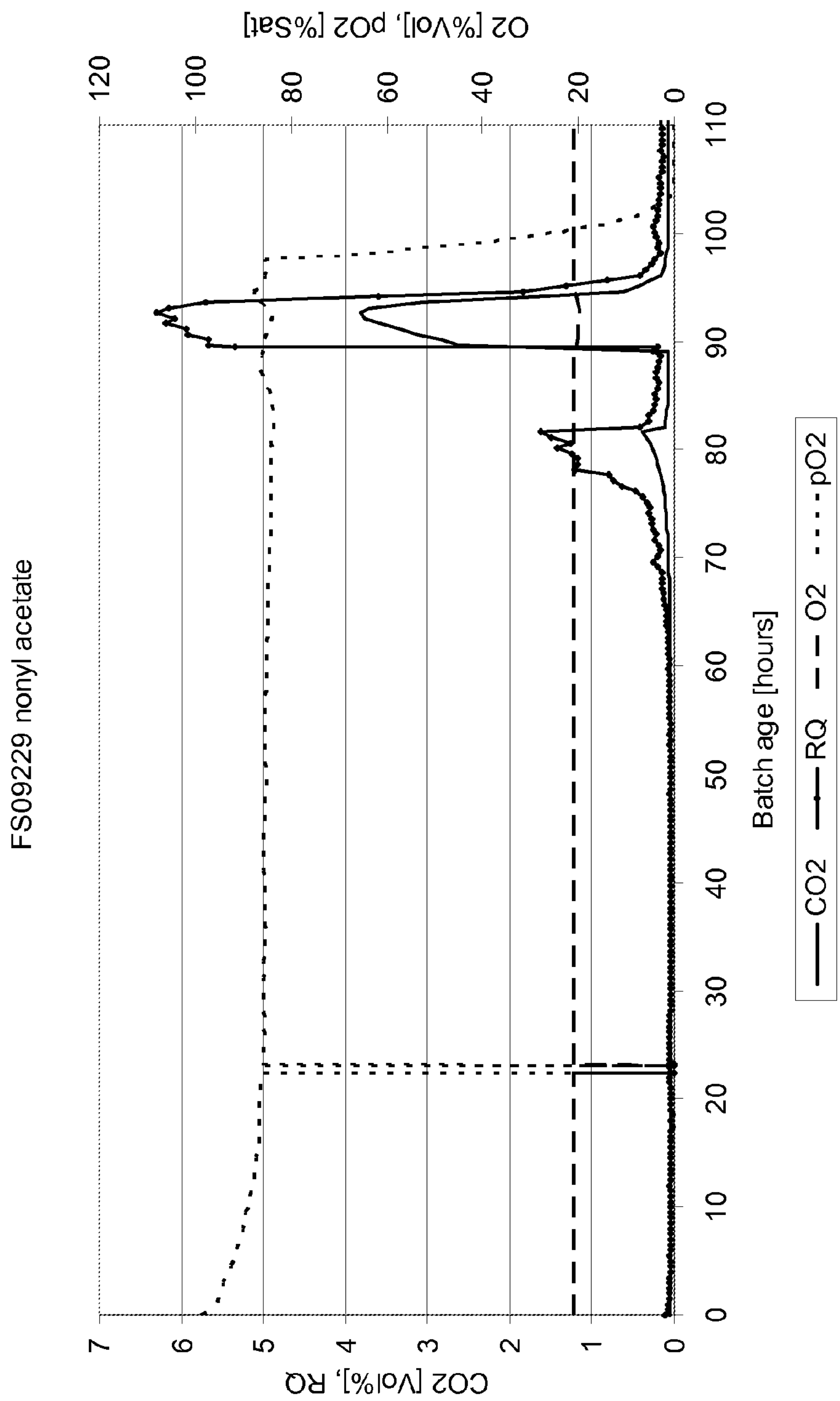
FIG. 10: History plot of parameters of cultivation measured in Example 11.

Determination of Intracellular and Extracellular Levels of Stilbenoids in a Batch Culture of a Non-evolved Strain Containing the Phenylpropanoid Pathway The non-evolved FS09229 strain described in previous examples was grown in the presence of nonyl-acetate. A 1 ml aliquot of a glycerol stock that was made from an exponentional growing FS09229 strain was used to inoculate a fermentor, containing a similar medium as described in the previous example, but now containing 100 g/l glucose and 100 ml of nonyl-acetate from the beginning of the fermentation. The stirrer speed was instantly set at 800 rpm. Upon inoculation of the fermentor, a long lag-phase of approximately 70 hrs set-in, during which an apparent adaptation to the solvent took place. Consumption of glucose only then commenced, indicated by a slow increase in $CO_2$ signal, a decrease in dissolved oxygen and addition of base. Indeed the cells continued to grow exponentially with concomitant production of $CO_2$, and consumed the glucose within less than 25 hours. Based upon the $CO_2$ production the specific growth rate was estimated to be 0.176 1/h (FIG. 10). The final biomass concentration was 15.5 g/l. The cultivation will be referred to as FS09229-solvent. As a control-experiment said strain was grown in the similar medium without the addition of nonyl-acetate. Upon inoculation of the fermentor, consumption of glucose commenced already after approximately 10 hours, indicated by an increase in $CO_2$ signal, a decrease in dissolved oxygen and addition of base. Indeed the cells continued to grow exponentially with concomitant production of $CO_2$, and consumed the glucose within less than 20 hours. Based upon the $CO_2$ production the specific growth rate was estimated to be 0.22 1/h (FIG. 3). The final biomass concentration was 12.8 g/l. The cultivation will be referred to as FS09229-control.

For the determination of stilbenoids, an aliquot of 25 ml of cell broth was collected, and phase separation was initiated by centrifugation at 3500 g for 5 minutes. Both the upper nonylacetate phase and the lower aqueous medium phase were collected separately with a pipette and directly analyzed for their content of stilbenoids and intermediates by HPLC. The total concentration of stilbenoid intermediates that was produced was then calculated by dividing the concentrations in the upper phase with a factor of 10 and then adding them to the concentrations that were observed in the lower phase. The results are shown in the following table:

| | Coumaric acid (mg/l; % total) | Resveratrol (mg/l; % total) | Cinnamic acid (mg/l; % total) | Pinosylvin (mg/l; % total) |
|---|---|---|---|---|
| FS09229-solvent | | | | |
| Upper phase (0.1 L) | — | 160.39; 95.1 | 39.29; 42.2 | 373.24; 100 |
| Lower phase (1 L) | — | 0.83; 4.9 | 53.83; 57.8 | 0.0; 0.0 |
| Total produced in 1 L | — | 16.87; 100 | 9.31; 100 | 37.32 |
| FS09229-control | | | | |
| Supernatant | — | 43.89 | 57.81 | 8.5 |

The results demonstrated that also the non-evolved strain FS09229 was able to grow on a medium that contained 100 ml of nonyl acetate from the beginning with a stirring speed immediately set at 800 rpm. The lag-phase of 70 hours was already considerably longer than the lag-phase of the FS09229-control fermentation, but rather similar to the fermentation with PALCPR-evolved-III strain described in previous examples. The growth rate of 0.176 l/h was only slightly lower then the FS09229-control cultivation, whereas the biomass concentrations were similar.

In both the FS09229-solvent and FS09229-control fermentation, only cinnamic acid, pinosylvin and resveratrol was produced. The solvent mixture was able to capture 95% of the stilbenoid resveratrol, 100% of the stilbenoid pinosylvin and 42% of cinnamic acid. The total amount of resveratrol produced was, however lower than the FS09229-control culture, whereas the cinnamic acid- and pinosylvin concentrations were higher. Said difference in the profile of phenylpropanoid pathway intermediates could be a result of a-non optimal adaptation of the cells to the solvent.

This experiment demonstrates clearly, however, the biocompatibility of nonyl acetate solvent, because non-adapted cells of *S. cerevisiae* are already able to grow on a fermentation medium in the presence of said solvent. For an optimal production of stilbenoids, however, the strain likely needs to be further evolved on said solvent.

Example 12

Adaptation of Microorganisms to the Presence of Solvents

The present example describes a procedure to rapidly improve the resistance of microorganisms towards non-biocompatible toxic solvents a.

Cells of a microorganism are subjected to a train of batch fermentations in a fermentor containing a suitable defined medium. The working volume is 1 L and the gas flow rate is set at 1.5 l/m, the temperature and pH is controlled at a desired setting suitable to the organism. The first fermentation contains a suitable carbon source, preferably in the range of 50 g/l to 100 g/l, and stirring rate is kept low to prevent mixing of the medium- and solvent phase, as illustrated in FIG. 5A in which a fermentor vessel is shown containing the two separated phases (aqueous) and (solvent) agitated by a stirrer below 200 rpm. At the onset of carbon-source consumption, a mixture of solvents is added. The mixture contains 10 ml of solvent (now referred to as "extractant") that is a good extractant for the desired product, but non-biocompatible with the cells, and 40 ml of a biocompatible solvent (now referred to as "biocompatible solvent") that is a poor extractant for the desired product. After depletion of the carbon source the strain is harvested and used for a next fermentation. The next fermentation is performed with said harvested strain using similar fermentation conditions as to the previous one, but now with addition of a mixture of 50 ml extractant and 100 ml biocompatible solvent. In case the cells are able to grow in the presence of said solvent mixture, the strain is harvested after carbon source depletion and used for a next fermentation. The next fermentation is performed with said harvested strain, using similar conditions as to the previous one, but now the stirring rate is increased to 1000 rpm halfway through the consumption of the carbon source, causing mixing of the solvent phase with the medium phase as illustrated in FIG. 5B. In case the cells remain able to grow when the phases are mixed, the strain is harvested and used for a next fermentation. The next fermentation is then performed with said harvested strain using similar conditions as to the previous one, but now with addition of a mixture of 100 ml extractant and 100 ml biocompatible solvent. In case the increase of the extractant to 100 ml causes the arrest of cell growth, indicated by a halt in carbon source consumption, the amount of biocompatible solvent can be increased to, for instance to 200 ml, in order to further obscure the toxic effect of extractant. If necessary the amount of biocompatible solvent can even be increased further up to the point that cells can grow in the presence of the solvent mixture. In case cells are indeed able to grow in the presence of said solvent mixture at high stirring rate, the strain is harvested and stored in a solution of 15% glycerol at −80° C.

In case that the polarity of said solvent mixture is too low to capture sufficient amounts of desired polar products, a further train of fermentations can be initiated to adapt the cells to grow in the presence of solely the more polar and thus more toxic solvent extractant. The cells obtained from the previously described adaptation rounds are taken as starting point because the presence of the solvent mixture should possibly have already evoked adaptation of cells to solvents. For that, the glycerol stocks cells of the cultures described in the previous example is used to inoculate a fermentor, containing the same medium as described in the previous example with a suitable carbon source in the range of 50- to 100 g/l. The cells are allowed to fully consume the carbon source at a stirring speed of 1000 rpm with average dissolved oxygen content of above 70% of saturated air. At the onset of carbon source consumption, the stirring rate is turned down to 300 rpm, after which slowly 100 ml of extractant is added.

Upon addition of extractant, consumption of carbon source is arrested, the dissolved oxygen content increases to almost 99% of saturated air, $O_2$— consumption and $CO_2$ production halts, all indicating that the proliferation of cells arrested. However after a long lag-phase, the $CO_2$ signal slowly increases, dissolved oxygen slowly decreases, indicating that cells start to grow, and consumption of carbon source commences again.

To further improve said strain in terms of reducing the length of the lag-phase and growth rate, a 25 ml aliquot of the exponentional growing strain as described above is used to inoculate a fermentor, containing a similar medium as described previously. However, the medium now contains 100 ml of extractant from the very beginning of the fermentation. In addition, the stirrer speed is instantly set at 800 rpm. Upon inoculation of the fermentor, consumption of the carbon source commences after a shorter lag-phase than before. To further improve said strain in terms of both length of lag-phase and growth rate, another adaption round follows with a 50 ml aliquot of the exponentional growing adapted-strain, in the presence of 100 ml of extractant and with the stirring rate instantly set at 800 rpm. The number of adaptation rounds is repeated until a satisfactory reduction of lag-phase, and sufficiently high growth-rates are reached.

Example 13

Determination of Intracellular and Extracellular Levels of Stilbenoids in Shakeflask Cultures of FS06112, in the Presence of the Solvent Octyl Acetate A glycerol stock of strain FS06112 was used to inoculate 500 ml baffled shake flasks that contained 100 ml modified M9 medium consisting of 4.5 g/l glycerol, 1.5 g/l yeast extract, 3 g/l $K_2HPO_4$, 6.8 g/l $Na_2HPO_4$, 0.5 g/l NaCl, 1 g/l $NH_4C$, 50 μg/ml ampicillin and 50 μg/ml kanamycin; the initial pH was set at 7.0. The shakeflasks were incubated at ambient temperature, and were mixed with a magnetic stirring bar at approximately 150 rpm. After 5 hours, isopropyl β-thiogalactopyranoside (IPTG) was added at a final concentration of 4 mM, as an inducer of the T7 promoter that was in front of each of the three genes TAL, 4CL and VST. After one hour an aliquot of 10 ml of the solvent octyl acetate was added to one shakeflask that is now referred to as FS06112-solvent; the shakeflask culture without solvent will be referred to as FS06112-control. After an incubation period of approximately 24 hours, 2.5 g/l glycerol was consumed in both the FS06112-solvent and -control culture and both the medium and solvent phases were analyzed for the presence of resveratrol.

For the determination of stilbenoids, an aliquot of 50 ml of cell broth was collected, and phase separation was initiated by centrifugation at 4500 g for 10 minutes. Both the upper methyl decanoate phase and the lower aqueous medium phase were collected separately with a pipette and directly analyzed for their content of stilbenoids and intermediates by HPLC. The total concentration of stilbenoid intermediates that was produced was then calculated by dividing the concentrations in the upper phase with a factor of 10 and then adding them to the concentrations that were observed in the lower phase. The results are shown in the following table:

| Solvent: octyl acetate | Coumaric acid (mg/l; % total) | Resveratrol (mg/l; % total) | Cinnamic acid (mg/l; % total) | Pinosylvin (mg/l; % total) |
|---|---|---|---|---|
| FS06112-solvent | | | | |
| Upper phase (0.1 L) | — | 3.03; 100 | — | — |
| Lower phase (1 L) | — | 0.0; 0.0 | — | — |
| Total produced in 1 L | — | 0.30; 100 | — | — |
| FS06112-control | | | | |
| Supernatant | — | 0.85 | — | — |

The results demonstrated that strain FS06112 was able to grow in a shakeflask on a medium to which 10 ml of octyl acetate was added at the onset of induction of resveratrol production. Both FS06112-solvent- and FS06112-control cultivation consumed 2.5 g/l of glycerol within 24 hrs.

In both the FS06112-control and FS06112-solvent cultivation, resveratrol was produced without co-production of any of the other pathway intermediates coumaric acid and pinosylvin. The solvent was able to capture 100% of the stilbenoid resveratrol, but the total amount of resveratrol produced was lower than the FS06112-control cultivation.

Example 14

Construction *E. coli* Strain FS06112, Containing the "TAL"-Phenylpropanoid Pathway with Inducible Promoters I) Construction of a Bacterial Vector for Expression of TAL in *Escherichia coli.*

An ammonia lyase from *Rhodobacter capsulatus*, which was codon-optimized for use in *S. cerevisiae*, was used as the basis for the construction of a bacterial vector for expression of TAL in *Escherichia coli*. The coding sequence of tyrosine ammonia lyase (TAL) from *Rhodobacter capsulatus* (Kyndt et al., 2002; SEQ ID NO: 73 (nucleotide) and 74 (amino acid)) was codon optimized for expression in *S. cerevisiae* using the online service back translation tool at www.entelechon.com, yielding sequence SEQ ID NO: 75, which again expresses SEQ ID NO: 74. Oligos for the synthetic gene assembly were constructed at MWG Biotech and the synthetic gene was assembled by PCR using a slightly modified method protocol of from Martin et al. (2003). The amplified synthetic TAL gene was digested with EcoR1/Spe1 and ligated into EcoR1/Spe1-digested pESC-URA vector. The resulting plasmid, pESC-URA-TAL, contained the gene encoding for TAL under the control of the divergent GAL1/GAL10 promoter. The sequence was verified by sequencing of two different clones of pESC-URA-TAL. The gene encoding tyrosine ammonia lyase (TAL) was reamplified by PCR from the yeast plasmid pESC-URA-TAL described in using the forward primer 5'-CCG CTCGAG CGG ATG ACC CTG CAA TCT CAA ACA GCT AAA G-3' SEQ ID NO: 76 and the reverse primer 5'-GC GGATCC TTA AGC AGG TGG ATC GGC AGC T-3' SEQ ID NO: 77 with 5' overhangs containing the restriction sites XhoI and BamHI, respectively. The introduction of restriction sites at the 5' and 3' ends of the gene allowed ligation of the restricted PCR product into a pET-16b vector (Novagen), digested with XhoI and BamHI to yield pET16b-TAL. The pET-16b vector contained both the gene for ampicillin resistance and the T7 promoter. Hence, above procedure resulted in a vector that contained the gene encoding TAL under the control of the T7 promoter. The sequence of the gene encoding TAL was verified by sequencing of one clone of pET16b-TAL.

II) Construction of a Bacterial Vector for Expression of 4CL and VST in *Escherichia coli.*

The gene encoding 4-Coumarate-CoA ligase (4CL1) was reamplified by PCR from the yeast plasmid pESC-TRP-4CL1-VST1 using the forward primer 5'-TG CCATGG CA ATGGCGCCAC AAGAACAAGC AGTTT-3' SEQ ID NO: 78 and the reverse primer 5'-GC GGATCC CCT TCA CAA TCC ATT TGC TAG TTT TGCC-3' SEQ ID NO: 79 with 5' overhangs containing the restriction sites NcoI and BamHI, respectively. The introduction of restriction sites at the 5' and 3' ends of the gene allowed ligation of the restricted PCR product into a pET16b vector (Novagen) digested with NcoI and BamHI. The resulting plasmid, pET16b-4CL1, contained the gene encoding for 4CL1 under the control of the T7 promoter. Both the T7 promoter and the gene encoding 4CL1 were reamplified as one fragment by PCR from the plasmid pET16b-4CL1 using the forward primer (A) 5'-GA-CAAGCTTGCGGCC AGA TCT CGA TCC CGC GAA ATT AAT ACG-3' SEQ ID NO: 80 and the reverse primer (B) 5'-TGCTCGAGTGCGGCC TCA CAA TCC ATT TGC TAG TTT TGCC-3' SEQ ID NO: 81. The 4CL1 gene was inserted into a pET26b-VST1 vector (Novagen) digested with Not1 using the In-fusion™ PCR cloning Technology (Clontech, Mountain View, Calif.) to yield pET26b-VST1-4CL1. The resulting plasmid, pET26b-VST1-4CL1, contained the two genes 4CL1 and VST1 that each are under control of an individual T7 promoter. The sequences of the genes, promoters and terminator were verified by sequencing of four clones of pET26b-VST1-4CL1.

The gene encoding grape resveratrol synthase (VST1) was reamplified by PCR from the yeast plasmid pESC-TRP-4CL1-VST1, using the forward primer 5'-CGC CATATG ATG GCA TCC GTA GAG GAG TTC AGA A-3' SEQ ID NO: 82 and the reverse primer 5'-CC GGATCC TCA TTA GTT AGT GAC AGT TGG AAC AGA GT-3' SEQ ID NO: 83. The VST1 gene was inserted into a pET26b vector (Novagen) digested with Nde1 and BamH1 using the In-fusion™ PCR cloning Technology (Clontech, Mountain View, Calif.) to yield pET26b-VST1. The pET26b vector contained both the gene for kanamycin resistance and the T7 promoter. Hence, above procedure resulted in a vector that contained the gene encoding VST1 under the control of the T7 promoter. Cloning between the Nde1 and Bamh1 restriction sites enabled the removal of N-terminal pET26b pelB secretion signal sequence, which would otherwise enable targeting of the expressed protein to the *E. coli* periplasmic space. An extra VST1 copy was cloned into a third vector encoding chloramphenicol resistance by reamplifying VST1 gene by PCR from the yeast plasmid pESCTRP-4CL1-VST1, using the forward primer 5'-AAGGAGATATACATATG ATG GCA TCC GTA GAG GAG TTC AGA A-3' SEQ ID NO: 84 and the reverse primer 5'-CTTTACCAGACTC GAG TCA TTA GTT AGT GAC AGT TGG AAC AGA GT-3' SEQ ID NO: 85. The VST1 gene was inserted into a pACYCDuet-1 vector (Novagen)

digested with Nde1 and Xho1 using the In-fusion™ PCR cloning Technology (Clontech, Mountain View, Calif.) to yield pACYCDuet-VST1.

III) Expression of the Pathway to Resveratrol in *Escherichia coli*, Using TAL, 4CL and VST.

The transformation of the bacterial cell was conducted in accordance with methods known in the art, for instance, by using competent cells or by electroporation (see, e.g., Sambrook et al., 1989). The *E. coli* strain BL21 (DE3) (Novagen) was co-transformed with the three vectors pET16b-TAL, pET26b-VST-4CL, and pACYCDuet-VST1. Transformants were selected on Luria-Bertani (LB) medium with 50 mg/l ampicillin, 50 mg/l kanamycin and 50 mg/l chloramphenicol. This resulted in a strain harboring three plasmids pET16b-TAL, pET26b-VST-4CL, and pACYCDuet-VST1 with the full "TAL"-resveratrol pathway and double VST1 copies (FS06111). It was originally thought, before extraction procedures had been optimized, that an extra copy of VST1 gene was needed on a third plasmid for efficient expression of the resveratrol pathway. However, after optimization of extraction procedures, it was demonstrated that a strain harbouring only the two plasmids pET16-TAL and pET26-4CL1-VST1, performed as well as the three-plasmid strain with the extra VST1 copy (FS06111). The strain expressing the resveratrol pathway with two plasmids (FS06112), therefore, was obtained by restreaking FS06111 on LB agar plates, containing only 50 mg/l ampicillin and 50 mg/l kanamycin, but lacking chloramphenicol; with no selection pressure from chloramphenicol, the third plasmid was eventually lost.

Example 15

Determination of Intracellular and Extracellular Levels of Stilbenoids in Shakeflask Cultures of FS06112, in the Presence of the Solvent Methyl-decanoate A glycerol stock of strain FS06112 was used to inoculate 500 ml baffled shake flasks that contained 100 ml modified M9 medium consisting of 4.5 g/l glycerol, 1.5 g/l yeast extract, 3 g/l $K_2HPO_4$, 6.8 g/l $Na_2HPO_4$, 0.5 g/l NaCl, 1 g/l $NH_4C$, 50 μg/ml ampicillin and 50 μg/ml kanamycin; the initial pH was set at 7.0. The shakeflasks were incubated at ambient temperature, and were mixed with a magnetic stirring bar at approximately 150 rpm. After 5 hours, isopropyl β-thiogalactopyranoside(IPTG) was added at a final concentration of 4 mM, as an inducer of the T7 promoter that was in front of each of the three genes TAL, 4CL and VST. After one hour an aliquot of 10 ml of the solvent methyl decanoate was added to one shakeflask that is now referred to as FS06112-solvent; the shakeflask culture without solvent will be referred to as FS06112-control. After an incubation period of approximately 48 hours, the glycerol was depleted and the medium and solvent phases were analyzed for the presence of resveratrol.

For the determination of stilbenoids, an aliquot of 50 ml of cell broth was collected, and phase separation was initiated by centrifugation at 4500 g for 10 minutes. Both the upper methyl decanoate phase and the lower aqueous medium phase were collected separately with a pipette and directly analyzed for their content of stilbenoids and intermediates by HPLC. The total concentration of stilbenoid intermediates that was produced was then calculated by dividing the concentrations in the upper phase with a factor of 10 and then adding them to the concentrations that were observed in the lower phase. The results are shown in the following table:

| Solvent: methyl decanoate | Coumaric acid (mg/l; % total) | Resveratrol (mg/l; % total) | Cinnamic acid (mg/l; % total) | Pinosylvin (mg/l; % total) |
|---|---|---|---|---|
| FS06112-solvent | | | | |
| Upper phase (0.1 L) | — | 8.79; 100 | — | — |
| Lower phase (1 L) | — | 0.0; 0.0 | — | — |
| Total produced in 1 L | — | 0.88; 100 | — | — |
| FS06112-control | | | | |
| Supernatant | — | 1.08 | — | — |

The results demonstrated that strain FS06112 was able to grow in a shakeflask on a medium that to which 10 ml of methyl-decanoate was added at the onset of induction of resveratrol production. The FS06112-solvent cultivation consumed the glycerol within 48 hrs, which was only slightly longer than the 30 hours in which the FS06112-control cultivation consumed the glycerol.

In both the FS06112-control and FS06112-solvent cultivation, resveratrol was produced without co-production of any of the other pathway intermediates coumaric acid and pinosylvin. In addition, in the chromatogram of the upper-solvent phase of the FS06112-solvent cultivation a small peak could be observed with a retention time and UV-spectrum that resembled those of cis-resveratrol. Most likely, a small fraction of the produced trans-resveratrol was converted into cis-resveratrol, which could be an effect of the presence of the solvent. The solvent was able to capture 100% of the stilbenoid resveratrol, and the total amount of resveratrol produced was slightly lower than the FS06112-control cultivation. However, the small peak that allegedly represented cis-resveratrol was approximately 25% of the area of the trans-resveratrol peak, which implied that the total resveratrol content produced in the FS06112-solvent cultivation could be equal or even slightly higher than in the FS06112-control cultivation.

Example 16

Determination of Intracellular and Extracellular Levels of Stilbenoids in Shakeflask Cultures of FS06112, in the Presence of the Solvent Undecanone A glycerol stock of strain FS06112 was used to inoculate 500 ml baffled shake flasks that contained 100 ml modified M9 medium consisting of 4.5 g/l glycerol, 1.5 g/l yeast extract, 3 g/l $K_2HPO_4$, 6.8 g/l $Na_2HPO_4$, 0.5 g/l NaCl, 1 g/l $NH_4C$, 50 μg/ml ampicillin and 50 μg/ml kanamycin; the initial pH was set at 7.0. The shakeflasks were incubated at ambient temperature, and were mixed with a magnetic stirring bar at approximately 150 rpm. After 5 hours, isopropyl β-thiogalactopyranoside (IPTG) was added at a final concentration of 4 mM, as an inducer of the T7 promoter that was in front of each of the three genes TAL, 4CL and VST. After one hour an aliquot of 10 ml of the solvent undecanone was added to one shakeflask that is now referred to as FS06112-solvent; the shakeflask culture without solvent will be referred to as FS06112-control. After an incubation period of approximately 48 hours, the glycerol was depleted and the medium and solvent phases were analyzed for the presence of resveratrol.

For the determination of stilbenoids, an aliquot of 50 ml of cell broth was collected, and phase separation was initiated by centrifugation at 4500 g for 10 minutes. Both the upper undecanone phase and the lower aqueous medium phase were collected separately with a pipette and directly analyzed for their content of stilbenoids and intermediates by HPLC. The total concentration of stilbenoid intermediates that was produced was then calculated by dividing the concentrations in the upper phase with a factor of 10 and then adding them to the concentrations that were observed in the lower phase. The results are shown in the following table:

| Solvent: Undecanone | Coumaric acid (mg/l; % total) | Resveratrol (mg/l; % total) | Cinnamic acid (mg/l; % total) | Pinosylvin (mg/l; % total) |
|---|---|---|---|---|
| FS06112-solvent | | | | |
| Upper phase (0.1 L) | — | 8.82; 100 | — | — |
| Lower phase (1 L) | — | 0.0; 0.0 | — | — |
| Total produced in 1 L | — | 0.88; 100 | — | — |
| FS06112-control | | | | |
| Supernatant | — | 1.08 | — | — |

The results demonstrated that strain FS06112 was able to grow in a shakeflask on a medium that to which 10 ml of undecanone was added at the onset of induction of resveratrol production. The FS06112-solvent cultivation consumed the glycerol within 48 hrs, which was only slightly longer than the 30 hours in which the FS06112-control cultivation consumed the glycerol.

In both the FS06112-control and FS06112-solvent cultivation, resveratrol was produced without co-production of any of the other pathway intermediates coumaric acid and pinosylvin. In addition, the determination of the resveratrol content in the solvent phase was sometimes complicated by a considerable shift in retention time of the resveratrol peak. Most likely the high concentration of undecanone in the sample interfered with the a-polar interactions between the resveratrol molecule and the stationary phase. Apparently undecanone interfered more intensively with the analysis than all the other solvents used in the previous examples because no drastic retention times shifts have been observed with said other solvents. Still it was possible to render a quantitative analysis and to establish that undecanone was able to capture 100% of the stilbenoid resveratrol, and that the total amount of resveratrol produced was slightly lower than the FS06112-control cultivation. However, with the uncertainty of the retention time shift and its effect on the peak shape the total resveratrol content produced in the FS06112-solvent cultivation could be considered at least equal to that of the FS06112-control cultivation.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

References:

Abe, I., Watanabe, T. and Noguchi, H. (2004).

Enzymatic Formation of Long-chain Polyketide Pyrones by Plant Type III Polyketide Synthases.

Phytochemistry, 65, 2447-2453

Cochrane F C, Davin L B, Lewis N G.

The *Arabidopsis* phenylalanine ammonia lyase gene family: kinetic characterization of the four PAL isoforms. Phytochemistry. 2004:65:1557-64.

Ehlting J, Büttner D, Wang Q, Douglas C J, Somssich I E, Kombrink E.

Three 4-coumarate:coenzyme A ligases in *Arabidopsis thaliana* represent two evolutionarily divergent classes in angiosperms. Plant J. 1999:19:9-20.

Guerra O G, Rubio I G, da Silva Filho C G, Bertoni R A, Dos Santos Govea R C, Vicente E J. (2006). A novel system of genetic transformation allows multiple integrations of a desired gene in *Saccharomyces cerevisiae* chromosomes. J Microbiol Methods. 67, 437-45.

Hain, R., Reif, H. J., Krause, E., Langebartels, R., Kindl, H., Vornam, B., Wiese, W., Schmelzer, E., Schreier, P. H., Stocker, R. H. and Stenzel, K. (1993). Disease resistance results from foreign phytoalexin expression in a novel plant. Nature 361, 153-156.

Hamberger B, Hahlbrock K.

The 4-coumarate:CoA ligase gene family in *Arabidopsis thaliana* comprises one rare, sinapate-activating and three commonly occurring isoenzymes. Proc Natl Acad Sci USA. 2004:101:2209-14.

Kaneko, M., Ohnishi, Y. and Horinouchi, S. Cinnamate:Coenzyme (2003). A ligase from the Filamentous Bacteria *Streptomyces coelicolor* A3(2), J. Bact. 185, 20-27.

Kyndt J A, Meyer T E, Cusanovich M A, Van Beeumen J J. (2002). Characterization of a bacterial tyrosine ammonia lyase, a biosynthetic enzyme for the photoactive yellow protein. FEBS Lett. 512, 240-244.

Martin, V. J. J., Pitera, D. J., Withers, S. T., Newman, J. D. and Keasling, J. D. (2003). Engineering a mevalonate pathway in *Escherichia coli* for production of terpenoids. Nature biotechnology 21, 796-802.

Morita, H., Noguchi, H., Schroder, J. and Abe, I. (2001). Novel polyketides synthesized with a higher plant stilbene synthase. Eur. J. Biochem. 268, 3759-3766.

Mumberg D, Müller R, Funk M.

Yeast vectors for the controlled expression of heterologous proteins in different genetic backgrounds. Gene. 1995:156: 119-22.

Sambrook, J., Fritsch, E. F. and Maniatis, T. (1989). Molecular Cloning, A Laboratory Manual, 2d edition, Cold Spring Harbor, N.Y.

Samappito, S., Page, J. E., Schmidt, J., De-Eknamkul, W. and Kutchan, T. M. (2003). Aromatic and pyrone polyketides synthesized by a stilbene synthase from *Rheum tataricum*. Phytochemistry 62, 313-323.

Sikorski R S, Hieter P.

A system of shuttle vectors and yeast host strains designed for efficient manipulation of DNA in *Saccharomyces cerevisiae*. Genetics. 1989:122:19-27.

Stark D et al, 2003, Biotechnology and Bioengineering; August 20, 83(4): 376-75.

Tilburn J, Scazzocchio C, Taylor G G, Zabicky-Zissman J H, Lockington R A, Davies R W. (1983). Transformation by integration in *Aspergillus nidulans*. Gene. 26, 205-21.

Verduyn C, Postma E, Scheffers W A, Van Dijken J P. (1992). Effect of benzoic acid on metabolic fluxes in yeasts: a continuous-culture study on the regulation of respiration and alcoholic fermentation. Yeast. 8, 501-517.

The invention claimed is:

1. A method for the production of a cis- or trans-stilbenoid of the general formula 1:

Formula 1

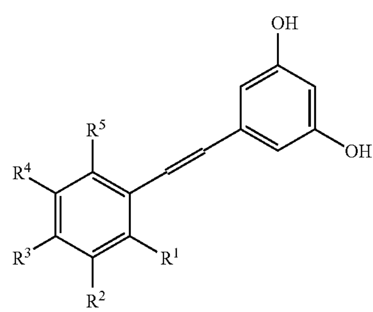

in which each or $R^1R^2$, $R^3$, $R^4$ and $R^5$ independently is hydrogen or hydroxyl, or a glycosylated or oligomeric form thereof, comprising cultivating a micro-organism producing said stilbenoid, wherein said cultivation is performed in a multi-phase system comprising an aqueous first phase containing said micro-organism and a second phase immiscible with said aqueous phase in which said stilbenoid accumulates, wherein said second phase comprises an ester, and said ester is of the general formula $R^6$—COO—$R^7$, and $R^6$ is H or an aliphatic straight or branched chain hydrocarbon moiety of from 1-6 carbon atoms and $R^7$ is an aliphatic straight or branched chain hydrocarbon moiety of from 2-16 carbon atoms, or a heteroatom containing hydrocarbon moiety of from 2to 16 carbon atoms or an aromatic or heteroaromatic moiety of from 5 to 16 carbon atoms.

2. The method as claimed in claim 1, wherein $R^7$ has from 3 to 9 carbon atoms.

3. The method as claimed in claim 1, wherein $R^6$ has from 1 to 4 carbon atoms.

4. The method as claimed in claim 1, wherein said ester is an octyl acetate.

5. The method as claimed in claim 1, wherein said second phase is a liquid comprising an alkane.

6. The method as claimed in claim 5, wherein said alkane is a $C_6$ to $C_{16}$ straight or branched chain alkane.

7. The method as claimed in claim 6, wherein said alkane is n-dodecane.

* * * * *

SEQUENCE LISTING

```
<160> NUMBER OF SEQ ID NOS: 85

<210> SEQ ID NO 1
<211> LENGTH: 25
<212> TYPE: DNA
<213> ORGANISM: Saccharomyces cerevisiae

<400> SEQUENCE: 1

gtattctata tccacgcctg caaac                                          25


<210> SEQ ID NO 2
<211> LENGTH: 45
<212> TYPE: DNA
<213> ORGANISM: Saccharomyces cerevisiae

<400> SEQUENCE: 2

agtacataca gggaacgtcc ctacaggaac gcaaacttaa gctac                    45


<210> SEQ ID NO 3
<211> LENGTH: 50
<212> TYPE: DNA
<213> ORGANISM: Saccharomyces cerevisiae

<400> SEQUENCE: 3

gcatacaatc aactatctca tatacaatgc cgtttggaat agacaacacc               50


<210> SEQ ID NO 4
<211> LENGTH: 28
<212> TYPE: DNA
<213> ORGANISM: Saccharomyces cerevisiae

<400> SEQUENCE: 4

gcttccgcat tacaaataaa gtcttcaa                                       28


<210> SEQ ID NO 5
<211> LENGTH: 42
<212> TYPE: DNA
<213> ORGANISM: Saccharomyces cerevisiae

<400> SEQUENCE: 5

ggacgttccc tgtatgtact agggggatcg aagaaatgat gg                       42


<210> SEQ ID NO 6
<211> LENGTH: 25
<212> TYPE: DNA
<213> ORGANISM: Saccharomyces cerevisiae

<400> SEQUENCE: 6

gagcaatgaa cccaataacg aaatc                                          25
```

<210> SEQ ID NO 7
<211> LENGTH: 25
<212> TYPE: DNA
<213> ORGANISM: Saccharomyces cerevisiae

<400> SEQUENCE: 7
cttgacgttc gttcgactga tgagc 25

<210> SEQ ID NO 8
<211> LENGTH: 26
<212> TYPE: DNA
<213> ORGANISM: Saccharomyces cerevisiae

<400> SEQUENCE: 8
tgtatatgag atagttgatt gtatgc 26

<210> SEQ ID NO 9
<211> LENGTH: 40
<212> TYPE: DNA
<213> ORGANISM: Arabidopsis thaliana

<400> SEQUENCE: 9
gcgaattctt atgacgacac aagatgtgat agtcaatgat 40

<210> SEQ ID NO 10
<211> LENGTH: 42
<212> TYPE: DNA
<213> ORGANISM: Arabidopsis thaliana

<400> SEQUENCE: 10
gcactagtat cctagttcat taatccattt gctagtcttg ct 42

<210> SEQ ID NO 11
<211> LENGTH: 32
<212> TYPE: DNA
<213> ORGANISM: Aspergillus nidulans

<400> SEQUENCE: 11
cggaattcat acgcggtttt ttggggtagt ca 32

<210> SEQ ID NO 12
<211> LENGTH: 32
<212> TYPE: DNA
<213> ORGANISM: Aspergillus nidulans

<400> SEQUENCE: 12
cgcccgggta tgccacctac agccattgcg aa 32

<210> SEQ ID NO 13
<211> LENGTH: 32
<212> TYPE: DNA
<213> ORGANISM: Aspergillus nidulans

<400> SEQUENCE: 13
gcggatccat agggcgctta cacagtacac ga 32

<210> SEQ ID NO 14
<211> LENGTH: 48
<212> TYPE: DNA
<213> ORGANISM: Aspergillus nidulans

<400> SEQUENCE: 14
cggagagggc gcgcccgtgg cggccgcgga tccacttaac gttactga 48

<210> SEQ ID NO 15
<211> LENGTH: 48
<212> TYPE: DNA
<213> ORGANISM: Aspergillus nidulans

<400> SEQUENCE: 15
gcggccgcca cgggcgcgcc ctctccggcg gtagtgatgt ctgctcaa 48

<210> SEQ ID NO 16
<211> LENGTH: 32
<212> TYPE: DNA
<213> ORGANISM: Aspergillus nidulans

<400> SEQUENCE: 16
cgaagcttta taattccctt gtatctctac ac 32

<210> SEQ ID NO 17
<211> LENGTH: 32
<212> TYPE: DNA
<213> ORGANISM: Arabidopsis thaliana

<400> SEQUENCE: 17
cggcgcgcat aatggacctc ctcttgctgg ag 32

<210> SEQ ID NO 18
<211> LENGTH: 38
<212> TYPE: DNA
<213> ORGANISM: Arabidopsis thaliana

<400> SEQUENCE: 18
gggcggccgc ttattaacag ttccttggtt tcataacg 38

<210> SEQ ID NO 19
<211> LENGTH: 56
<212> TYPE: DNA
<213> ORGANISM: Aspergillus fumigatus

<400> SEQUENCE: 19
cgtgtacaat attaattaac gagagcgatc gcaataaccg tattaccgcc tttgag 56

<210> SEQ ID NO 20
<211> LENGTH: 32
<212> TYPE: DNA
<213> ORGANISM: Aspergillus fumigatus

<400> SEQUENCE: 20
cgacatgtat tcccgggaag atctcatggt ca 32

<210> SEQ ID NO 21
<211> LENGTH: 35
<212> TYPE: DNA
<213> ORGANISM: Arabidopsis thaliana

<400> SEQUENCE: 21
gcggagaggg cgcgatggcg ccacaagaac aagca 35

<210> SEQ ID NO 22
<211> LENGTH: 39
<212> TYPE: DNA
<213> ORGANISM: Arabidopsis thaliana

<400> SEQUENCE: 22
tggatccgcg gccgctcaca atccatttgc tagttttgc 39

<210> SEQ ID NO 23
<211> LENGTH: 32
<212> TYPE: DNA
<213> ORGANISM: Vitis vinifera

<400> SEQUENCE: 23
cggcgcgcat aatggcatcc gtagaggagt tc 32

<210> SEQ ID NO 24
<211> LENGTH: 36
<212> TYPE: DNA
<213> ORGANISM: Vitis vinifera

<400> SEQUENCE: 24
gggcggccgc ttatcattag ttagtgacag ttggaa 36

<210> SEQ ID NO 25
<211> LENGTH: 1671
<212> TYPE: DNA
<213> ORGANISM: Arabidopsis thaliana

<400> SEQUENCE: 25
atgacgacac aagatgtgat agtcaatgat cagaatgatc agaaacagtg tagtaatgac 60
gtcattttcc gatcgagatt gcctgatata tacatcccta accacctccc actccacgac 120
tacatcttcg aaaatatctc agagttcgcc gctaagccat gcttgatcaa cggtcccacc 180
ggcgaagtat acacctacgc cgatgtccac gtaacatctc ggaaactcgc cgccggtctt 240
cataacctcg gcgtgaagca acacgacgtt gtaatgatcc tcctcccgaa ctctcctgaa 300
gtagtcctca ctttccttgc cgcctccttc atcggcgcaa tcaccacctc cgcgaacccg 360
ttcttcactc cggcggagat ttctaaacaa gccaaagcct ccgcggcgaa actcatcgtc 420
actcaatccc gttacgtcga taaaatcaag aacctccaaa acgacggcgt tttgatcgtc 480
accaccgact ccgacgccat ccccgaaaac tgcctccgtt tctccgagtt aactcagtcc 540
gaagaaccac gagtggactc aataccggag aagatttcgc cagaagacgt cgtggcgctt 600
cctttctcat ccggcacgac gggtctcccc aaaggagtga tgctaacaca caaaggtcta 660
gtcacgagcg tggcgcagca agtcgacggc gagaatccga atctttactt caacagagac 720
gacgtgatcc tctgtgtctt gcctatgttc catatatacg ctctcaactc catcatgctc 780
tgtagtctca gagttggtgc cacgatcttg ataatgccta agttcgaaat cactctcttg 840
ttagagcaga tacaaaggtg taaagtcacg gtggctatgg tcgtgccacc gatcgtttta 900
gctatcgcga agtcgccgga gacggagaag tatgatctga gctcggttag gatggttaag 960
tctggagcag ctcctcttgg taaggagctt gaagatgcta ttagtgctaa gtttcctaac 1020
gccaagcttg gtcagggcta tgggatgaca gaagcaggtc cggtgctagc aatgtcgtta 1080
gggtttgcta aagagccgtt tccagtgaag tcaggagcat gtggtacggt ggtgaggaac 1140
gccgagatga agatacttga tccagacaca ggagattctt tgcctaggaa caaacccggc 1200
gaaatatgca tccgtggcaa ccaaatcatg aaaggctatc tcaatgaccc cttggccacg 1260
gcatcgacga tcgataaaga tggttggctt cacactggag acgtcggatt tatcgatgat 1320
gacgacgagc ttttcattgt ggatagattg aaagaactca tcaagtacaa aggatttcaa 1380
gtggctccag ctgagctaga gtctctcctc ataggtcatc cagaaatcaa tgatgttgct 1440
gtcgtcgcca tgaaggaaga agatgctggt gaggttcctg ttgcgtttgt ggtgagatcg 1500
aaagattcaa atatatccga agatgaaatc aagcaattcg tgtcaaaaca ggttgtgttt 1560
tataagagaa tcaacaaagt gttcttcact gactctattc ctaaagctcc atcagggaag 1620
atattgagga aggatctaag agcaagacta gcaaatggat taatgaacta g 1671

<210> SEQ ID NO 26
<211> LENGTH: 2154
<212> TYPE: DNA
<213> ORGANISM: Artificial Sequence
<220> FEATURE:
<223> OTHER INFORMATION: Synthetic A.thaliana gene, codon optimised for S.cerevisiae expression

<400> SEQUENCE: 26
atggaccaaa ttgaagcaat gctatgcggt ggtggtgaaa agaccaaggt ggccgtaacg 60
acaaaaactc ttgcagatcc tttgaattgg ggtctggcag ctgaccagat gaaaggtagc 120
catctggatg aagttaagaa gatggttgag gaatacagaa gaccagtcgt aaatctaggc 180
ggcgagacat tgacgatagg acaggtagct gctatttcga ccgttggcgg ttcagtgaag 240
gtagaacttg cagaaacaag tagagccgga gttaaggctt catcagattg ggtcatggaa 300
agtatgaaca agggcacaga ttcctatggc gttaccacag gctttggtgc tacctctcat 360
agaagaacta aaaatggcac tgctttgcaa acagaactga tcagattcct taacgccggt 420
attttcggta atacaaagga aacttgccat acattacccc aatcggcaac aagagctgct 480
atgcttgtta gggtgaacac tttgttgcaa ggttactctg gaataaggtt tgaaattctt 540
gaggccatca cttcactatt gaaccacaac atttctcctt cgttgccctt aagaggaaca 600
ataactgcca gcggtgattt ggttcccctt tcatatatcg caggcttatt aacgggaaga 660
cctaattcaa aggccactgg tccagacgga gaatccttaa ccgctaagga agcatttgag 720
aaagctggta tttcaactgg tttctttgat ttgcaaccca aggaaggttt agccctggtg 780
aatggcaccg ctgtcggcag cggtatggca tccatggtgt tgtttgaagc taacgtacaa 840
gcagttttgg ccgaagtttt gtccgcaatt tttgccgaag tcatgagtgg aaaacctgag 900
tttactgatc acttgaccca caggttaaaa catcacccag gacaaattga agcagcagct 960
atcatggagc acattttgga cggctctagc tacatgaagt tagcccagaa ggttcatgaa 1020
atggaccctt tgcaaaaacc caaacaagat agatatgctt taaggacatc cccacaatgg 1080
cttggccctc aaattgaagt aattagacaa gctacaaagt ctatagaaag agagatcaac 1140
tctgttaacg ataatccact tattgatgtg tcgaggaata aggcaataca tggaggcaat 1200
ttccagggta cacccatagg agtcagtatg gataatacca ggcttgccat agccgcaatt 1260
ggcaaattaa tgtttgccca attttctgaa ttggtcaatg acttctacaa taacggtttg 1320
ccttcgaatc tgaccgcatc ttctaaccct agtcttgatt atggtttcaa aggtgctgag 1380
atagcaatgg caagctattg ttcagagctg caatatctag ccaacccagt aacctctcat 1440
gtacaatcag ccgaacaaca caatcaggat gttaattctt tgggcctgat ttcatcaaga 1500
aaaacaagcg aggccgttga tatccttaaa ttaatgtcca caacattttt agtgggtata 1560
tgccaggccg tagatttgag acacttggaa gagaatttga gacagacagt gaaaaatacc 1620
gtatcacagg ttgcaaaaaa ggttctaact acaggtatca atggtgaatt gcacccatca 1680
agattctgtg aaaaagattt attaaaagtt gtagatagag aacaagtatt tacttacgtt 1740
gacgatccat gtagcgctac ttatccattg atgcagagat tgagacaagt tattgtagat 1800
cacgctttat ccaatggtga aactgagaaa aatgccgtta cttcaatatt ccaaaagata 1860
ggtgcctttg aagaagaact gaaggcagtt ttaccaaagg aagtcgaagc tgctagagcc 1920
gcatacggaa atggtactgc ccctatacca aatagaatca aagagtgtag gtcgtaccct 1980

```
ttgtacagat tcgttagaga agagttggga accaaattac taactggtga aaaagtcgtt   2040

agcccaggtg aagaatttga caaggtattc acagctatgt gcgagggaaa gttgatagat   2100

ccacttatgg attgcttgaa agagtggaat ggtgcaccta ttccaatctg ctaa         2154
```

<210> SEQ ID NO 27
<211> LENGTH: 35
<212> TYPE: DNA
<213> ORGANISM: Escherichia coli

<400> SEQUENCE: 27

```
cactaaaggg cggccgcatg gaccaaattg aagca                                35
```

<210> SEQ ID NO 28
<211> LENGTH: 38
<212> TYPE: DNA
<213> ORGANISM: Escherichia coli

<400> SEQUENCE: 28

```
aattaagagc tcagatcttt agcagattgg aataggtg                             38
```

<210> SEQ ID NO 29
<211> LENGTH: 1518
<212> TYPE: DNA
<213> ORGANISM: Artificial Sequence
<220> FEATURE:
<223> OTHER INFORMATION: Synthetic A.thaliana gene, codon optimised for S.cerevisiae expression

<400> SEQUENCE: 29

```
atggatttgt tattgctgga aaagtcactt attgctgtat ttgtggcagt tattctagcc     60

acggttattt ctaaattaag aggtaagaaa ctaaaactac ctcctggtcc catccccata    120

ccaatttttg gtaattggtt gcaagtgggc gatgatttga atcacagaaa tttggtagac    180

tatgctaaga agttcggtga ccttttcttg cttagaatgg gtcaaaggaa tttggtagtg    240

gttagctcac ctgatttgac taaggaggtc ttattaacgc aaggcgttga gtttggctcc    300

agaactagaa atgttgtgtt tgatattttc actggtaaag gtcaagatat ggtttttaca    360

gtttacggtg agcactggag aaaaatgaga agaatcatga ccgtaccatt ctttactaac    420

aaggttgttc aacaaaatag agaaggttgg gagtttgagg cagcttccgt agtggaagac    480

gtaaagaaaa atccagattc ggccacaaag ggtatagtac taagaaaaag actacaattg    540

atgatgtaca acaatatgtt cagaattatg tttgacagaa gatttgaaag tgaagatgac    600

cctttgttcc tgagacttaa ggctttgaat ggtgaaagat cgagattggc tcaaagtttc    660

gaatataatt acggtgactt tattccaatc ttaagaccat tttgagagg ctatttgaaa     720

atttgccaag acgtcaagga taggaggatc gctcttttca agaagtactt tgtggacgag    780

agaaagcaaa tagcttcttc caagcccaca ggttcggaag gtttaaaatg tgcaattgat    840

catattttag aagctgaaca aaaaggtgaa attaacgaag ataatgtttt gtacattgta    900

gaaaatatca atgtggctgc aatagaaaca accttatggt caatagaatg gggtattgct    960

gaattggtga atcacccaga aatacaatct aaactgagaa acgagctaga taccgtttta   1020

ggtccaggtg tccaagttac agaacctgat ttgcataagt taccctactt gcaagctgtg   1080

gttaaagaaa ccttgagatt gagaatggct attcctcttc tagttcctca tatgaaccta   1140

catgatgcta aactggccgg ttatgatatt ccagcagaaa gtaagatttt agtaaatgca   1200

tggtggttgg ccaacaatcc aaacagttgg aaaaagcctg aagaattcag acctgaaaga   1260
```

```
ttcttcgaag aggaatctca tgttgaagcc aacggaaatg acttcagata tgtacctttt   1320

ggcgttggca gaagatcgtg tccaggaata atactagcct taccaatatt gggtatcaca   1380

attggtagga tggttcaaaa ttttgagttg ctaccaccac ccggacaatc gaaagtcgat   1440

acttcagaga aaggaggaca attctcattg catattttga atcattccat tatagtcatg   1500

aaacccagaa attgttaa                                                 1518


<210> SEQ ID NO 30
<211> LENGTH: 40
<212> TYPE: DNA
<213> ORGANISM: Escherichia coli

<400> SEQUENCE: 30

atttccgaag aagacctcga gatggatttg ttattgctgg                           40


<210> SEQ ID NO 31
<211> LENGTH: 55
<212> TYPE: DNA
<213> ORGANISM: Escherichia coli

<400> SEQUENCE: 31

agtagatgga gtagatggag tagatggagt agatggacaa tttctgggtt tcatg          55


<210> SEQ ID NO 32
<211> LENGTH: 2136
<212> TYPE: DNA
<213> ORGANISM: Artificial Sequence
<220> FEATURE:
<223> OTHER INFORMATION: Synthetic A.thaliana gene, codon optimised for
      S.cerevisiae expression

<400> SEQUENCE: 32

atgtccagta gctcttcctc ctcaacctcg atgatcgact taatggctgc tattataaaa     60

ggagaaccag ttatagttag tgaccctgct aacgcaagcg cttacgaatc cgttgcagcc    120

gagttgtcaa gtatgcttat agaaaataga cagtttgcta tgattgtaac gaccagcatc    180

gccgttttaa ttggttgcat cgtgatgttg gtgtggagga ggagcggttc gggcaattca    240

aagagggttg aaccactaaa gccattagtt atcaaaccta gagaagagga aattgacgat    300

ggaaggaaga aagtcactat attcttcggc acccaaacag gtacagctga aggttttgct    360

aaggctctag gagaagaagc aaaagctaga tatgaaaaga cgagattcaa aattgtcgat    420

ctggatgact atgccgccga tgatgacgaa tacgaagaaa aattgaagaa agaagatgtc    480

gcatttttct tccttgccac ctacggcgac ggtgaaccaa cagataatgc cgcaaggttt    540

tacaagtggt ttactgaagg taatgacaga ggagaatggc tgaagaattt gaaatatggt    600

gtgttcggcc ttggtaacag acagtacgag cattttaata aggtcgctaa ggttgtagat    660

gatatacttg ttgaacaagg tgctcaaagg ttagtgcagg tgggcttggg tgacgatgat    720

caatgtattg aagatgactt tactgcttgg agagaagcct tgtggcctga attagatact    780

atccttagag aagaaggtga cactgctgtt gctaccccct acactgcagc agtcctagaa    840

tatagagtct caatccatga ttcagaagac gccaaattca atgatattaa catggccaac    900

ggtaacggtt acaccgtttt tgacgcacaa catccataca aagctaatgt tgctgttaaa    960

agggaacttc acaccccaga aagtgacagg tcatgtatac atttggaatt tgatatcgct   1020

ggtagtggtt tgacttacga aacaggtgac catgtcggag tactttgcga taatttgtca   1080

gaaactgttg atgaagcttt gaggttattg gatatgtcac cagatactta cttctcattg   1140

catgcagaaa aagaagacgg aactccaata tcaagctcgc ttccccctcc attccctccc   1200
```

```
tgtaacttaa gaacagccct aactagatat gcttgtttac tgtcttctcc aaagaaaagt   1260

gctttggttg cattggcagc ccacgcatcc gatcctaccg aagctgagag attaaagcat   1320

ttggcttcac cagccggtaa agatgaatac agtaagtggg tagtggagag ccaaagatcg   1380

cttttagaag tgatggctga gtttccaagt gctaaacctc ctctgggtgt atttttcgct   1440

ggtgtggccc caagattgca gcctagattt tattccatat cctcatctcc aaaaattgcc   1500

gaaaccagaa ttcacgtgac atgtgctctg gtctacgaaa agatgccaac aggtaggatt   1560

cacaagggtg tctgttctac ctggatgaaa aatgctgtac cctatgaaaa atccgaaaat   1620

tgttctagtg caccaatttt cgtaagacaa tctaatttca agttaccaag cgattctaaa   1680

gtacccatta ttatgatcgg tccaggtact ggtttggccc cattcagagg cttcttgcaa   1740

gaaagattgg ctttagtgga gagtggagtt gaattgggtc cttcagtttt attctttggt   1800

tgtagaaaca gaagaatgga ctttatctac gaagaagaat tgcagagatt tgttgaaagt   1860

ggtgcattgg ccgaattgag tgttgcattc agcagggaag gtccaaccaa agaatacgtt   1920

caacacaaga tgatggacaa ggcttctgat atctggaata tgatttccca aggtgcttat   1980

ttgtatgttt gtggtgacgc taaaggaatg gctagagatg ttcatagatc actgcataca   2040

atcgcacaag aacaaggtag catggattca acaaaagcag agggctttgt aaagaatctt   2100

cagacaagcg gtagatatct gagagatgta tggtaa                             2136
```

<210> SEQ ID NO 33
<211> LENGTH: 52
<212> TYPE: DNA
<213> ORGANISM: Escherichia coli

<400> SEQUENCE: 33

```
ccatctactc catctactcc atctactcca tctactagga ggagcggttc gg             52
```

<210> SEQ ID NO 34
<211> LENGTH: 44
<212> TYPE: DNA
<213> ORGANISM: Escherichia coli

<400> SEQUENCE: 34

```
atcttagcta gccgcggtac cttaccatac atctctcaga tatc                     44
```

<210> SEQ ID NO 35
<211> LENGTH: 1182
<212> TYPE: DNA
<213> ORGANISM: Artificial Sequence
<220> FEATURE:
<223> OTHER INFORMATION: Synthetic V.vinifera gene, codon optimised for S.cerevisiae expression

<400> SEQUENCE: 35

```
atggcatccg tagaggagtt cagaaatgca cagagggcaa aaggtccagc aaccatattg     60

gctattggaa cagccacccc tgatcactgt gtttatcaat ctgattacgc tgattactat    120

ttcagagtaa ctaaaagtga acatatgaca gaacttaaga aaaagtttaa tagaatttgt    180

gataaatcta tgataaagaa aagatacata catctaactg aagaaatgtt agaggaacat    240

ccaaatatag gtgcatatat ggcaccatct ttgaatatta gacaagaaat cataacagcc    300

gaggtaccta gactaggtag agacgcagcc ttgaaagctt taaaggaatg gggacaacca    360

aaatctaaga ttacacattt ggttttctgt acaacttccg gtgtcgaaat gccaggtgct    420

gattataaac tagcaaacct attgggatta gagacctctg ttagaagagt tatgttgtat    480
```

```
catcaaggtt gttacgccgg aggtacagtg cttagaactg ctaaggattt ggcagaaaat    540

aacgccggtg ctagggtttt agtcgtctgc agtgaaatca ctgtcgtaac tttcagaggt    600

ccatcagaag atgctctaga cagtttggtc ggacaagcat tgtttggcga tggatcttcc    660

gccgtaattg taggcagcga tcctgatgtg tccattgaaa gaccactatt tcaattagtt    720

tctgctgctc aaacttttat tccaaattcc gccggtgcca tagcaggaaa cttgagagaa    780

gttggtttga cttttcattt gtggcctaat gtcccaacct taatttcaga aaacatcgaa    840

aaatgcttaa ctcaagcctt tgacccattg ggcataagcg actggaactc attgttttgg    900

attgctcatc caggtggtcc agcaatttta gacgcagtgg aggcaaaact aaacttagag    960

aagaaaaagt tggaagctac aagacacgtt ctatcagagt atggcaacat gagctctgcc   1020

tgcgttttat tcattctaga tgagatgagg aagaagtctt taaagggtga aaaagccaca   1080

accggagaag gtttagattg ggtgttcta tttggtttcg gtcctggctt aacaattgag   1140

acagtggtgt tacactctgt tccaactgtc actaactaat ga                      1182
```

```
<210> SEQ ID NO 36
<211> LENGTH: 34
<212> TYPE: DNA
<213> ORGANISM: Escherichia coli

<400> SEQUENCE: 36

ccggatcctc atggcatccg tcgaagagtt cagg                                  34
```

```
<210> SEQ ID NO 37
<211> LENGTH: 38
<212> TYPE: DNA
<213> ORGANISM: Escherichia coli

<400> SEQUENCE: 37

cgctcgagtt ttagttagta actgtgggaa cgctatgc                              38
```

```
<210> SEQ ID NO 38
<211> LENGTH: 40
<212> TYPE: DNA
<213> ORGANISM: Escherichia coli

<400> SEQUENCE: 38

gcgaattctt atgacgacac aagatgtgat agtcaatgat                            40
```

```
<210> SEQ ID NO 39
<211> LENGTH: 41
<212> TYPE: DNA
<213> ORGANISM: Escherichia coli

<400> SEQUENCE: 39

gcactagtat cctagttcat taatccattt gctagtcttg c                          41
```

```
<210> SEQ ID NO 40
<211> LENGTH: 10157
<212> TYPE: DNA
<213> ORGANISM: Vitis vinifera

<400> SEQUENCE: 40

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240
```

-continued

```
gaacacggca ttagtcaggg aagtcataac acagtccttt cccgcaattt tctttttcta    300
ttactcttgg cctcctctag tacactctat atttttttat gcctcggtaa tgattttcat    360
ttttttttt ccccctagcgg atgactcttt tttttcttta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
ccttttttct tttgctttt tcttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aatttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctgaattg gagcgacctc atgctatacc   1980
tgagaaagca acctgaccta caggaaagag ttactcaaga ataagaattt tcgttttaaa   2040
acctaagagt cactttaaaa tttgtataca cttatttttt ttataactta tttaataata   2100
aaaatcataa atcataagaa attcgcttat ttagaagtgt caacaacgta tctaccaacg   2160
atttgaccct tttccatctt ttcgtaaatt tctggcaagg tagacaagcc gacaaccttg   2220
attggagact tgaccaaacc tctggcgaag aattgttaat taagagctca gatcttatcg   2280
tcgtcatcct tgtaatccat cgatactagt ctagttcatt aatccatttg ctagtcttgc   2340
tcttagatcc ttcctcaata tcttccctga tggagcttta ggaatagagt cagtgaagaa   2400
cactttgttg attctcttat aaaacacaac ctgttttgac acgaattgct tgatttcatc   2460
ttcggatata tttgaatctt tcgatctcac cacaaacgca acaggaacct caccagcatc   2520
ttcttccttc atggcgacga cagcaacatc attgatttct ggatgaccta tgaggagaga   2580
ctctagctca gctggagcca cttgaaatcc tttgtacttg atgagttctt tcaatctatc   2640
```

```
cacaatgaaa agctcgtcgt catcatcgat aaatccgacg tctccagtgt gaagccaacc   2700
atctttatcg atcgtcgatg ccgtggccaa ggggtcattg agatagcctt tcatgatttg   2760
gttgccacgg atgcatattt cgccgggttt gttcctaggc aaagaatctc ctgtgtctgg   2820
atcaagtatc ttcatctcgg cgttcctcac caccgtacca catgctcctg acttcactgg   2880
aaacggctct ttagcaaacc ctaacgacat tgctagcacc ggacctgctt ctgtcatccc   2940
atagccctga ccaagcttgg cgttaggaaa cttagcacta atagcatctt caagctcctt   3000
accaagagga gctgctccag acttaaccat cctaaccgag ctcagatcat acttctccgt   3060
ctccggcgac ttcgcgatag ctaaaacgat cggtggcacg accatagcca ccgtgacttt   3120
acacctttgt atctgctcta acaagagagt gatttcgaac ttaggcatta tcaagatcgt   3180
ggcaccaact ctgagactac agagcatgat ggagttgaga gcgtatatat ggaacatagg   3240
caagacacag aggatcacgt cgtctctgtt gaagtaaaga ttcggattct cgccgtcgac   3300
ttgctgcgcc acgctcgtga ctagaccttt gtgtgttagc atcactcctt tggggagacc   3360
cgtcgtgccg gatgagaaag gaagcgccac gacgtcttct ggcgaaatct tctccggtat   3420
tgagtccact cgtggttctt cggactgagt taactcggag aaacggaggc agttttcggg   3480
gatggcgtcg gagtcggtgg tgacgatcaa aacgccgtcg ttttggaggt tcttgatttt   3540
atcgacgtaa cgggattgag tgacgatgag tttcgccgcg gaggctttgg cttgtttaga   3600
aatctccgcc ggagtgaaga acgggttcgc ggaggtggtg attgcgccga tgaaggaggc   3660
ggcaaggaaa gtgaggacta cttcaggaga gttcgggagg aggatcatta caacgtcgtg   3720
ttgcttcacg ccgaggttat gaagaccggc ggcgagtttc cgagatgtta cgtggacatc   3780
ggcgtaggtg tatacttcgc cggtgggacc gttgatcaag catggcttag cggcgaactc   3840
tgagatattt tcgaagatgt agtcgtggag tgggaggtgg ttagggatgt atatatcagg   3900
caatctcgat cggaaaatga cgtcattact acactgtttc tgatcattct gatcattgac   3960
tatcacatct tgtgtcgtca tgaattctct agaatccgtc gaaactaagt tctggtgttt   4020
taaaactaaa aaaaagacta actataaaag tagaatttaa gaagtttaag aaatagattt   4080
acagaattac aatcaatacc taccgtcttt atatacttat tagtcaagta ggggaataat   4140
ttcagggaac tggtttcaac cttttttttc agctttttcc aaatcagaga gagcagaagg   4200
taatagaagg tgtaagaaaa tgagatagat acatgcgtgg gtcaattgcc ttgtgtcatc   4260
atttactcca ggcaggttgc atcactccat tgaggttgtg cccgtttttt gcctgtttgt   4320
gcccctgttc tctgtagttg cgctaagaga atggacctat gaactgatgg ttggtgaaga   4380
aaacaatatt ttggtgctgg gattcttttt ttttctggat gccagcttaa aaagcgggct   4440
ccattatatt tagtggatgc caggaataaa ctgttcaccc agacacctac gatgttatat   4500
attctgtgta acccgccccc tattttgggc atgtacgggt tacagcagaa ttaaaaggct   4560
aattttttga ctaaataaag ttaggaaaat cactactatt aattatttac gtattctttg   4620
aaatggcgag tattgataat gataaactga gctcggaaga gcgcccaata cgcaaaccgc   4680
ctctccccgc gcgttggccg attcattaat gcagctggca cgacaggttt cccgactgga   4740
aagcgggcag tgagcgcaac gcaattaatg tgagttacct cactcattag gcaccccagg   4800
ctttacactt tatgcttccg gctcctatgt tgtgtggaat tgtgagcgga taacaatttc   4860
acacaggaaa cagctatgac catgattacg ccaagcgcgc aattaaccct cactaaaggg   4920
aacaaaagct ggagctcata gcttcaaaat gtttctactc ctttttttact cttccagatt   4980
ttctcggact ccgcgcatcg ccgtaccact tcaaaacacc caagcacagc atactaaatt   5040
```

-continued

```
tcccctcttt cttcctctag ggtgtcgtta attacccgta ctaaaggttt ggaaaagaaa   5100
aaagagaccg cctcgtttct ttttcttcgt cgaaaaaggc aataaaaatt tttatcacgt   5160
ttctttttct tgaaaatttt ttttttgatt tttttctctt tcgatgacct cccattgata   5220
tttaagttaa taaacggtct tcaatttctc aagtttcagt ttcatttttc ttgttctatt   5280
acaacttttt ttacttcttg ctcattagaa agaaagcata gcaatctaat ctaagttttc   5340
tagaggatcc atggcatccg tagaggagtt cagaaatgca cagagggcaa aaggtccagc   5400
aaccatattg gctattggaa cagccacccc tgatcactgt gtttatcaat ctgattacgc   5460
tgattactat ttcagagtaa ctaaaagtga acatatgaca gaacttaaga aaaagtttaa   5520
tagaatttgt gataaatcta tgataaagaa aagatacata catctaactg aagaaatgtt   5580
agaggaacat ccaaatatag gtgcatatat ggcaccatct ttgaatatta gacaagaaat   5640
cataacagcc gaggtaccta gactaggtag agacgcagcc ttgaaagctt taaaggaatg   5700
gggacaacca aaatctaaga ttacacattt ggtttttctgt acaacttccg gtgtcgaaat   5760
gccaggtgct gattataaac tagcaaacct attgggatta gagacctctg ttagaagagt   5820
tatgttgtat catcaaggtt gttacgccgg aggtacagtg cttagaactg ctaaggattt   5880
ggcagaaaat aacgccggtg ctagggtttt agtcgtctgc agtgaaatca ctgtcgtaac   5940
tttcagaggt ccatcagaag atgctctaga cagtttggtc ggacaagcat tgtttggcga   6000
tggatcttcc gccgtaattg taggcagcga tcctgatgtg tccattgaaa gaccactatt   6060
tcaattagtt tctgctgctc aaacttttat tccaaattcc gccggtgcca tagcaggaaa   6120
cttgagagaa gttggtttga cttttcattt gtggcctaat gtcccaacct taatttcaga   6180
aaacatcgaa aaatgcttaa ctcaagcctt tgacccattg ggcataagcg actggaactc   6240
attgttttgg attgctcatc caggtggtcc agcaatttta gacgcagtgg aggcaaaact   6300
aaacttagag aagaaaaagt tggaagctac aagacacgtt ctatcagagt atggcaacat   6360
gagctctgcc tgcgttttat tcattctaga tgagatgagg aagaagtctt taaagggtga   6420
aaaagccaca accggagaag gtttagattg ggtgttcta tttggtttcg gtcctggctt   6480
aacaattgag acagtggtgt tacactctgt tccaactgtc actaactaat gactcgagta   6540
agcttggtac cgcggctagc taagatccgc tctaaccgaa aaggaaggag ttagacaacc   6600
tgaagtctag gtccctattt attttttttat agttatgtta gtattaagaa cgttatttat   6660
atttcaaatt tttctttttt ttctgtacag acgcgtgtac gcatgtaaca ttatactgaa   6720
aaccttgctt gagaaggttt tgggacgctc gaagatccag ctgcattaat gaatcggcca   6780
acgcgcgggg agaggcggtt tgcgtattgg gcgctcttcc gcttcctcgc tcactgactc   6840
gctgcgctcg gtcgttcggc tgcggcgagc ggtatcagct cactcaaagg cggtaatacg   6900
gttatccaca gaatcagggg ataacgcagg aaagaacatg tgagcaaaag gccagcaaaa   6960
ggccaggaac cgtaaaaagg ccgcgttgct ggcgtttttc cataggctcc gcccccctga   7020
cgagcatcac aaaaatcgac gctcaagtca gaggtggcga aacccgacag gactataaag   7080
ataccaggcg tttccccctg gaagctccct cgtgcgctct cctgttccga ccctgccgct   7140
taccggatac ctgtccgcct ttctcccttc gggaagcgtg gcgctttctc atagctcacg   7200
ctgtaggtat ctcagttcgg tgtaggtcgt tcgctccaag ctgggctgtg tgcacgaacc   7260
ccccgttcag cccgaccgct gcgccttatc cggtaactat cgtcttgagt ccaacccggt   7320
aagacacgac ttatcgccac tggcagcagc cactggtaac aggattagca gagcgaggta   7380
tgtaggcggt gctacagagt tcttgaagtg gtggcctaac tacggctaca ctagaaggac   7440
```

-continued

```
agtatttggt atctgcgctc tgctgaagcc agttaccttc ggaaaaagag ttggtagctc   7500
ttgatccggc aaacaaacca ccgctggtag cggtggtttt tttgtttgca agcagcagat   7560
tacgcgcaga aaaaaaggat ctcaagaaga tcctttgatc ttttctacgg ggtctgacgc   7620
tcagtggaac gaaaactcac gttaagggat tttggtcatg agattatcaa aaaggatctt   7680
cacctagatc cttttaaatt aaaaatgaag ttttaaatca atctaaagta tatatgagta   7740
aacttggtct gacagttacc aatgcttaat cagtgaggca cctatctcag cgatctgtct   7800
atttcgttca tccatagttg cctgactccc cgtcgtgtag ataactacga tacgggaggg   7860
cttaccatct ggccccagtg ctgcaatgat accgcgagac ccacgctcac cggctccaga   7920
tttatcagca ataaaccagc cagccggaag ggccgagcgc agaagtggtc ctgcaacttt   7980
atccgcctcc atccagtcta ttaattgttg ccgggaagct agagtaagta gttcgccagt   8040
taatagtttg cgcaacgttg ttgccattgc tacaggcatc gtggtgtcac gctcgtcgtt   8100
tggtatggct tcattcagct ccggttccca acgatcaagg cgagttacat gatcccccat   8160
gttgtgcaaa aaagcggtta gctccttcgg tcctccgatc gttgtcagaa gtaagttggc   8220
cgcagtgtta tcactcatgg ttatggcagc actgcataat tctcttactg tcatgccatc   8280
cgtaagatgc ttttctgtga ctggtgagta ctcaaccaag tcattctgag aatagtgtat   8340
gcggcgaccg agttgctctt gcccggcgtc aatacgggat aataccgcgc cacatagcag   8400
aactttaaaa gtgctcatca ttggaaaacg ttcttcgggg cgaaaactct caaggatctt   8460
accgctgttg agatccagtt cgatgtaacc cactcgtgca cccaactgat cttcagcatc   8520
ttttactttc accagcgttt ctgggtgagc aaaaacagga aggcaaaatg ccgcaaaaaa   8580
gggaataagg gcgacacgga aatgttgaat actcatactc ttcctttttc aatattattg   8640
aagcatttat cagggttatt gtctcatgag cggatacata tttgaatgta tttagaaaaa   8700
taaacaaata ggggttccgc gcacatttcc ccgaaaagtg ccacctgaac gaagcatctg   8760
tgcttcattt tgtagaacaa aaatgcaacg cgagagcgct aatttttcaa acaaagaatc   8820
tgagctgcat ttttacagaa cagaaatgca acgcgaaagc gctattttac caacgaagaa   8880
tctgtgcttc atttttgtaa aacaaaaatg caacgcgaga gcgctaattt ttcaaacaaa   8940
gaatctgagc tgcattttta cagaacagaa atgcaacgcg agagcgctat tttaccaaca   9000
aagaatctat acttcttttt tgttctacaa aaatgcatcc cgagagcgct atttttctaa   9060
caaagcatct tagattactt tttttctcct ttgtgcgctc tataatgcag tctcttgata   9120
actttttgca ctgtaggtcc gttaaggtta gaagaaggct actttggtgt ctattttctc   9180
ttccataaaa aaagcctgac tccacttccc gcgtttactg attactagcg aagctgcggg   9240
tgcatttttt caagataaag gcatccccga ttatattcta taccgatgtg gattgcgcat   9300
actttgtgaa cagaaagtga tagcgttgat gattcttcat tggtcagaaa attatgaacg   9360
gtttcttcta ttttgtctct atatactacg tataggaaat gtttacattt tcgtattgtt   9420
ttcgattcac tctatgaata gttcttacta caattttttt gtctaaagag taatactaga   9480
gataaacata aaaaatgtag aggtcgagtt tagatgcaag ttcaaggagc gaaaggtgga   9540
tgggtaggtt atatagggat atagcacaga gatatatagc aaagagatac ttttgagcaa   9600
tgtttgtgga agcggtattc gcaatatttt agtagctcgt tacagtccgg tgcgtttttg   9660
gtttttttgaa agtgcgtctt cagagcgctt ttggttttca aaagcgctct gaagttccta   9720
tactttctag agaataggaa cttcggaata ggaacttcaa agcgtttccg aaaacgagcg   9780
cttccgaaaa tgcaacgcga gctgcgcaca tacagctcac tgttcacgtc gcacctatat   9840
```

```
ctgcgtgttg cctgtatata tatatacatg agaagaacgg catagtgcgt gtttatgctt   9900

aaatgcgtac ttatatgcgt ctatttatgt aggatgaaag gtagtctagt acctcctgtg   9960

atattatccc attccatgcg gggtatcgta tgcttccttc agcactaccc tttagctgtt  10020

ctatatgctg ccactcctca attggattag tctcatcctt caatgctatc atttcctttg  10080

atattggatc atctaagaaa ccattattat catgacatta acctataaaa ataggcgtat  10140

cacgaggccc tttcgtc                                                 10157


<210> SEQ ID NO 41
<211> LENGTH: 40
<212> TYPE: DNA
<213> ORGANISM: Arabidopsis thaliana

<400> SEQUENCE: 41

atttccgaag aagacctcga gatggatttg ttattgctgg                           40


<210> SEQ ID NO 42
<211> LENGTH: 55
<212> TYPE: DNA
<213> ORGANISM: Arabidopsis thaliana

<400> SEQUENCE: 42

agtagatgga gtagatggag tagatggagt agatggacaa tttctgggtt tcatg          55


<210> SEQ ID NO 43
<211> LENGTH: 52
<212> TYPE: DNA
<213> ORGANISM: Arabidopsis thaliana

<400> SEQUENCE: 43

ccatctactc catctactcc atctactcca tctactagga ggagcggttc gg             52


<210> SEQ ID NO 44
<211> LENGTH: 44
<212> TYPE: DNA
<213> ORGANISM: Arabidopsis thaliana

<400> SEQUENCE: 44

atcttagcta gccgcggtac cttaccatac atctctcaga tatc                      44


<210> SEQ ID NO 45
<211> LENGTH: 12214
<212> TYPE: DNA
<213> ORGANISM: Artificial Sequence
<220> FEATURE:
<223> OTHER INFORMATION: Synthetic sequence derived from two A.thaliana
      genes

<400> SEQUENCE: 45

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataccac agcttttcaa ttcaattcat catttttttt ttattctttt ttttgatttc    240

ggtttctttg aaattttttt gattcggtaa tctccgaaca gaaggaagaa cgaaggaagg    300

agcacagact tagattggta tatatacgca tatgtagtgt tgaagaaaca tgaaattgcc    360

cagtattctt aacccaactg cacagaacaa aaacctgcag gaaacgaaga taaatcatgt    420

cgaaagctac atataaggaa cgtgctgcta ctcatcctag tcctgttgct gccaagctat    480

ttaatatcat gcacgaaaag caaacaaact tgtgtgcttc attggatgtt cgtaccacca    540
```

-continued

```
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtccat tcgccattca ggctgcgcaa ctgttgggaa gggcgatcgg tgcgggcctc   1860
ttcgctatta cgccagctga attggagcga cctcatgcta tacctgagaa agcaacctga   1920
cctacaggaa agagttactc aagaataaga attttcgttt taaaacctaa gagtcacttt   1980
aaaatttgta tacacttatt tttttataa cttatttaat aataaaaatc ataaatcata   2040
agaaattcgc ttatttagaa gtgtcaacaa cgtatctacc aacgatttga ccctttcca   2100
tcttttcgta aatttctggc aaggtagaca agccgacaac cttgattgga gacttgacca   2160
aacctctggc gaagaattgt taattaagag ctcagatctt tagcagattg gaataggtgc   2220
accattccac tctttcaagc aatccataag tggatctatc aactttccct cgcacatagc   2280
tgtgaatacc ttgtcaaatt cttcacctgg gctaacgact tttcaccag ttagtaattt   2340
ggttcccaac tcttctctaa cgaatctgta caaagggtac gacctacact ctttgattct   2400
atttggtata ggggcagtac catttccgta tgcggctcta gcagcttcga cttcctttgg   2460
taaaactgcc ttcagttctt cttcaaaggc acctatcttt tggaatattg aagtaacggc   2520
atttttctca gtttcaccat tggataaagc gtgatctaca ataacttgtc tcaatctctg   2580
catcaatgga taagtagcgc tacatggatc gtcaacgtaa gtaaatactt gttctctatc   2640
tacaactttt aataaatctt tttcacagaa tcttgatggg tgcaattcac cattgatacc   2700
tgtagttaga acctttttg caacctgtga tacggtattt ttcactgtct gtctcaaatt   2760
ctcttccaag tgtctcaaat ctacggcctg gcatataccc actaaaaatg ttgtggacat   2820
taatttaagg atatcaacgg cctcgcttgt ttttcttgat gaaatcaggc ccaaagaatt   2880
aacatcctga ttgtgttgtt cggctgattg tacatgagag gttactgggt tggctagata   2940
```

```
ttgcagctct gaacaatagc ttgccattgc tatctcagca cctttgaaac cataatcaag   3000
actagggtta gaagatgcgg tcagattcga aggcaaaccg ttattgtaga agtcattgac   3060
caattcagaa aattgggcaa acattaattt gccaattgcg gctatggcaa gcctggtatt   3120
atccatactg actcctatgg gtgtaccctg gaaattgcct ccatgtattg ccttattcct   3180
cgacacatca ataagtggat tatcgttaac agagttgatc tctctttcta tagactttgt   3240
agcttgtcta attacttcaa tttgagggcc aagccattgt ggggatgtcc ttaaagcata   3300
tctatcttgt ttgggttttt gcaaagggtc catttcatga accttctggg ctaacttcat   3360
gtagctagag ccgtccaaaa tgtgctccat gatagctgct gcttcaattt gtcctgggtg   3420
atgttttaac ctgtgggtca agtgatcagt aaactcaggt tttccactca tgacttcggc   3480
aaaaattgcg gacaaaactt cggccaaaac tgcttgtacg ttagcttcaa acaacaccat   3540
ggatgccata ccgctgccga cagcggtgcc attcaccagg gctaaacctt ccttgggttg   3600
caaatcaaag aaaccagttg aaataccagc tttctcaaat gcttccttag cggttaagga   3660
ttctccgtct ggaccagtgg cctttgaatt aggtcttccc gttaataagc ctgcgatata   3720
tgaaagggga accaaatcac cgctggcagt tattgttcct cttaagggca acgaaggaga   3780
aatgttgtgg ttcaatagtg aagtgatggc ctcaagaatt tcaaacctta ttccagagta   3840
accttgcaac aaagtgttca ccctaacaag catagcagct cttgttgccg attggggtaa   3900
tgtatggcaa gtttcctttg tattaccgaa aataccggcg ttaaggaatc tgatcagttc   3960
tgtttgcaaa gcagtgccat ttttagttct tctatgagag gtagcaccaa agcctgtggt   4020
aacgccatag gaatctgtgc ccttgttcat actttccatg acccaatctg atgaagcctt   4080
aactccggct ctacttgttt ctgcaagttc taccttcact gaaccgccaa cggtcgaaat   4140
agcagctacc tgtcctatcg tcaatgtctc gccgcctaga tttacgactg gtcttctgta   4200
ttcctcaacc atcttcttaa cttcatccag atggctacct ttcatctggt cagctgccag   4260
accccaattc aaaggatctg caagagtttt tgtcgttacg gccaccttgg tcttttcacc   4320
accaccgcat agcattgctt caatttggtc catgcggccg ccctttagtg agggttgaat   4380
tcgaattttc aaaaattctt actttttttt tggatggacg caaagaagtt taataatcat   4440
attacatggc attaccacca tatacatatc catatacata tccatatcta atcttactta   4500
tatgttgtgg aaatgtaaag agccccatta tcttagccta aaaaaacctt ctctttggaa   4560
ctttcagtaa tacgcttaac tgctcattgc tatattgaag tacggattag aagccgccga   4620
gcgggtgaca gccctccgaa ggaagactct cctccgtgcg tcctcgtctt caccggtcgc   4680
gttcctgaaa cgcagatgtg cctcgcgccg cactgctccg aacaataaag attctacaat   4740
actagctttt atggttatga agaggaaaaa ttggcagtaa cctggcccca caaaccttca   4800
aatgaacgaa tcaaattaac aaccatagga tgataatgcg attagttttt tagccttatt   4860
tctggggtaa ttaatcagcg aagcgatgat tttgatctta ttaacagata tataaatgca   4920
aaaactgcat aaccacttta actaatactt tcaacatttt cggtttgtat tacttcttat   4980
tcaaatgtaa taaaagtatc aacaaaaaat tgttaatata cctctatact ttaacgtcaa   5040
ggagaaaaaa ccccggatcc gtaatacgac tcactatagg gcccgggcgt cgacatggaa   5100
cagaagttga tttccgaaga agacctcgag atggatttgt tattgctgga aaagtcactt   5160
attgctgtat ttgtggcagt tattctagcc acggttattt ctaaattaag aggtaagaaa   5220
ctaaaactac ctcctggtcc catccccata ccaatttttg gtaattggtt gcaagtgggc   5280
gatgatttga atcacagaaa tttggtagac tatgctaaga agttcggtga ccttttcttg   5340
```

```
cttagaatgg gtcaaaggaa tttggtagtg gttagctcac ctgatttgac taaggaggtc   5400
ttattaacgc aaggcgttga gtttggctcc agaactagaa atgttgtgtt tgatattttc   5460
actggtaaag gtcaagatat ggtttttaca gtttacggtg agcactggag aaaaatgaga   5520
agaatcatga ccgtaccatt ctttactaac aaggttgttc aacaaaatag agaaggttgg   5580
gagtttgagg cagcttccgt agtggaagac gtaaagaaaa atccagattc ggccacaaag   5640
ggtatagtac taagaaaaag actacaattg atgatgtaca acaatatgtt cagaattatg   5700
tttgacagaa gatttgaaag tgaagatgac cctttgttcc tgagacttaa ggctttgaat   5760
ggtgaaagat cgagattggc tcaaagtttc gaatataatt acggtgactt tattccaatc   5820
ttaagaccat tttgagaggg ctatttgaaa atttgccaag acgtcaagga taggaggatc   5880
gctcttttca agaagtactt tgtggacgag agaaagcaaa tagcttcttc caagcccaca   5940
ggttcggaag gtttaaaatg tgcaattgat catattttag aagctgaaca aaaaggtgaa   6000
attaacgaag ataatgtttt gtacattgta gaaaatatca atgtggctgc aatagaaaca   6060
accttatggt caatagaatg ggtattgct gaattggtga atcacccaga aatacaatct   6120
aaactgagaa acgagctaga taccgtttta ggtccaggtg tccaagttac agaacctgat   6180
ttgcataagt taccctactt gcaagctgtg gttaaagaaa ccttgagatt gagaatggct   6240
attcctcttc tagttcctca tatgaaccta catgatgcta aactggccgg ttatgatatt   6300
ccagcagaaa gtaagatttt agtaaatgca tggtggttgg ccaacaatcc aaacagttgg   6360
aaaaagcctg aagaattcag acctgaaaga ttcttcgaag aggaatctca tgttgaagcc   6420
aacggaaatg acttcagata tgtacctttt ggcgttggca gaagatcgtg tccaggaata   6480
atactagcct taccaatatt gggtatcaca attggtagga tggttcaaaa ttttgagttg   6540
ctaccaccac ccggacaatc gaaagtcgat acttcagaga aaggaggaca attctcattg   6600
catattttga atcattccat tatagtcatg aaacccagaa attgtccatc tactccatct   6660
actccatcta ctccatctac taggaggagc ggttcgggca attcaaagag ggttgaacca   6720
ctaaagccat tagttatcaa acctagagaa gaggaaattg acgatggaag gaagaaagtc   6780
actatattct tcggcaccca aacaggtaca gctgaaggtt ttgctaaggc tctaggagaa   6840
gaagcaaaag ctagatatga aaagacgaga ttcaaaattg tcgatctgga tgactatgcc   6900
gccgatgatg acgaatacga agaaaaattg aagaaagaag atgtcgcatt tttcttcctt   6960
gccacctacg gcgacggtga accaacagat aatgccgcaa ggttttacaa gtggtttact   7020
gaaggtaatg acagaggaga atggctgaag aatttgaaat atggtgtgtt cggccttggt   7080
aacagacagt acgagcattt taataaggtc gctaaggttg tagatgatat acttgttgaa   7140
caaggtgctc aaaggttagt gcaggtgggc ttgggtgacg atgatcaatg tattgaagat   7200
gactttactg cttggagaga agccttgtgg cctgaattag atactatcct tagagaagaa   7260
ggtgacactg ctgttgctac cccctacact gcagcagtcc tagaatatag agtctcaatc   7320
catgattcag aagacgccaa attcaatgat attaacatgg ccaacggtaa cggttacacc   7380
gtttttgacg cacaacatcc atacaaagct aatgttgctg ttaaaaggga acttcacacc   7440
ccagaaagtg acaggtcatg tatacatttg gaatttgata tcgctggtag tggtttgact   7500
tacgaaacag gtgaccatgt cggagtactt tgcgataatt tgtcagaaac tgttgatgaa   7560
gctttgaggt tattggatat gtcaccagat acttacttct cattgcatgc agaaaaagaa   7620
gacggaactc caatatcaag ctcgcttccc cctccattcc ctccctgtaa cttaagaaca   7680
gccctaacta gatatgcttg tttactgtct tctccaaaga aaagtgcttt ggttgcattg   7740
```

```
gcagcccacg catccgatcc taccgaagct gagagattaa agcatttggc ttcaccagcc   7800
ggtaaagatg aatacagtaa gtgggtagtg gagagccaaa gatcgctttt agaagtgatg   7860
gctgagtttc caagtgctaa acctcctctg ggtgtatttt tcgctggtgt ggccccaaga   7920
ttgcagccta gattttattc catatcctca tctccaaaaa ttgccgaaac cagaattcac   7980
gtgacatgtg ctctggtcta cgaaaagatg ccaacaggta ggattcacaa gggtgtctgt   8040
tctacctgga tgaaaaatgc tgtaccctat gaaaaatccg aaaattgttc tagtgcacca   8100
attttcgtaa gacaatctaa tttcaagtta ccaagcgatt ctaaagtacc cattattatg   8160
atcggtccag gtactggttt ggccccattc agaggcttct tgcaagaaag attggcttta   8220
gtggagagtg gagttgaatt gggtccttca gttttattct ttggttgtag aaacagaaga   8280
atggacttta tctacgaaga agaattgcag agatttgttg aaagtggtgc attggccgaa   8340
ttgagtgttg cattcagcag ggaaggtcca accaaagaat acgttcaaca caagatgatg   8400
gacaaggctt ctgatatctg gaatatgatt tcccaaggtg cttatttgta tgtttgtggt   8460
gacgctaaag gaatggctag agatgttcat agatcactgc atacaatcgc acaagaacaa   8520
ggtagcatgg attcaacaaa agcagagggc tttgtaaaga atcttcagac aagcggtaga   8580
tatctgagag atgtatggta aggtaccgcg gctagctaag atccgctcta accgaaaagg   8640
aaggagttag acaacctgaa gtctaggtcc ctatttattt ttttatagtt atgttagtat   8700
taagaacgtt atttatattt caaatttttc ttttttttct gtacagacgc gtgtacgcat   8760
gtaacattat actgaaaacc ttgcttgaga aggttttggg acgctcgaag atccagctgc   8820
attaatgaat cggccaacgc gcggggagag gcggtttgcg tattgggcgc tcttccgctt   8880
cctcgctcac tgactcgctg cgctcggtcg ttcggctgcg gcgagcggta tcagctcact   8940
caaaggcggt aatacggtta tccacagaat caggggataa cgcaggaaag aacatgtgag   9000
caaaaggcca gcaaaaggcc aggaaccgta aaaaggccgc gttgctggcg tttttccata   9060
ggctccgccc ccctgacgag catcacaaaa atcgacgctc aagtcagagg tggcgaaacc   9120
cgacaggact ataaagatac caggcgtttc cccctggaag ctccctcgtg cgctctcctg   9180
ttccgaccct gccgcttacc ggatacctgt ccgcctttct cccttcggga agcgtggcgc   9240
tttctcatag ctcacgctgt aggtatctca gttcggtgta ggtcgttcgc tccaagctgg   9300
gctgtgtgca cgaacccccc gttcagcccg accgctgcgc cttatccggt aactatcgtc   9360
ttgagtccaa cccggtaaga cacgacttat cgccactggc agcagccact ggtaacagga   9420
ttagcagagc gaggtatgta ggcggtgcta cagagttctt gaagtggtgg cctaactacg   9480
gctacactag aaggacagta tttggtatct gcgctctgct gaagccagtt accttcggaa   9540
aaagagttgg tagctcttga tccggcaaac aaaccaccgc tggtagcggt ggtttttttg   9600
tttgcaagca gcagattacg cgcagaaaaa aaggatctca agaagatcct ttgatctttt   9660
ctacggggtc tgacgctcag tggaacgaaa actcacgtta agggattttg gtcatgagat   9720
tatcaaaaag gatcttcacc tagatccttt taaattaaaa atgaagtttt aaatcaatct   9780
aaagtatata tgagtaaact tggtctgaca gttaccaatg cttaatcagt gaggcaccta   9840
tctcagcgat ctgtctattt cgttcatcca tagttgcctg actccccgtc gtgtagataa   9900
ctacgatacg ggagggctta ccatctggcc ccagtgctgc aatgataccg cgagacccac   9960
gctcaccggc tccagattta tcagcaataa accagccagc cggaagggcc gagcgcagaa  10020
gtggtcctgc aactttatcc gcctccatcc agtctattaa ttgttgccgg gaagctagag  10080
taagtagttc gccagttaat agtttgcgca acgttgttgc cattgctaca ggcatcgtgg  10140
```

```
tgtcacgctc gtcgtttggt atggcttcat tcagctccgg ttcccaacga tcaaggcgag  10200

ttacatgatc ccccatgttg tgcaaaaaag cggttagctc cttcggtcct ccgatcgttg  10260

tcagaagtaa gttggccgca gtgttatcac tcatggttat ggcagcactg cataattctc  10320

ttactgtcat gccatccgta agatgctttt ctgtgactgg tgagtactca accaagtcat  10380

tctgagaata gtgtatgcgg cgaccgagtt gctcttgccc ggcgtcaata cgggataata  10440

ccgcgccaca tagcagaact ttaaaagtgc tcatcattgg aaaacgttct tcggggcgaa  10500

aactctcaag gatcttaccg ctgttgagat ccagttcgat gtaacccact cgtgcaccca  10560

actgatcttc agcatctttt actttcacca gcgtttctgg gtgagcaaaa acaggaaggc  10620

aaaatgccgc aaaaaaggga ataagggcga cacggaaatg ttgaatactc atactcttcc  10680

tttttcaata ttattgaagc atttatcagg gttattgtct catgagcgga tacatatttg  10740

aatgtattta gaaaaataaa caaatagggg ttccgcgcac atttccccga aaagtgccac  10800

ctgaacgaag catctgtgct tcattttgta gaacaaaaat gcaacgcgag agcgctaatt  10860

tttcaaacaa agaatctgag ctgcattttt acagaacaga aatgcaacgc gaaagcgcta  10920

ttttaccaac gaagaatctg tgcttcattt ttgtaaaaca aaaatgcaac gcgagagcgc  10980

taatttttca aacaaagaat ctgagctgca tttttacaga acagaaatgc aacgcgagag  11040

cgctatttta ccaacaaaga atctatactt cttttttgtt ctacaaaaat gcatcccgag  11100

agcgctattt ttctaacaaa gcatcttaga ttactttttt tctcctttgt gcgctctata  11160

atgcagtctc ttgataactt tttgcactgt aggtccgtta aggttagaag aaggctactt  11220

tggtgtctat tttctcttcc ataaaaaaag cctgactcca cttcccgcgt ttactgatta  11280

ctagcgaagc tgcgggtgca tttttttcaag ataaaggcat ccccgattat attctatacc  11340

gatgtggatt gcgcatactt tgtgaacaga aagtgatagc gttgatgatt cttcattggt  11400

cagaaaatta tgaacggttt cttctatttt gtctctatat actacgtata ggaaatgttt  11460

acattttcgt attgttttcg attcactcta tgaatagttc ttactacaat ttttttgtct  11520

aaagagtaat actagagata aacataaaaa atgtagaggt cgagtttaga tgcaagttca  11580

aggagcgaaa ggtggatggg taggttatat agggatatag cacagagata tatagcaaag  11640

agatactttt gagcaatgtt tgtggaagcg gtattcgcaa tattttagta gctcgttaca  11700

gtccggtgcg tttttggttt tttgaaagtg cgtcttcaga gcgcttttgg ttttcaaaag  11760

cgctctgaag ttcctatact ttctagagaa taggaacttc ggaataggaa cttcaaagcg  11820

tttccgaaaa cgagcgcttc cgaaaatgca acgcgagctg cgcacataca gctcactgtt  11880

cacgtcgcac ctatatctgc gtgttgcctg tatatatata tacatgagaa gaacggcata  11940

gtgcgtgttt atgcttaaat gcgtacttat atgcgtctat ttatgtagga tgaaaggtag  12000

tctagtacct cctgtgatat tatcccattc catgcggggt atcgtatgct tccttcagca  12060

ctacccttta gctgttctat atgctgccac tcctcaattg gattagtctc atccttcaat  12120

gctatcattt cctttgatat tggatcatac taagaaacca ttattatcat gacattaacc  12180

tataaaaata ggcgtatcac gaggcccttt cgtc                              12214
```

```
<210> SEQ ID NO 46
<211> LENGTH: 41
<212> TYPE: DNA
<213> ORGANISM: Saccharomyces cerevisiae

<400> SEQUENCE: 46

gcgagctcag tttatcatta tcaatactcg ccatttcaaa g                         41
```

```
<210> SEQ ID NO 47
<211> LENGTH: 46
<212> TYPE: DNA
<213> ORGANISM: Saccharomyces cerevisiae

<400> SEQUENCE: 47

cgtctagaat ccgtcgaaac taagttctgg tgttttaaaa ctaaaa                    46


<210> SEQ ID NO 48
<211> LENGTH: 44
<212> TYPE: DNA
<213> ORGANISM: Saccharomyces cerevisiae

<400> SEQUENCE: 48

gcgagctcat agcttcaaaa tgtttctact cctttttac tctt                       44


<210> SEQ ID NO 49
<211> LENGTH: 45
<212> TYPE: DNA
<213> ORGANISM: Saccharomyces cerevisiae

<400> SEQUENCE: 49

cgtctagaaa acttagatta gattgctatg ctttctttct aatga                     45


<210> SEQ ID NO 50
<211> LENGTH: 50
<212> TYPE: DNA
<213> ORGANISM: Saccharomyces cerevisiae

<400> SEQUENCE: 50

ttgcgtattg ggcgctcttc cgagctcagt ttatcattat caatactcgc                50


<210> SEQ ID NO 51
<211> LENGTH: 35
<212> TYPE: DNA
<213> ORGANISM: Saccharomyces cerevisiae

<400> SEQUENCE: 51

atggatcctc tagaatccgt cgaaactaag ttctg                                35


<210> SEQ ID NO 52
<211> LENGTH: 41
<212> TYPE: DNA
<213> ORGANISM: Saccharomyces cerevisiae

<400> SEQUENCE: 52

atgaattctc tagaaaactt agattagatt gctatgcttt c                         41


<210> SEQ ID NO 53
<211> LENGTH: 44
<212> TYPE: DNA
<213> ORGANISM: Saccharomyces cerevisiae

<400> SEQUENCE: 53

tgataatgat aaactgagct cggaagagcg cccaatacgc aaac                      44


<210> SEQ ID NO 54
<211> LENGTH: 41
<212> TYPE: DNA
<213> ORGANISM: Saccharomyces cerevisiae

<400> SEQUENCE: 54

atgaattctc tagaaaactt agattagatt gctatgcttt c                         41
```

<210> SEQ ID NO 55
<211> LENGTH: 35
<212> TYPE: DNA
<213> ORGANISM: Saccharomyces cerevisiae

<400> SEQUENCE: 55
atggatcctc tagaatccgt cgaaactaag ttctg 35

<210> SEQ ID NO 56
<211> LENGTH: 1373
<212> TYPE: DNA
<213> ORGANISM: Artificial Sequence
<220> FEATURE:
<223> OTHER INFORMATION: Construct based on S.cerevisiae promotors

<400> SEQUENCE: 56
atgaattctc tagaaaactt agattagatt gctatgcttt ctttctaatg agcaagaagt 60
aaaaaaagtt gtaatagaac aagaaaaatg aaactgaaac ttgagaaatt gaagaccgtt 120
tattaactta aatatcaatg ggaggtcatc gaaagagaaa aaaatcaaaa aaaaaatttt 180
caagaaaaag aaacgtgata aaaattttta ttgccttttt cgacgaagaa aaagaaacga 240
ggcggtctct tttttctttt ccaaaccttt agtacgggta attaacgaca ccctagagga 300
agaaagaggg gaaatttagt atgctgtgct tgggtgtttt gaagtggtac ggcgatgcgc 360
ggagtccgag aaaatctgga agagtaaaaa aggagtagaa acattttgaa gctatgagct 420
ccagcttttg ttccctttag tgagggttaa ttgcgcgctt ggcgtaatca tggtcatagc 480
tgtttcctgt gtgaaattgt tatccgctca caattccaca caacatagga gccggaagca 540
taaagtgtaa agcctggggt gcctaatgag tgaggtaact cacattaatt gcgttgcgct 600
cactgcccgc tttccagtcg ggaaacctgt cgtgccagct gcattaatga atcggccaac 660
gcgcggggag aggcggtttg cgtattgggc gctcttccga gctcagttta tcattatcaa 720
tactcgccat ttcaaagaat acgtaaataa ttaatagtag tgattttcct aactttattt 780
agtcaaaaaa ttagcctttt aattctgctg taacccgtac atgcccaaaa tagggggcgg 840
gttacacaga atatataaca tcgtaggtgt ctgggtgaac agtttattcc tggcatccac 900
taaatataat ggagcccgct ttttaagctg gcatccagaa aaaaaaagaa tcccagcacc 960
aaaatattgt tttcttcacc aaccatcagt tcataggtcc attctcttag cgcaactaca 1020
gagaacaggg gcacaaacag gcaaaaaacg ggcacaacct caatggagtg atgcaacctg 1080
cctggagtaa atgatgacac aaggcaattg acccacgcat gtatctatct cattttctta 1140
caccttctat taccttctgc tctctctgat ttggaaaaag ctgaaaaaaa aggttgaaac 1200
cagttccctg aaattattcc cctacttgac taataagtat ataaagacgg taggtattga 1260
ttgtaattct gtaaatctat ttcttaaact tcttaaattc tacttttata gttagtcttt 1320
tttttagttt taaaacacca gaacttagtt tcgacggatt ctagaggatc cat 1373

<210> SEQ ID NO 57
<211> LENGTH: 35
<212> TYPE: DNA
<213> ORGANISM: Saccharomyces cerevisiae

<400> SEQUENCE: 57
atgaattctc tagaatccgt cgaaactaag ttctg 35

<210> SEQ ID NO 58
<211> LENGTH: 48

```
<212> TYPE: DNA
<213> ORGANISM: Saccharomyces cerevisiae

<400> SEQUENCE: 58

atggatcctc tagaaaactt agattagatt gctatgcttt ctttctaa                48


<210> SEQ ID NO 59
<211> LENGTH: 10157
<212> TYPE: DNA
<213> ORGANISM: Artificial Sequence
<220> FEATURE:
<223> OTHER INFORMATION: Synthetic construct based on S.cerevisiae
      promoter

<400> SEQUENCE: 59

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat attttttat gcctcggtaa tgattttcat    360

ttttttttt cccctagcgg atgactcttt ttttttctta gcgattggca ttatcacata    420

atgaattata cattatataa agtaatgtga tttcttcgaa gaatatacta aaaaatgagc    480

aggcaagata aacgaaggca aagatgacag agcagaaagc cctagtaaag cgtattacaa    540

atgaaaccaa gattcagatt gcgatctctt taaagggtgg tcccctagcg atagagcact    600

cgatcttccc agaaaaagag gcagaagcag tagcagaaca ggccacacaa tcgcaagtga    660

ttaacgtcca cacaggtata gggtttctgg accatatgat acatgctctg gccaagcatt    720

ccggctggtc gctaatcgtt gagtgcattg gtgacttaca catagacgac catcacacca    780

ctgaagactg cgggattgct ctcggtcaag cttttaaaga ggccctactg gcgcgtggag    840

taaaaaggtt tggatcagga tttgcgcctt tggatgaggc actttccaga gcggtggtag    900

atctttcgaa caggccgtac gcagttgtcg aacttggttt gcaaagggag aaagtaggag    960

atctctcttg cgagatgatc ccgcattttc ttgaaagctt tgcagaggct agcagaatta   1020

ccctccacgt tgattgtctg cgaggcaaga atgatcatca ccgtagtgag agtgcgttca   1080

aggctcttgc ggttgccata agagaagcca cctcgcccaa tggtaccaac gatgttccct   1140

ccaccaaagg tgttcttatg tagtgacacc gattatttaa agctgcagca tacgatatat   1200

atacatgtgt atatatgtat acctatgaat gtcagtaagt atgtatacga acagtatgat   1260

actgaagatg acaaggtaat gcatcattct atacgtgtca ttctgaacga ggcgcgcttt   1320

cctttttct ttttgctttt tcttttttt tctcttgaac tcgacggatc tatgcggtgt   1380

gaaataccgc acagatgcgt aaggagaaaa taccgcatca ggaaattgta aacgttaata   1440

ttttgttaaa attcgcgtta aatttttgtt aaatcagctc attttttaac caataggccg   1500

aaatcggcaa aatcccttat aaatcaaaag aatagaccga gatagggttg agtgttgttc   1560

cagtttggaa caagagtcca ctattaaaga acgtggactc caacgtcaaa gggcgaaaaa   1620

ccgtctatca gggcgatggc ccactacgtg aaccatcacc ctaatcaagt tttttggggt   1680

cgaggtgccg taaagcacta aatcggaacc ctaaagggag cccccgattt agagcttgac   1740

ggggaaagcc ggcgaacgtg gcgagaaagg aagggaagaa agcgaaagga gcgggcgcta   1800

gggcgctggc aagtgtagcg gtcacgctgc gcgtaaccac cacacccgcc gcgcttaatg   1860
```

-continued

```
cgccgctaca gggcgcgtcg cgccattcgc cattcaggct gcgcaactgt tgggaagggc   1920
gatcggtgcg ggcctcttcg ctattacgcc agctgaattg gagcgacctc atgctatacc   1980
tgagaaagca acctgaccta caggaaagag ttactcaaga ataagaattt tcgttttaaa   2040
acctaagagt cactttaaaa tttgtataca cttatttttt ttataactta tttaataata   2100
aaaatcataa atcataagaa attcgcttat ttagaagtgt caacaacgta tctaccaacg   2160
atttgaccct tttccatctt ttcgtaaatt tctggcaagg tagacaagcc gacaaccttg   2220
attggagact tgaccaaacc tctggcgaag aattgttaat taagagctca gatcttatcg   2280
tcgtcatcct tgtaatccat cgatactagt ctagttcatt aatccatttg ctagtcttgc   2340
tcttagatcc ttcctcaata tcttccctga tggagcttta ggaatagagt cagtgaagaa   2400
cactttgttg attctcttat aaaacacaac ctgttttgac acgaattgct tgatttcatc   2460
ttcggatata tttgaatctt tcgatctcac cacaaacgca acaggaacct caccagcatc   2520
ttcttccttc atggcgacga cagcaacatc attgatttct ggatgaccta tgaggagaga   2580
ctctagctca gctggagcca cttgaaatcc tttgtacttg atgagttctt tcaatctatc   2640
cacaatgaaa agctcgtcgt catcatcgat aaatccgacg tctccagtgt gaagccaacc   2700
atctttatcg atcgtcgatg ccgtggccaa ggggtcattg agatagcctt tcatgatttg   2760
gttgccacgg atgcatattt cgccgggttt gttcctaggc aaagaatctc ctgtgtctgg   2820
atcaagtatc ttcatctcgg cgttcctcac caccgtacca catgctcctg acttcactgg   2880
aaacggctct ttagcaaacc ctaacgacat tgctagcacc ggacctgctt ctgtcatccc   2940
atagccctga ccaagcttgg cgttaggaaa cttagcacta atagcatctt caagctcctt   3000
accaagagga gctgctccag acttaaccat cctaaccgag ctcagatcat acttctccgt   3060
ctccggcgac ttcgcgatag ctaaaacgat cggtggcacg accatagcca ccgtgacttt   3120
acacctttgt atctgctcta acaagagagt gatttcgaac ttaggcatta tcaagatcgt   3180
ggcaccaact ctgagactac agagcatgat ggagttgaga gcgtatatat ggaacatagg   3240
caagacacag aggatcacgt cgtctctgtt gaagtaaaga ttcggattct cgccgtcgac   3300
ttgctgcgcc acgctcgtga ctagaccttt gtgtgttagc atcactcctt tggggagacc   3360
cgtcgtgccg gatgagaaag gaagcgccac gacgtcttct ggcgaaatct tctccggtat   3420
tgagtccact cgtggttctt cggactgagt taactcggag aaacggaggc agttttcggg   3480
gatggcgtcg gagtcggtgg tgacgatcaa aacgccgtcg ttttggaggt tcttgatttt   3540
atcgacgtaa cgggattgag tgacgatgag tttcgccgcg gaggctttgg cttgtttaga   3600
aatctccgcc ggagtgaaga acgggttcgc ggaggtggtg attgcgccga tgaaggaggc   3660
ggcaaggaaa gtgaggacta cttcaggaga gttcgggagg aggatcatta caacgtcgtg   3720
ttgcttcacg ccgaggttat gaagaccggc ggcgagtttc cgagatgtta cgtggacatc   3780
ggcgtaggtg tatacttcgc cggtgggacc gttgatcaag catggcttag cggcgaactc   3840
tgagatattt tcgaagatgt agtcgtggag tgggaggtgg ttagggatgt atatatcagg   3900
caatctcgat cggaaaatga cgtcattact acactgtttc tgatcattct gatcattgac   3960
tatcacatct tgtgtcgtca tgaattctct agaatccgtc gaaactaagt tctggtgttt   4020
taaaactaaa aaaaagacta actataaaag tagaatttaa gaagtttaag aaatagattt   4080
acagaattac aatcaatacc taccgtcttt atatacttat tagtcaagta ggggaataat   4140
ttcagggaac tggtttcaac cttttttttc agctttttcc aaatcagaga gagcagaagg   4200
taatagaagg tgtaagaaaa tgagatagat acatgcgtgg gtcaattgcc ttgtgtcatc   4260
```

```
atttactcca ggcaggttgc atcactccat tgaggttgtg cccgtttttt gcctgtttgt   4320
gcccctgttc tctgtagttg cgctaagaga atggacctat gaactgatgg ttggtgaaga   4380
aaacaatatt ttggtgctgg gattcttttt ttttctggat gccagcttaa aaagcgggct   4440
ccattatatt tagtggatgc caggaataaa ctgttcaccc agacacctac gatgttatat   4500
attctgtgta acccgccccc tattttgggc atgtacgggt tacagcagaa ttaaaaggct   4560
aatttttga ctaaataaag ttaggaaaat cactactatt aattatttac gtattctttg   4620
aaatggcgag tattgataat gataaactga gctcggaaga gcgcccaata cgcaaaccgc   4680
ctctccccgc gcgttggccg attcattaat gcagctggca cgacaggttt cccgactgga   4740
aagcgggcag tgagcgcaac gcaattaatg tgagttacct cactcattag gcaccccagg   4800
ctttacactt tatgcttccg gctcctatgt tgtgtggaat tgtgagcgga taacaatttc   4860
acacaggaaa cagctatgac catgattacg ccaagcgcgc aattaaccct cactaaaggg   4920
aacaaaagct ggagctcata gcttcaaaat gtttctactc ctttttact cttccagatt   4980
ttctcggact ccgcgcatcg ccgtaccact tcaaaacacc caagcacagc atactaaatt   5040
tcccctcttt cttcctctag ggtgtcgtta attacccgta ctaaaggttt ggaaaagaaa   5100
aaagagaccg cctcgtttct ttttcttcgt cgaaaaaggc aataaaaatt tttatcacgt   5160
ttctttttct tgaaaatttt tttttgatt tttttctctt tcgatgacct cccattgata   5220
tttaagttaa taaacggtct tcaatttctc aagtttcagt ttcatttttc ttgttctatt   5280
acaactttt ttacttcttg ctcattagaa agaaagcata gcaatctaat ctaagttttc   5340
tagaggatcc atggcatccg tagaggagtt cagaaatgca cagagggcaa aaggtccagc   5400
aaccatattg gctattggaa cagccacccc tgatcactgt gtttatcaat ctgattacgc   5460
tgattactat ttcagagtaa ctaaaagtga acatatgaca gaacttaaga aaaagtttaa   5520
tagaatttgt gataaatcta tgataaagaa aagatacata catctaactg aagaaatgtt   5580
agaggaacat ccaaatatag gtgcatatat ggcaccatct ttgaatatta gacaagaaat   5640
cataacagcc gaggtaccta gactaggtag agacgcagcc ttgaaagctt taaaggaatg   5700
gggacaacca aaatctaaga ttacacattt ggttttctgt acaacttccg gtgtcgaaat   5760
gccaggtgct gattataaac tagcaaacct attgggatta gagacctctg ttagaagagt   5820
tatgttgtat catcaaggtt gttacgccgg aggtacagtg cttagaactg ctaaggattt   5880
ggcagaaaat aacgccggtg ctagggtttt agtcgtctgc agtgaaatca ctgtcgtaac   5940
tttcagaggt ccatcagaag atgctctaga cagtttggtc ggacaagcat tgtttggcga   6000
tggatcttcc gccgtaattg taggcagcga tcctgatgtg tccattgaaa gaccactatt   6060
tcaattagtt tctgctgctc aaacttttat tccaaattcc gccggtgcca tagcaggaaa   6120
cttgagagaa gttggtttga cttttcattt gtggcctaat gtcccaacct taatttcaga   6180
aaacatcgaa aaatgcttaa ctcaagcctt tgacccattg ggcataagcg actggaactc   6240
attgttttgg attgctcatc caggtggtcc agcaatttta gacgcagtgg aggcaaaact   6300
aaacttagag aagaaaaagt tggaagctac aagacacgtt ctatcagagt atggcaacat   6360
gagctctgcc tgcgttttat tcattctaga tgagatgagg aagaagtctt taaagggtga   6420
aaaagccaca accggagaag gtttagattg ggtgttcta tttggtttcg gtcctggctt   6480
aacaattgag acagtggtgt tacactctgt tccaactgtc actaactaat gactcgagta   6540
agcttggtac cgcggctagc taagatccgc tctaaccgaa aaggaaggag ttagacaacc   6600
tgaagtctag gtccctattt attttttat agttatgtta gtattaagaa cgttatttat   6660
```

```
atttcaaatt tttctttttt ttctgtacag acgcgtgtac gcatgtaaca ttatactgaa   6720
aaccttgctt gagaaggttt tgggacgctc gaagatccag ctgcattaat gaatcggcca   6780
acgcgcgggg agaggcggtt tgcgtattgg gcgctcttcc gcttcctcgc tcactgactc   6840
gctgcgctcg gtcgttcggc tgcggcgagc ggtatcagct cactcaaagg cggtaatacg   6900
gttatccaca gaatcagggg ataacgcagg aaagaacatg tgagcaaaag gccagcaaaa   6960
ggccaggaac cgtaaaaagg ccgcgttgct ggcgtttttc cataggctcc gcccccctga   7020
cgagcatcac aaaaatcgac gctcaagtca gaggtggcga aacccgacag gactataaag   7080
ataccaggcg tttccccctg gaagctccct cgtgcgctct cctgttccga ccctgccgct   7140
taccggatac ctgtccgcct ttctcccttc gggaagcgtg gcgctttctc atagctcacg   7200
ctgtaggtat ctcagttcgg tgtaggtcgt tcgctccaag ctgggctgtg tgcacgaacc   7260
ccccgttcag cccgaccgct gcgccttatc cggtaactat cgtcttgagt ccaacccggt   7320
aagacacgac ttatcgccac tggcagcagc cactggtaac aggattagca gagcgaggta   7380
tgtaggcggt gctacagagt tcttgaagtg gtggcctaac tacggctaca ctagaaggac   7440
agtatttggt atctgcgctc tgctgaagcc agttaccttc ggaaaaagag ttggtagctc   7500
ttgatccggc aaacaaacca ccgctggtag cggtggtttt tttgtttgca agcagcagat   7560
tacgcgcaga aaaaaaggat ctcaagaaga tcctttgatc ttttctacgg ggtctgacgc   7620
tcagtggaac gaaaactcac gttaagggat tttggtcatg agattatcaa aaaggatctt   7680
cacctagatc cttttaaatt aaaaatgaag ttttaaatca atctaaagta tatatgagta   7740
aacttggtct gacagttacc aatgcttaat cagtgaggca cctatctcag cgatctgtct   7800
atttcgttca tccatagttg cctgactccc cgtcgtgtag ataactacga tacgggaggg   7860
cttaccatct ggccccagtg ctgcaatgat accgcgagac ccacgctcac cggctccaga   7920
tttatcagca ataaaccagc cagccggaag ggccgagcgc agaagtggtc ctgcaacttt   7980
atccgcctcc atccagtcta ttaattgttg ccgggaagct agagtaagta gttcgccagt   8040
taatagtttg cgcaacgttg ttgccattgc tacaggcatc gtggtgtcac gctcgtcgtt   8100
tggtatggct tcattcagct ccggttccca acgatcaagg cgagttacat gatcccccat   8160
gttgtgcaaa aaagcggtta gctccttcgg tcctccgatc gttgtcagaa gtaagttggc   8220
cgcagtgtta tcactcatgg ttatggcagc actgcataat tctcttactg tcatgccatc   8280
cgtaagatgc ttttctgtga ctggtgagta ctcaaccaag tcattctgag aatagtgtat   8340
gcggcgaccg agttgctctt gcccggcgtc aatacgggat aataccgcgc cacatagcag   8400
aactttaaaa gtgctcatca ttggaaaacg ttcttcgggg cgaaaactct caaggatctt   8460
accgctgttg agatccagtt cgatgtaacc cactcgtgca cccaactgat cttcagcatc   8520
ttttactttc accagcgttt ctgggtgagc aaaaacagga aggcaaaatg ccgcaaaaaa   8580
gggaataagg gcgacacgga aatgttgaat actcatactc ttcctttttc aatattattg   8640
aagcatttat cagggttatt gtctcatgag cggatacata tttgaatgta tttagaaaaa   8700
taaacaaata ggggttccgc gcacatttcc ccgaaaagtg ccacctgaac gaagcatctg   8760
tgcttcattt tgtagaacaa aaatgcaacg cgagagcgct aatttttcaa acaaagaatc   8820
tgagctgcat ttttacagaa cagaaatgca acgcgaaagc gctattttac caacgaagaa   8880
tctgtgcttc atttttgtaa aacaaaaatg caacgcgaga gcgctaattt ttcaaacaaa   8940
gaatctgagc tgcattttta cagaacagaa atgcaacgcg agagcgctat tttaccaaca   9000
aagaatctat acttcttttt tgttctacaa aaatgcatcc cgagagcgct atttttctaa   9060
```

```
caaagcatct tagattactt tttttctcct ttgtgcgctc tataatgcag tctcttgata   9120

actttttgca ctgtaggtcc gttaaggtta gaagaaggct actttggtgt ctattttctc   9180

ttccataaaa aaagcctgac tccacttccc gcgtttactg attactagcg aagctgcggg   9240

tgcatttttt caagataaag gcatccccga ttatattcta taccgatgtg gattgcgcat   9300

actttgtgaa cagaaagtga tagcgttgat gattcttcat tggtcagaaa attatgaacg   9360

gtttcttcta ttttgtctct atatactacg tataggaaat gtttacattt tcgtattgtt   9420

ttcgattcac tctatgaata gttcttacta caattttttt gtctaaagag taatactaga   9480

gataaacata aaaaatgtag aggtcgagtt tagatgcaag ttcaaggagc gaaaggtgga   9540

tgggtaggtt atatagggat atagcacaga gatatatagc aaagagatac ttttgagcaa   9600

tgtttgtgga agcggtattc gcaatatttt agtagctcgt tacagtccgg tgcgtttttg   9660

gtttttttgaa agtgcgtctt cagagcgctt ttggttttca aaagcgctct gaagttccta   9720

tactttctag agaataggaa cttcggaata ggaacttcaa agcgtttccg aaaacgagcg   9780

cttccgaaaa tgcaacgcga gctgcgcaca tacagctcac tgttcacgtc gcacctatat   9840

ctgcgtgttg cctgtatata tatatacatg agaagaacgg catagtgcgt gtttatgctt   9900

aaatgcgtac ttatatgcgt ctatttatgt aggatgaaag gtagtctagt acctcctgtg   9960

atattatccc attccatgcg gggtatcgta tgcttccttc agcactaccc tttagctgtt  10020

ctatatgctg ccactcctca attggattag tctcatcctt caatgctatc atttcctttg  10080

atattggatc atctaagaaa ccattattat catgacatta acctataaaa ataggcgtat  10140

cacgaggccc tttcgtc                                                 10157
```

<210> SEQ ID NO 60
<211> LENGTH: 28
<212> TYPE: DNA
<213> ORGANISM: Artificial Sequence
<220> FEATURE:
<223> OTHER INFORMATION: Synthetic primer

<400> SEQUENCE: 60

```
tcgacggatc tatgcggtgt gaaatacc                                        28
```

<210> SEQ ID NO 61
<211> LENGTH: 28
<212> TYPE: DNA
<213> ORGANISM: Artificial Sequence
<220> FEATURE:
<223> OTHER INFORMATION: Synthetic primer

<400> SEQUENCE: 61

```
actctcagta caatctgctc tgatgccg                                        28
```

<210> SEQ ID NO 62
<211> LENGTH: 48
<212> TYPE: DNA
<213> ORGANISM: Artificial Sequence
<220> FEATURE:
<223> OTHER INFORMATION: Synthetic primer

<400> SEQUENCE: 62

```
agagcagatt gtactgagag tcatcagagc agattgtact gagagtgc                  48
```

<210> SEQ ID NO 63
<211> LENGTH: 47
<212> TYPE: DNA
<213> ORGANISM: Artificial Sequence
<220> FEATURE:

<223> OTHER INFORMATION: Synthetic primer

<400> SEQUENCE: 63
cacaccgcat agatccgtcg aggattttgc cgatttcggc ctattgg 47

<210> SEQ ID NO 64
<211> LENGTH: 10265
<212> TYPE: DNA
<213> ORGANISM: Artificial Sequence
<220> FEATURE:
<223> OTHER INFORMATION: Synthetic construct vector

<400> SEQUENCE: 64
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtca 180
tcagagcaga ttgtactgag agtgcaccat accacagctt ttcaattcaa ttcatcattt 240
tttttttatt cttttttttg atttcggttt ctttgaaatt tttttgattc ggtaatctcc 300
gaacagaagg aagaacgaag gaaggagcac agacttagat tggtatatat acgcatatgt 360
agtgttgaag aaacatgaaa ttgcccagta ttcttaaccc aactgcacag aacaaaaacc 420
tgcaggaaac gaagataaat catgtcgaaa gctacatata aggaacgtgc tgctactcat 480
cctagtcctg ttgctgccaa gctatttaat atcatgcacg aaaagcaaac aaacttgtgt 540
gcttcattgg atgttcgtac caccaaggaa ttactggagt tagttgaagc attaggtccc 600
aaaatttgtt tactaaaaac acatgtggat atcttgactg atttttccat ggagggcaca 660
gttaagccgc taaaggcatt atccgccaag tacaattttt tactcttcga agacagaaaa 720
tttgctgaca ttggtaatac agtcaaattg cagtactctg cgggtgtata cagaatagca 780
gaatgggcag acattacgaa tgcacacggt gtggtgggcc caggtattgt tagcggtttg 840
aagcaggcgg cagaagaagt aacaaaggaa cctagaggcc ttttgatgtt agcagaattg 900
tcatgcaagg gctccctatc tactggagaa tatactaagg gtactgttga cattgcgaag 960
agcgacaaag attttgttat cggctttatt gctcaaagag acatgggtgg aagagatgaa 1020
ggttacgatt ggttgattat gacacccggt gtgggtttag atgacaaggg agacgcattg 1080
ggtcaacagt atagaaccgt ggatgatgtg gtctctacag gatctgacat tattattgtt 1140
ggaagaggac tatttgcaaa gggaagggat gctaaggtag agggtgaacg ttacagaaaa 1200
gcaggctggg aagcatattt gagaagatgc ggccagcaaa actaaaaaac tgtattataa 1260
gtaaatgcat gtatactaaa ctcacaaatt agagcttcaa tttaattata tcagttatta 1320
ccctatgcgg tgtgaaatac cgcacagatg cgtaaggaga aaataccgca tcaggaaatt 1380
gtaaacgtta atattttgtt aaaattcgcg ttaaattttt gttaaatcag ctcatttttt 1440
aaccaatagg ccgaaatcgg caaaatcctc gacggatcta tgcggtgtga aataccgcac 1500
agatgcgtaa ggagaaaata ccgcatcagg aaattgtaaa cgttaatatt ttgttaaaat 1560
tcgcgttaaa tttttgttaa atcagctcat tttttaacca ataggccgaa atcggcaaaa 1620
tcccttataa atcaaaagaa tagaccgaga tagggttgag tgttgttcca gtttggaaca 1680
agagtccact attaaagaac gtggactcca acgtcaaagg gcgaaaaacc gtctatcagg 1740
gcgatggccc actacgtgaa ccatcaccct aatcaagttt tttggggtcg aggtgccgta 1800
aagcactaaa tcggaaccct aaagggagcc cccgatttag agcttgacgg ggaaagccgg 1860
cgaacgtggc gagaaaggaa gggaagaaag cgaaaggagc gggcgctagg gcgctggcaa 1920

-continued

```
gtgtagcggt cacgctgcgc gtaaccacca cacccgccgc gcttaatgcg ccgctacagg   1980
gcgcgtcgcg ccattcgcca ttcaggctgc gcaactgttg ggaagggcga tcggtgcggg   2040
cctcttcgct attacgccag ctgaattgga gcgacctcat gctatacctg agaaagcaac   2100
ctgacctaca ggaaagagtt actcaagaat aagaattttc gttttaaaac ctaagagtca   2160
ctttaaaatt tgtatacact tatttttttt ataacttatt taataataaa aatcataaat   2220
cataagaaat tcgcttattt agaagtgtca acaacgtatc taccaacgat ttgacccttt   2280
tccatctttt cgtaaatttc tggcaaggta gacaagccga caaccttgat tggagacttg   2340
accaaacctc tggcgaagaa ttgttaatta agagctcaga tcttatcgtc gtcatccttg   2400
taatccatcg atactagtct agttcattaa tccatttgct agtcttgctc ttagatcctt   2460
cctcaatatc ttccctgatg gagctttagg aatagagtca gtgaagaaca ctttgttgat   2520
tctcttataa aacacaacct gttttgacac gaattgcttg atttcatctt cggatatatt   2580
tgaatctttc gatctcacca caaacgcaac aggaacctca ccagcatctt cttccttcat   2640
ggcgacgaca gcaacatcat tgatttctgg atgacctatg aggagagact ctagctcagc   2700
tggagccact tgaaatcctt tgtacttgat gagttctttc aatctatcca caatgaaaag   2760
ctcgtcgtca tcatcgataa atccgacgtc tccagtgtga agccaaccat ctttatcgat   2820
cgtcgatgcc gtggccaagg ggtcattgag atagcctttc atgatttggt tgccacggat   2880
gcatatttcg ccgggtttgt tcctaggcaa agaatctcct gtgtctggat caagtatctt   2940
catctcggcg ttcctcacca ccgtaccaca tgctcctgac ttcactggaa acggctcttt   3000
agcaaaccct aacgacattg ctagcaccgg acctgcttct gtcatcccat agccctgacc   3060
aagcttggcg ttaggaaact tagcactaat agcatcttca agctccttac caagaggagc   3120
tgctccagac ttaaccatcc taaccgagct cagatcatac ttctccgtct ccggcgactt   3180
cgcgatagct aaaacgatcg gtggcacgac catagccacc gtgactttac acctttgtat   3240
ctgctctaac aagagagtga tttcgaactt aggcattatc aagatcgtgg caccaactct   3300
gagactacag agcatgatgg agttgagagc gtatatatgg aacataggca agacacagag   3360
gatcacgtcg tctctgttga agtaaagatt cggattctcg ccgtcgactt gctgcgccac   3420
gctcgtgact agacctttgt gtgttagcat cactcctttg gggagacccg tcgtgccgga   3480
tgagaaagga agcgccacga cgtcttctgg cgaaatcttc tccggtattg agtccactcg   3540
tggttcttcg gactgagtta actcggagaa acggaggcag ttttcgggga tggcgtcgga   3600
gtcggtggtg acgatcaaaa cgccgtcgtt ttggaggttc ttgattttat cgacgtaacg   3660
ggattgagtg acgatgagtt tcgccgcgga ggctttggct tgtttagaaa tctccgccgg   3720
agtgaagaac gggttcgcgg aggtggtgat tgcgccgatg aaggaggcgg caaggaaagt   3780
gaggactact tcaggagagt tcgggaggag gatcattaca acgtcgtgtt gcttcacgcc   3840
gaggttatga agaccggcgg cgagtttccg agatgttacg tggacatcgg cgtaggtgta   3900
tacttcgccg gtgggaccgt tgatcaagca tggcttagcg gcgaactctg agatattttc   3960
gaagatgtag tcgtggagtg ggaggtggtt agggatgtat atatcaggca atctcgatcg   4020
gaaaatgacg tcattactac actgtttctg atcattctga tcattgacta tcacatcttg   4080
tgtcgtcatg aattctctag aatccgtcga aactaagttc tggtgtttta aaactaaaaa   4140
aaagactaac tataaaagta gaatttaaga agtttaagaa atagatttac agaattacaa   4200
tcaataccta ccgtctttat atacttatta gtcaagtagg ggaataattt cagggaactg   4260
gtttcaacct tttttttcag ctttttccaa atcagagaga gcagaaggta atagaaggtg   4320
```

```
taagaaaatg agatagatac atgcgtgggt caattgcctt gtgtcatcat ttactccagg   4380
caggttgcat cactccattg aggttgtgcc cgttttttgc ctgtttgtgc ccctgttctc   4440
tgtagttgcg ctaagagaat ggacctatga actgatggtt ggtgaagaaa acaatatttt   4500
ggtgctggga ttcttttttt ttctggatgc cagcttaaaa agcgggctcc attatattta   4560
gtggatgcca ggaataaact gttcacccag acacctacga tgttatatat tctgtgtaac   4620
ccgcccccta ttttgggcat gtacgggtta cagcagaatt aaaaggctaa tttttttgact   4680
aaataaagtt aggaaaatca ctactattaa ttatttacgt attctttgaa atggcgagta   4740
ttgataatga taaactgagc tcggaagagc gcccaatacg caaaccgcct ctccccgcgc   4800
gttggccgat tcattaatgc agctggcacg acaggtttcc cgactggaaa gcgggcagtg   4860
agcgcaacgc aattaatgtg agttacctca ctcattaggc accccaggct ttacacttta   4920
tgcttccggc tcctatgttg tgtggaattg tgagcggata acaatttcac acaggaaaca   4980
gctatgacca tgattacgcc aagcgcgcaa ttaaccctca ctaaagggaa caaaagctgg   5040
agctcatagc ttcaaaatgt ttctactcct tttttactct tccagatttt ctcggactcc   5100
gcgcatcgcc gtaccacttc aaaacaccca agcacagcat actaaatttc ccctctttct   5160
tcctctaggg tgtcgttaat tacccgtact aaaggtttgg aaaagaaaaa agagaccgcc   5220
tcgtttcttt ttcttcgtcg aaaaaggcaa taaaaatttt tatcacgttt ctttttcttg   5280
aaaatttttt ttttgatttt tttctctttc gatgacctcc cattgatatt taagttaata   5340
aacggtcttc aatttctcaa gtttcagttt catttttctt gttctattac aacttttttt   5400
acttcttgct cattagaaag aaagcatagc aatctaatct aagttttcta gaggatccat   5460
ggcatccgta gaggagttca gaaatgcaca gagggcaaaa ggtccagcaa ccatattggc   5520
tattggaaca gccacccctg atcactgtgt ttatcaatct gattacgctg attactattt   5580
cagagtaact aaaagtgaac atatgacaga acttaagaaa aagtttaata gaatttgtga   5640
taaatctatg ataaagaaaa gatacataca tctaactgaa gaaatgttag aggaacatcc   5700
aaatataggt gcatatatgg caccatcttt gaatattaga caagaaatca taacagccga   5760
ggtacctaga ctaggtagag acgcagcctt gaaagcttta aaggaatggg gacaaccaaa   5820
atctaagatt acacatttgg ttttctgtac aacttccggt gtcgaaatgc caggtgctga   5880
ttataaacta gcaaacctat tgggattaga gacctctgtt agaagagtta tgttgtatca   5940
tcaaggttgt tacgccggag gtacagtgct tagaactgct aaggatttgg cagaaaataa   6000
cgccggtgct agggttttag tcgtctgcag tgaaatcact gtcgtaactt tcagaggtcc   6060
atcagaagat gctctagaca gtttggtcgg acaagcattg tttggcgatg gatcttccgc   6120
cgtaattgta ggcagcgatc ctgatgtgtc cattgaaaga ccactatttc aattagtttc   6180
tgctgctcaa acttttattc caaattccgc cggtgccata gcaggaaact tgagagaagt   6240
tggtttgact tttcatttgt ggcctaatgt cccaacctta atttcagaaa acatcgaaaa   6300
atgcttaact caagcctttg acccattggg cataagcgac tggaactcat tgttttggat   6360
tgctcatcca ggtggtccag caattttaga cgcagtggag gcaaaactaa acttagagaa   6420
gaaaaagttg gaagctacaa gacacgttct atcagagtat ggcaacatga gctctgcctg   6480
cgttttattc attctagatg agatgaggaa gaagtcttta aagggtgaaa aagccacaac   6540
cggagaaggt ttagattggg gtgttctatt tggtttcggt cctggcttaa caattgagac   6600
agtggtgtta cactctgttc caactgtcac taactaatga ctcgagtaag cttggtaccg   6660
cggctagcta agatccgctc taaccgaaaa ggaaggagtt agacaacctg aagtctaggt   6720
```

```
ccctatttat ttttttatag ttatgttagt attaagaacg ttatttatat ttcaaatttt   6780
tcttttttt ctgtacagac gcgtgtacgc atgtaacatt atactgaaaa ccttgcttga   6840
gaaggttttg ggacgctcga agatccagct gcattaatga atcggccaac gcgcggggag   6900
aggcggtttg cgtattgggc gctcttccgc ttcctcgctc actgactcgc tgcgctcggt   6960
cgttcggctg cggcgagcgg tatcagctca ctcaaaggcg gtaatacggt tatccacaga   7020
atcaggggat aacgcaggaa agaacatgtg agcaaaaggc cagcaaaagg ccaggaaccg   7080
taaaaaggcc gcgttgctgg cgtttttcca taggctccgc ccccctgacg agcatcacaa   7140
aaatcgacgc tcaagtcaga ggtggcgaaa cccgacagga ctataaagat accaggcgtt   7200
tccccctgga agctccctcg tgcgctctcc tgttccgacc ctgccgctta ccggatacct   7260
gtccgccttt ctcccttcgg gaagcgtggc gctttctcat agctcacgct gtaggtatct   7320
cagttcggtg taggtcgttc gctccaagct gggctgtgtg cacgaacccc ccgttcagcc   7380
cgaccgctgc gccttatccg gtaactatcg tcttgagtcc aacccggtaa gacacgactt   7440
atcgccactg gcagcagcca ctggtaacag gattagcaga gcgaggtatg taggcggtgc   7500
tacagagttc ttgaagtggt ggcctaacta cggctacact agaaggacag tatttggtat   7560
ctgcgctctg ctgaagccag ttaccttcgg aaaaagagtt ggtagctctt gatccggcaa   7620
acaaaccacc gctggtagcg gtggtttttt tgtttgcaag cagcagatta cgcgcagaaa   7680
aaaaggatct caagaagatc ctttgatctt ttctacgggg tctgacgctc agtggaacga   7740
aaactcacgt taagggattt tggtcatgag attatcaaaa aggatcttca cctagatcct   7800
tttaaattaa aaatgaagtt ttaaatcaat ctaaagtata tatgagtaaa cttggtctga   7860
cagttaccaa tgcttaatca gtgaggcacc tatctcagcg atctgtctat ttcgttcatc   7920
catagttgcc tgactccccg tcgtgtagat aactacgata cgggagggct taccatctgg   7980
ccccagtgct gcaatgatac cgcgagaccc acgctcaccg gctccagatt tatcagcaat   8040
aaaccagcca gccggaaggg ccgagcgcag aagtggtcct gcaactttat ccgcctccat   8100
ccagtctatt aattgttgcc gggaagctag agtaagtagt tcgccagtta atagtttgcg   8160
caacgttgtt gccattgcta caggcatcgt ggtgtcacgc tcgtcgtttg gtatggcttc   8220
attcagctcc ggttcccaac gatcaaggcg agttacatga tcccccatgt tgtgcaaaaa   8280
agcggttagc tccttcggtc ctccgatcgt tgtcagaagt aagttggccg cagtgttatc   8340
actcatggtt atggcagcac tgcataattc tcttactgtc atgccatccg taagatgctt   8400
ttctgtgact ggtgagtact caaccaagtc attctgagaa tagtgtatgc ggcgaccgag   8460
ttgctcttgc ccggcgtcaa tacgggataa taccgcgcca catagcagaa ctttaaaagt   8520
gctcatcatt ggaaaacgtt cttcggggcg aaaactctca aggatcttac cgctgttgag   8580
atccagttcg atgtaaccca ctcgtgcacc caactgatct tcagcatctt ttactttcac   8640
cagcgtttct gggtgagcaa aaacaggaag gcaaaatgcc gcaaaaaagg gaataagggc   8700
gacacggaaa tgttgaatac tcatactctt cctttttcaa tattattgaa gcatttatca   8760
gggttattgt ctcatgagcg gatacatatt tgaatgtatt tagaaaaata aacaaatagg   8820
ggttccgcgc acatttcccc gaaaagtgcc acctgaacga agcatctgtg cttcattttg   8880
tagaacaaaa atgcaacgcg agagcgctaa tttttcaaac aaagaatctg agctgcattt   8940
ttacagaaca gaaatgcaac gcgaaagcgc tattttacca acgaagaatc tgtgcttcat   9000
ttttgtaaaa caaaaatgca acgcgagagc gctaattttt caaacaaaga atctgagctg   9060
catttttaca gaacagaaat gcaacgcgag agcgctattt taccaacaaa gaatctatac   9120
```

```
ttcttttttg ttctacaaaa atgcatcccg agagcgctat ttttctaaca aagcatctta   9180

gattactttt tttctccttt gtgcgctcta taatgcagtc tcttgataac tttttgcact   9240

gtaggtccgt taaggttaga agaaggctac tttggtgtct attttctctt ccataaaaaa   9300

agcctgactc cacttcccgc gtttactgat tactagcgaa gctgcgggtg catttttttca   9360

agataaaggc atccccgatt atattctata ccgatgtgga ttgcgcatac tttgtgaaca   9420

gaaagtgata gcgttgatga ttcttcattg gtcagaaaat tatgaacggt ttcttctatt   9480

ttgtctctat atactacgta taggaaatgt ttacattttc gtattgtttt cgattcactc   9540

tatgaatagt tcttactaca attttttttgt ctaaagagta atactagaga taaacataaa   9600

aaatgtagag gtcgagttta gatgcaagtt caaggagcga aaggtggatg ggtaggttat   9660

atagggatat agcacagaga tatatagcaa agagatactt ttgagcaatg tttgtggaag   9720

cggtattcgc aatattttag tagctcgtta cagtccggtg cgtttttggt tttttgaaag   9780

tgcgtcttca gagcgctttt ggttttcaaa agcgctctga agttcctata ctttctagag   9840

aataggaact tcggaatagg aacttcaaag cgtttccgaa aacgagcgct tccgaaaatg   9900

caacgcgagc tgcgcacata cagctcactg ttcacgtcgc acctatatct gcgtgttgcc   9960

tgtatatata tatacatgag aagaacggca tagtgcgtgt ttatgcttaa atgcgtactt  10020

atatgcgtct atttatgtag gatgaaaggt agtctagtac ctcctgtgat attatcccat  10080

tccatgcggg gtatcgtatg cttccttcag cactaccctt tagctgttct atatgctgcc  10140

actcctcaat tggattagtc tcatccttca atgctatcat ttcctttgat attggatcat  10200

ctaagaaacc attattatca tgacattaac ctataaaaat aggcgtatca cgaggccctt  10260

tcgtc                                                              10265
```

<210> SEQ ID NO 65
<211> LENGTH: 50
<212> TYPE: DNA
<213> ORGANISM: Saccharomyces cerevisiae

<400> SEQUENCE: 65

```
ttccagcaat aacaaatcca ttttgtatct agaaaactta gattagattg              50
```

<210> SEQ ID NO 66
<211> LENGTH: 50
<212> TYPE: DNA
<213> ORGANISM: Saccharomyces cerevisiae

<400> SEQUENCE: 66

```
cattgcttca atttggtcca ttttgtatct agaatccgtc gaaactaagt              50
```

<210> SEQ ID NO 67
<211> LENGTH: 12806
<212> TYPE: DNA
<213> ORGANISM: Artificial Sequence
<220> FEATURE:
<223> OTHER INFORMATION: Synthetic vector construct

<400> SEQUENCE: 67

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataccac agcttttcaa ttcaattcat catttttttt ttattctttt ttttgatttc    240

ggtttctttg aaattttttt gattcggtaa tctccgaaca gaaggaagaa cgaaggaagg    300
```

-continued

```
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtccat tcgccattca ggctgcgcaa ctgttgggaa gggcgatcgg tgcgggcctc   1860
ttcgctatta cgccagctga attggagcga cctcatgcta tacctgagaa agcaacctga   1920
cctacaggaa agagttactc aagaataaga attttcgttt taaaacctaa gagtcacttt   1980
aaaatttgta tacacttatt ttttttataa cttatttaat aataaaaatc ataaatcata   2040
agaaattcgc ttatttagaa gtgtcaacaa cgtatctacc aacgatttga cccttttcca   2100
tcttttcgta aatttctggc aaggtagaca agccgacaac cttgattgga gacttgacca   2160
aacctctggc gaagaattgt taattaagag ctcagatctt tagcagattg gaataggtgc   2220
accattccac tctttcaagc aatccataag tggatctatc aactttccct cgcacatagc   2280
tgtgaatacc ttgtcaaatt cttcacctgg gctaacgact ttttcaccag ttagtaattt   2340
ggttcccaac tcttctctaa cgaatctgta caaagggtac gacctacact ctttgattct   2400
atttggtata ggggcagtac catttccgta tgcggctcta gcagcttcga cttcctttgg   2460
taaaactgcc ttcagttctt cttcaaaggc acctatcttt tggaatattg aagtaacggc   2520
atttttctca gtttcaccat tggataaagc gtgatctaca ataacttgtc tcaatctctg   2580
catcaatgga taagtagcgc tacatggatc gtcaacgtaa gtaaatactt gttctctatc   2640
tacaactttt aataaatctt tttcacagaa tcttgatggg tgcaattcac cattgatacc   2700
```

-continued

```
tgtagttaga accttttttg caacctgtga tacggtattt ttcactgtct gtctcaaatt   2760

ctcttccaag tgtctcaaat ctacggcctg gcatataccc actaaaaatg ttgtggacat   2820

taatttaagg atatcaacgg cctcgcttgt tttcttgat gaaatcaggc ccaaagaatt    2880

aacatcctga ttgtgttgtt cggctgattg tacatgagag gttactgggt tggctagata   2940

ttgcagctct gaacaatagc ttgccattgc tatctcagca cctttgaaac cataatcaag   3000

actagggtta gaagatgcgg tcagattcga aggcaaaccg ttattgtaga agtcattgac   3060

caattcagaa aattgggcaa acattaattt gccaattgcg gctatggcaa gcctggtatt   3120

atccatactg actcctatgg gtgtaccctg gaaattgcct ccatgtattg ccttattcct   3180

cgacacatca ataagtggat tatcgttaac agagttgatc tctctttcta tagactttgt   3240

agcttgtcta attacttcaa tttgagggcc aagccattgt ggggatgtcc ttaaagcata   3300

tctatcttgt ttgggttttt gcaaagggtc catttcatga accttctggg ctaacttcat   3360

gtagctagag ccgtccaaaa tgtgctccat gatagctgct gcttcaattt gtcctgggtg   3420

atgttttaac ctgtgggtca agtgatcagt aaactcaggt tttccactca tgacttcggc   3480

aaaaattgcg gacaaaactt cggccaaaac tgcttgtacg ttagcttcaa acaacaccat   3540

ggatgccata ccgctgccga cagcggtgcc attcaccagg gctaaacctt ccttgggttg   3600

caaatcaaag aaaccagttg aaataccagc tttctcaaat gcttccttag cggttaagga   3660

ttctccgtct ggaccagtgg cctttgaatt aggtcttccc gttaataagc ctgcgatata   3720

tgaaagggga accaaatcac cgctggcagt tattgttcct cttaagggca acgaaggaga   3780

aatgttgtgg ttcaatagtg aagtgatggc ctcaagaatt tcaaacctta ttccagagta   3840

accttgcaac aaagtgttca ccctaacaag catagcagct cttgttgccg attggggtaa   3900

tgtatggcaa gtttcctttg tattaccgaa aataccggcg ttaaggaatc tgatcagttc   3960

tgtttgcaaa gcagtgccat ttttagttct tctatgagag gtagcaccaa agcctgtggt   4020

aacgccatag gaatctgtgc ccttgttcat actttccatg acccaatctg atgaagcctt   4080

aactccggct ctacttgttt ctgcaagttc taccttcact gaaccgccaa cggtcgaaat   4140

agcagctacc tgtcctatcg tcaatgtctc gccgcctaga tttacgactg gtcttctgta   4200

ttcctcaacc atcttcttaa cttcatccag atggctacct ttcatctggt cagctgccag   4260

accccaattc aaaggatctg caagagtttt tgtcgttacg gccaccttgg tcttttcacc   4320

accaccgcat agcattgctt caatttggtc cattttgtat ctagaatccg tcgaaactaa   4380

gttctggtgt tttaaaacta aaaaaaagac taactataaa agtagaattt aagaagttta   4440

agaaatagat ttacagaatt acaatcaata cctaccgtct ttatatactt attagtcaag   4500

taggggaata atttcagga actggtttca accttttttt tcagcttttt ccaaatcaga    4560

gagagcagaa ggtaatagaa ggtgtaagaa aatgagatag atacatgcgt gggtcaattg   4620

ccttgtgtca tcatttactc caggcaggtt gcatcactcc attgaggttg tgcccgtttt   4680

ttgcctgttt gtgcccctgt tctctgtagt tgcgctaaga gaatggacct atgaactgat   4740

ggttggtgaa gaaaacaata ttttggtgct gggattcttt ttttttctgg atgccagctt   4800

aaaaagcggg ctccattata tttagtggat gccaggaata aactgttcac ccagacacct   4860

acgatgttat atattctgtg taacccgccc cctattttgg gcatgtacgg gttacagcag   4920

aattaaaagg ctaatttttt gactaaataa agttaggaaa atcactacta ttaattattt   4980

acgtattctt tgaaatggcg agtattgata atgataaact gagctcggaa gagcgcccaa   5040

tacgcaaacc gcctctcccc gcgcgttggc cgattcatta atgcagctgg cacgacaggt   5100
```

-continued

```
ttcccgactg gaaagcgggc agtgagcgca acgcaattaa tgtgagttac ctcactcatt   5160
aggcacccca ggctttacac tttatgcttc cggctcctat gttgtgtgga attgtgagcg   5220
gataacaatt tcacacagga aacagctatg accatgatta cgccaagcgc gcaattaacc   5280
ctcactaaag ggaacaaaag ctggagctca tagcttcaaa atgtttctac tccttttta   5340
ctcttccaga ttttctcgga ctccgcgcat cgccgtacca cttcaaaaca cccaagcaca   5400
gcatactaaa tttcccctct ttcttcctct agggtgtcgt taattacccg tactaaaggt   5460
ttggaaaaga aaaaagagac cgcctcgttt ctttttcttc gtcgaaaaag gcaataaaaa   5520
tttttatcac gtttcttttt cttgaaaatt ttttttttga tttttttctc tttcgatgac   5580
ctcccattga tatttaagtt aataaacggt cttcaatttc tcaagtttca gtttcatttt   5640
tcttgttcta ttacaacttt ttttacttct tgctcattag aaagaaagca tagcaatcta   5700
atctaagttt tctagataca aaatggattt gttattgctg gaaaagtcac ttattgctgt   5760
atttgtggca gttattctag ccacggttat ttctaaatta agaggtaaga aactaaaact   5820
acctcctggt cccatcccca taccaatttt tggtaattgg ttgcaagtgg gcgatgattt   5880
gaatcacaga aatttggtag actatgctaa gaagttcggt gacctttttct tgcttagaat   5940
gggtcaaagg aatttggtag tggttagctc acctgatttg actaaggagg tcttattaac   6000
gcaaggcgtt gagtttggct ccagaactag aaatgttgtg tttgatattt tcactggtaa   6060
aggtcaagat atggttttta cagtttacgg tgagcactgg agaaaaatga gaagaatcat   6120
gaccgtacca ttctttacta acaaggttgt tcaacaaaat agagaaggtt gggagtttga   6180
ggcagcttcc gtagtggaag acgtaaagaa aaatccagat tcggccacaa agggtatagt   6240
actaagaaaa agactacaat tgatgatgta caacaatatg ttcagaatta tgtttgacag   6300
aagatttgaa agtgaagatg accctttgtt cctgagactt aaggctttga atggtgaaag   6360
atcgagattg gctcaaagtt tcgaatataa ttacggtgac tttattccaa tcttaagacc   6420
atttttgaga ggctatttga aaatttgcca agacgtcaag gataggagga tcgctctttt   6480
caagaagtac tttgtggacg agagaaagca aatagcttct tccaagccca caggttcgga   6540
aggtttaaaa tgtgcaattg atcatatttt agaagctgaa caaaaaggtg aaattaacga   6600
agataatgtt ttgtacattg tagaaaatat caatgtggct gcaatagaaa caaccttatg   6660
gtcaatagaa tggggtattg ctgaattggt gaatcaccca gaaatacaat ctaaactgag   6720
aaacgagcta gataccgttt taggtccagg tgtccaagtt acagaacctg atttgcataa   6780
gttaccctac ttgcaagctg tggttaaaga aaccttgaga ttgagaatgg ctattcctct   6840
tctagttcct catatgaacc tacatgatgc taaactggcc ggttatgata ttccagcaga   6900
aagtaagatt ttagtaaatg catggtggtt ggccaacaat ccaaacagtt ggaaaaagcc   6960
tgaagaattc agacctgaaa gattcttcga agaggaatct catgttgaag ccaacggaaa   7020
tgacttcaga tatgtacctt ttggcgttgg cagaagatcg tgtccaggaa taatactagc   7080
cttaccaata ttgggtatca caattggtag gatggttcaa aattttgagt tgctaccacc   7140
acccggacaa tcgaaagtcg atacttcaga gaaaggagga caattctcat tgcatatttt   7200
gaatcattcc attatagtca tgaaacccag aaattgtcca tctactccat ctactccatc   7260
tactccatct actaggagga gcggttcggg caattcaaag agggttgaac cactaaagcc   7320
attagttatc aaacctagag aagaggaaat tgacgatgga aggaagaaag tcactatatt   7380
cttcggcacc caaacaggta cagctgaagg ttttgctaag gctctaggag aagaagcaaa   7440
agctagatat gaaaagacga gattcaaaat tgtcgatctg gatgactatg ccgccgatga   7500
```

-continued

```
tgacgaatac gaagaaaaat tgaagaaaga agatgtcgca tttttcttcc ttgccaccta   7560
cggcgacggt gaaccaacag ataatgccgc aaggttttac aagtggttta ctgaaggtaa   7620
tgacagagga gaatggctga agaatttgaa atatggtgtg ttcggccttg gtaacagaca   7680
gtacgagcat tttaataagg tcgctaaggt tgtagatgat atacttgttg aacaaggtgc   7740
tcaaaggtta gtgcaggtgg gcttgggtga cgatgatcaa tgtattgaag atgactttac   7800
tgcttggaga gaagccttgt ggcctgaatt agatactatc cttagagaag aaggtgacac   7860
tgctgttgct accccctaca ctgcagcagt cctagaatat agagtctcaa tccatgattc   7920
agaagacgcc aaattcaatg atattaacat ggccaacggt aacggttaca ccgtttttga   7980
cgcacaacat ccatacaaag ctaatgttgc tgttaaaagg gaacttcaca ccccagaaag   8040
tgacaggtca tgtatacatt tggaatttga tatcgctggt agtggtttga cttacgaaac   8100
aggtgaccat gtcggagtac tttgcgataa tttgtcagaa actgttgatg aagctttgag   8160
gttattggat atgtcaccag atacttactt ctcattgcat gcagaaaaag aagacggaac   8220
tccaatatca agctcgcttc cccctccatt ccctccctgt aacttaagaa cagccctaac   8280
tagatatgct tgtttactgt cttctccaaa gaaaagtgct ttggttgcat tggcagccca   8340
cgcatccgat cctaccgaag ctgagagatt aaagcatttg gcttcaccag ccggtaaaga   8400
tgaatacagt aagtgggtag tggagagcca aagatcgctt ttagaagtga tggctgagtt   8460
tccaagtgct aaacctcctc tgggtgtatt tttcgctggt gtggccccaa gattgcagcc   8520
tagattttat tccatatcct catctccaaa aattgccgaa accagaattc acgtgacatg   8580
tgctctggtc tacgaaaaga tgccaacagg taggattcac aagggtgtct gttctacctg   8640
gatgaaaaat gctgtaccct atgaaaaatc cgaaaattgt tctagtgcac caattttcgt   8700
aagacaatct aatttcaagt taccaagcga ttctaaagta cccattatta tgatcggtcc   8760
aggtactggt ttggccccat tcagaggctt cttgcaagaa agattggctt tagtggagag   8820
tggagttgaa ttgggtcctt cagttttatt ctttggttgt agaaacagaa gaatggactt   8880
tatctacgaa gaagaattgc agagatttgt tgaaagtggt gcattggccg aattgagtgt   8940
tgcattcagc agggaaggtc caaccaaaga atacgttcaa cacaagatga tggacaaggc   9000
ttctgatatc tggaatatga tttcccaagg tgcttatttg tatgtttgtg gtgacgctaa   9060
aggaatggct agagatgttc atagatcact gcatacaatc gcacaagaac aaggtagcat   9120
ggattcaaca aaagcagagg gctttgtaaa gaatcttcag acaagcggta gatatctgag   9180
agatgtatgg taaggtaccg cggctagcta agatccgctc taaccgaaaa ggaaggagtt   9240
agacaacctg aagtctaggt ccctatttat ttttttatag ttatgttagt attaagaacg   9300
ttatttatat ttcaaatttt tctttttttt ctgtacagac gcgtgtacgc atgtaacatt   9360
atactgaaaa ccttgcttga gaaggttttg ggacgctcga agatccagct gcattaatga   9420
atcggccaac gcgcggggag aggcggtttg cgtattgggc gctcttccgc ttcctcgctc   9480
actgactcgc tgcgctcggt cgttcggctg cggcgagcgg tatcagctca ctcaaaggcg   9540
gtaatacggt tatccacaga atcaggggat aacgcaggaa agaacatgtg agcaaaaggc   9600
cagcaaaagg ccaggaaccg taaaaaggcc gcgttgctgg cgtttttcca taggctccgc   9660
cccccctgacg agcatcacaa aaatcgacgc tcaagtcaga ggtggcgaaa cccgacagga   9720
ctataaagat accaggcgtt tccccctgga agctccctcg tgcgctctcc tgttccgacc   9780
ctgccgctta ccggatacct gtccgccttt ctcccttcgg gaagcgtggc gctttctcat   9840
agctcacgct gtaggtatct cagttcggtg taggtcgttc gctccaagct gggctgtgtg   9900
```

```
cacgaacccc ccgttcagcc cgaccgctgc gccttatccg gtaactatcg tcttgagtcc   9960
aacccggtaa gacacgactt atcgccactg gcagcagcca ctggtaacag gattagcaga  10020
gcgaggtatg taggcggtgc tacagagttc ttgaagtggt ggcctaacta cggctacact  10080
agaaggacag tatttggtat ctgcgctctg ctgaagccag ttaccttcgg aaaaagagtt  10140
ggtagctctt gatccggcaa acaaaccacc gctggtagcg gtggtttttt tgtttgcaag  10200
cagcagatta cgcgcagaaa aaaaggatct caagaagatc ctttgatctt ttctacgggg  10260
tctgacgctc agtggaacga aaactcacgt taagggattt tggtcatgag attatcaaaa  10320
aggatcttca cctagatcct tttaaattaa aaatgaagtt ttaaatcaat ctaaagtata  10380
tatgagtaaa cttggtctga cagttaccaa tgcttaatca gtgaggcacc tatctcagcg  10440
atctgtctat ttcgttcatc catagttgcc tgactccccg tcgtgtagat aactacgata  10500
cgggagggct taccatctgg ccccagtgct gcaatgatac cgcgagaccc acgctcaccg  10560
gctccagatt tatcagcaat aaaccagcca gccggaaggg ccgagcgcag aagtggtcct  10620
gcaactttat ccgcctccat ccagtctatt aattgttgcc gggaagctag agtaagtagt  10680
tcgccagtta atagtttgcg caacgttgtt gccattgcta caggcatcgt ggtgtcacgc  10740
tcgtcgtttg gtatggcttc attcagctcc ggttcccaac gatcaaggcg agttacatga  10800
tcccccatgt tgtgcaaaaa agcggttagc tccttcggtc ctccgatcgt tgtcagaagt  10860
aagttggccg cagtgttatc actcatggtt atggcagcac tgcataattc tcttactgtc  10920
atgccatccg taagatgctt ttctgtgact ggtgagtact caaccaagtc attctgagaa  10980
tagtgtatgc ggcgaccgag ttgctcttgc ccggcgtcaa tacgggataa taccgcgcca  11040
catagcagaa ctttaaaagt gctcatcatt ggaaaacgtt cttcggggcg aaaactctca  11100
aggatcttac cgctgttgag atccagttcg atgtaaccca ctcgtgcacc caactgatct  11160
tcagcatctt ttactttcac cagcgtttct gggtgagcaa aaacaggaag gcaaaatgcc  11220
gcaaaaaagg gaataagggc gacacggaaa tgttgaatac tcatactctt cctttttcaa  11280
tattattgaa gcatttatca gggttattgt ctcatgagcg gatacatatt tgaatgtatt  11340
tagaaaaata aacaaatagg ggttccgcgc acatttcccc gaaaagtgcc acctgaacga  11400
agcatctgtg cttcattttg tagaacaaaa atgcaacgcg agagcgctaa tttttcaaac  11460
aaagaatctg agctgcattt ttacagaaca gaaatgcaac gcgaaagcgc tattttacca  11520
acgaagaatc tgtgcttcat ttttgtaaaa caaaaatgca acgcgagagc gctaattttt  11580
caaacaaaga atctgagctg catttttaca gaacagaaat gcaacgcgag agcgctattt  11640
taccaacaaa gaatctatac ttcttttttg ttctacaaaa atgcatcccg agagcgctat  11700
ttttctaaca aagcatctta gattactttt tttctccttt gtgcgctcta taatgcagtc  11760
tcttgataac tttttgcact gtaggtccgt taaggttaga agaaggctac tttggtgtct  11820
attttctctt ccataaaaaa agcctgactc cacttcccgc gtttactgat tactagcgaa  11880
gctgcgggtg cattttttca agataaaggc atccccgatt atattctata ccgatgtgga  11940
ttgcgcatac tttgtgaaca gaaagtgata gcgttgatga ttcttcattg gtcagaaaat  12000
tatgaacggt ttcttctatt ttgtctctat atactacgta taggaaatgt ttacattttc  12060
gtattgtttt cgattcactc tatgaatagt tcttactaca attttttttgt ctaaagagta  12120
atactagaga taaacataaa aaatgtagag gtcgagttta gatgcaagtt caaggagcga  12180
aaggtggatg ggtaggttat atagggatat agcacagaga tatatagcaa agagatactt  12240
ttgagcaatg tttgtggaag cggtattcgc aatattttag tagctcgtta cagtccggtg  12300
```

```
cgtttttggt tttttgaaag tgcgtcttca gagcgctttt ggttttcaaa agcgctctga  12360

agttcctata ctttctagag aataggaact tcggaatagg aacttcaaag cgtttccgaa  12420

aacgagcgct tccgaaaatg caacgcgagc tgcgcacata cagctcactg ttcacgtcgc  12480

acctatatct gcgtgttgcc tgtatatata tatacatgag aagaacggca tagtgcgtgt  12540

ttatgcttaa atgcgtactt atatgcgtct atttatgtag gatgaaaggt agtctagtac  12600

ctcctgtgat attatcccat tccatgcggg gtatcgtatg cttccttcag cactaccctt  12660

tagctgttct atatgctgcc actcctcaat tggattagtc tcatccttca atgctatcat  12720

ttcctttgat attggatcat actaagaaac cattattatc atgacattaa cctataaaaa  12780

taggcgtatc acgaggccct ttcgtc                                      12806
```

```
<210> SEQ ID NO 68
<211> LENGTH: 18
<212> TYPE: DNA
<213> ORGANISM: Artificial Sequence
<220> FEATURE:
<223> OTHER INFORMATION: Synthetic primer

<400> SEQUENCE: 68

tgaaataccg cacagatg                                                   18


<210> SEQ ID NO 69
<211> LENGTH: 18
<212> TYPE: DNA
<213> ORGANISM: Artificial Sequence
<220> FEATURE:
<223> OTHER INFORMATION: Synthetic primer

<400> SEQUENCE: 69

ctctcagtac aatctgct                                                   18


<210> SEQ ID NO 70
<211> LENGTH: 38
<212> TYPE: DNA
<213> ORGANISM: Artificial Sequence
<220> FEATURE:
<223> OTHER INFORMATION: Synthetic primer

<400> SEQUENCE: 70

agcagattgt actgagagga gcttggtgag cgctagga                             38


<210> SEQ ID NO 71
<211> LENGTH: 40
<212> TYPE: DNA
<213> ORGANISM: Artificial Sequence
<220> FEATURE:
<223> OTHER INFORMATION: Synthetic primer

<400> SEQUENCE: 71

catctgtgcg gtatttcacg gtattttctc cttacgcatc                           40


<210> SEQ ID NO 72
<211> LENGTH: 12824
<212> TYPE: DNA
<213> ORGANISM: Artificial Sequence
<220> FEATURE:
<223> OTHER INFORMATION: Synthetic vector construct

<400> SEQUENCE: 72

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120
```

```
ttggcgggtg tcggggctgg cttaactatg gagcttggtg agcgctagga gtcactgcca    180
ggtatcgttt gaacacggca ttagtcaggg aagtcataac acagtccttt cccgcaattt    240
tctttttcta ttactcttgg cctcctctag tacactctat attttttat gcctcggtaa     300
tgattttcat ttttttttt cccctagcgg atgactcttt ttttttctta gcgattggca     360
ttatcacata atgaattata cattatataa agtaatgtga tttcttcgaa gaatatacta    420
aaaaatgagc aggcaagata aacgaaggca aagatgacag agcagaaagc cctagtaaag    480
cgtattacaa atgaaaccaa gattcagatt gcgatctctt taaagggtgg tcccctagcg    540
atagagcact cgatcttccc agaaaaagag gcagaagcag tagcagaaca ggccacacaa    600
tcgcaagtga ttaacgtcca cacaggtata gggtttctgg accatatgat acatgctctg    660
gccaagcatt ccggctggtc gctaatcgtt gagtgcattg gtgacttaca catagacgac    720
catcacacca ctgaagactg cgggattgct ctcggtcaag cttttaaaga ggccctaggg    780
gccgtgcgtg gagtaaaaag gtttggatca ggatttgcgc ctttggatga ggcactttcc    840
agagcggtgg tagatctttc gaacaggccg tacgcagttg tcgaacttgg tttgcaaagg    900
gagaaagtag gagatctctc ttgcgagatg atcccgcatt ttcttgaaag ctttgcagag    960
gctagcagaa ttaccctcca cgttgattgt ctgcgaggca agaatgatca tcaccgtagt   1020
gagagtgcgt tcaaggctct tgcggttgcc ataagagaag ccacctcgcc caatggtacc   1080
aacgatgttc cctccaccaa aggtgttctt atgtagtgac accgattatt taaagctgca   1140
gcatacgata tatatacatg tgtatatatg tatacctatg aatgtcagta agtatgtata   1200
cgaacagtat gatactgaag atgacaaggt aatgcatcat tctatacgtg tcattctgaa   1260
cgaggcgcgc tttccttttt tctttttgct ttttcttttt ttttctcttg aactcgacgg   1320
atctatgcgg tgtgaaatac cgcacagatg cgtaaggaga aaataccgaa attgtaaacg   1380
ttaatatttt gttaaaattc gcgttaaatt tttgttaaat cagctcattt tttaaccaat   1440
aggccgaaat cggcaaaatc ccttataaat caaaagaata gaccgagata gggttgagtg   1500
ttgttccagt ttggaacaag agtccactat taaagaacgt ggactccaac gtcaaagggc   1560
gaaaaaccgt ctatcagggc gatggcccac tacgtgaacc atcaccctaa tcaagttttt   1620
tggggtcgag gtgccgtaaa gcactaaatc ggaaccctaa agggagcccc cgatttagag   1680
cttgacgggg aaagccggcg aacgtggcga gaaaggaagg gaagaaagcg aaaggagcgg   1740
gcgctagggc gctggcaagt gtagcggtca cgctgcgcgt aaccaccaca cccgccgcgc   1800
ttaatgcgcc gctacagggc gcgtccattc gccattcagg ctgcgcaact gttgggaagg   1860
gcgatcggtg cgggcctctt cgctattacg ccagctgaat tggagcgacc tcatgctata   1920
cctgagaaag caacctgacc tacaggaaag agttactcaa gaataagaat tttcgtttta   1980
aaacctaaga gtcactttaa aatttgtata cacttatttt ttttataact tatttaataa   2040
taaaaatcat aaatcataag aaattcgctt atttagaagt gtcaacaacg tatctaccaa   2100
cgatttgacc cttttccatc ttttcgtaaa tttctggcaa ggtagacaag ccgacaacct   2160
tgattggaga cttgaccaaa cctctggcga agaattgtta attaagagct cagatcttta   2220
gcagattgga ataggtgcac cattccactc tttcaagcaa tccataagtg gatctatcaa   2280
ctttccctcg cacatagctg tgaatacctt gtcaaattct tcacctgggc taacgacttt   2340
ttcaccagtt agtaatttgg ttcccaactc ttctctaacg aatctgtaca aagggtacga   2400
cctacactct ttgattctat ttggtatagg ggcagtacca tttccgtatg cggctctagc   2460
agcttcgact tcctttggta aaactgcctt cagttcttct tcaaaggcac ctatcttttg   2520
```

```
gaatattgaa gtaacggcat ttttctcagt ttcaccattg gataaagcgt gatctacaat   2580
aacttgtctc aatctctgca tcaatggata agtagcgcta catggatcgt caacgtaagt   2640
aaatacttgt tctctatcta caacttttaa taaatctttt tcacagaatc ttgatgggtg   2700
caattcacca ttgatacctg tagttagaac ctttttttgca acctgtgata cggtattttt   2760
cactgtctgt ctcaaattct cttccaagtg tctcaaatct acggcctggc atatacccac   2820
taaaaatgtt gtggacatta atttaaggat atcaacggcc tcgcttgttt ttcttgatga   2880
aatcaggccc aaagaattaa catcctgatt gtgttgttcg gctgattgta catgagaggt   2940
tactgggttg gctagatatt gcagctctga acaatagctt gccattgcta tctcagcacc   3000
tttgaaacca taatcaagac tagggttaga agatgcggtc agattcgaag gcaaaccgtt   3060
attgtagaag tcattgacca attcagaaaa ttgggcaaac attaatttgc caattgcggc   3120
tatggcaagc ctggtattat ccatactgac tcctatgggt gtaccctgga aattgcctcc   3180
atgtattgcc ttattcctcg acacatcaat aagtggatta tcgttaacag agttgatctc   3240
tctttctata gactttgtag cttgtctaat tacttcaatt tgagggccaa gccattgtgg   3300
ggatgtcctt aaagcatatc tatcttgttt gggtttttgc aaagggtcca tttcatgaac   3360
cttctgggct aacttcatgt agctagagcc gtccaaaatg tgctccatga tagctgctgc   3420
ttcaatttgt cctgggtgat gttttaacct gtgggtcaag tgatcagtaa actcaggttt   3480
tccactcatg acttcggcaa aaattgcgga caaaacttcg gccaaaactg cttgtacgtt   3540
agcttcaaac aacaccatgg atgccatacc gctgccgaca gcggtgccat tcaccagggc   3600
taaaccttcc ttgggttgca aatcaaagaa accagttgaa ataccagctt tctcaaatgc   3660
ttccttagcg gttaaggatt ctccgtctgg accagtggcc tttgaattag gtcttcccgt   3720
taataagcct gcgatatatg aaaggggaac caaatcaccg ctggcagtta ttgttcctct   3780
taagggcaac gaaggagaaa tgttgtggtt caatagtgaa gtgatggcct caagaatttc   3840
aaaccttatt ccagagtaac cttgcaacaa agtgttcacc ctaacaagca tagcagctct   3900
tgttgccgat tggggtaatg tatggcaagt ttcctttgta ttaccgaaaa taccggcgtt   3960
aaggaatctg atcagttctg tttgcaaagc agtgccattt ttagttcttc tatgagaggt   4020
agcaccaaag cctgtggtaa cgccatagga atctgtgccc ttgttcatac tttccatgac   4080
ccaatctgat gaagccttaa ctccggctct acttgtttct gcaagttcta ccttcactga   4140
accgccaacg gtcgaaatag cagctacctg tcctatcgtc aatgtctcgc cgcctagatt   4200
tacgactggt cttctgtatt cctcaaccat cttcttaact tcatccagat ggctaccttt   4260
catctggtca gctgccagac cccaattcaa aggatctgca agagtttttg tcgttacggc   4320
caccttggtc ttttcaccac caccgcatag cattgcttca atttggtcca ttttgtatct   4380
agaatccgtc gaaactaagt tctggtgttt taaaactaaa aaaaagacta actataaaag   4440
tagaatttaa gaagtttaag aaatagattt acagaattac aatcaatacc taccgtcttt   4500
atatacttat tagtcaagta ggggaataat ttcagggaac tggtttcaac cttttttttc   4560
agctttttcc aaatcagaga gagcagaagg taatagaagg tgtaagaaaa tgagatagat   4620
acatgcgtgg gtcaattgcc ttgtgtcatc atttactcca ggcaggttgc atcactccat   4680
tgaggttgtg cccgtttttt gcctgtttgt gcccctgttc tctgtagttg cgctaagaga   4740
atggacctat gaactgatgg ttggtgaaga aaacaatatt ttggtgctgg gattcttttt   4800
ttttctggat gccagcttaa aaagcgggct ccattatatt tagtggatgc caggaataaa   4860
ctgttcaccc agacacctac gatgttatat attctgtgta acccgccccc tattttgggc   4920
```

```
atgtacgggt tacagcagaa ttaaaaggct aattttttga ctaaataaag ttaggaaaat   4980
cactactatt aattatttac gtattctttg aaatggcgag tattgataat gataaactga   5040
gctcggaaga gcgcccaata cgcaaaccgc ctctccccgc gcgttggccg attcattaat   5100
gcagctggca cgacaggttt cccgactgga aagcgggcag tgagcgcaac gcaattaatg   5160
tgagttacct cactcattag gcaccccagg ctttacactt tatgcttccg gctcctatgt   5220
tgtgtggaat tgtgagcgga taacaatttc acacaggaaa cagctatgac catgattacg   5280
ccaagcgcgc aattaaccct cactaaaggg aacaaaagct ggagctcata gcttcaaaat   5340
gtttctactc ctttttact cttccagatt ttctcggact ccgcgcatcg ccgtaccact   5400
tcaaaacacc caagcacagc atactaaatt tcccctcttt cttcctctag ggtgtcgtta   5460
attacccgta ctaaaggttt ggaaaagaaa aaagagaccg cctcgtttct ttttcttcgt   5520
cgaaaaaggc aataaaaatt tttatcacgt ttctttttct tgaaaatttt ttttttgatt   5580
tttttctctt tcgatgacct cccattgata tttaagttaa taaacggtct tcaatttctc   5640
aagtttcagt ttcatttttc ttgttctatt acaacttttt ttacttcttg ctcattagaa   5700
agaaagcata gcaatctaat ctaagttttc tagatacaaa atggatttgt tattgctgga   5760
aaagtcactt attgctgtat ttgtggcagt tattctagcc acggttattt ctaaattaag   5820
aggtaagaaa ctaaaactac ctcctggtcc catccccata ccaatttttg gtaattggtt   5880
gcaagtgggc gatgatttga atcacagaaa tttggtagac tatgctaaga agttcggtga   5940
ccttttcttg cttagaatgg gtcaaaggaa tttggtagtg gttagctcac ctgatttgac   6000
taaggaggtc ttattaacgc aaggcgttga gtttggctcc agaactagaa atgttgtgtt   6060
tgatattttc actggtaaag gtcaagatat ggtttttaca gtttacggtg agcactggag   6120
aaaaatgaga agaatcatga ccgtaccatt ctttactaac aaggttgttc aacaaaatag   6180
agaaggttgg gagtttgagg cagcttccgt agtggaagac gtaaagaaaa atccagattc   6240
ggccacaaag ggtatagtac taagaaaaag actacaattg atgatgtaca acaatatgtt   6300
cagaattatg tttgacagaa gatttgaaag tgaagatgac cctttgttcc tgagacttaa   6360
ggctttgaat ggtgaaagat cgagattggc tcaaagtttc gaatataatt acggtgactt   6420
tattccaatc ttaagaccat ttttgagagg ctatttgaaa atttgccaag acgtcaagga   6480
taggaggatc gctcttttca agaagtactt tgtggacgag agaaagcaaa tagcttcttc   6540
caagcccaca ggttcggaag gtttaaaatg tgcaattgat catattttag aagctgaaca   6600
aaaaggtgaa attaacgaag ataatgtttt gtacattgta gaaaatatca atgtggctgc   6660
aatagaaaca accttatggt caatagaatg ggtattgct gaattggtga atcacccaga   6720
aatacaatct aaactgagaa acgagctaga taccgtttta ggtccaggtg tccaagttac   6780
agaacctgat ttgcataagt taccctactt gcaagctgtg gttaaagaaa ccttgagatt   6840
gagaatggct attcctcttc tagttcctca tatgaaccta catgatgcta aactggccgg   6900
ttatgatatt ccagcagaaa gtaagatttt agtaaatgca tggtggttgg ccaacaatcc   6960
aaacagttgg aaaaagcctg aagaattcag acctgaaaga ttcttcgaag aggaatctca   7020
tgttgaagcc aacggaaatg acttcagata tgtacctttt ggcgttggca gaagatcgtg   7080
tccaggaata atactagcct taccaatatt gggtatcaca attggtagga tggttcaaaa   7140
ttttgagttg ctaccaccac ccggacaatc gaaagtcgat acttcagaga aaggaggaca   7200
attctcattg catattttga atcattccat tatagtcatg aaacccagaa attgtccatc   7260
tactccatct actccatcta ctccatctac taggaggagc ggttcgggca attcaaagag   7320
```

```
ggttgaacca ctaaagccat tagttatcaa acctagagaa gaggaaattg acgatggaag   7380
gaagaaagtc actatattct tcggcaccca aacaggtaca gctgaaggtt ttgctaaggc   7440
tctaggagaa gaagcaaaag ctagatatga aaagacgaga ttcaaaattg tcgatctgga   7500
tgactatgcc gccgatgatg acgaatacga agaaaaattg aagaaagaag atgtcgcatt   7560
tttcttcctt gccacctacg gcgacggtga accaacagat aatgccgcaa ggttttacaa   7620
gtggtttact gaaggtaatg acagaggaga atggctgaag aatttgaaat atggtgtgtt   7680
cggccttggt aacagacagt acgagcattt taataaggtc gctaaggttg tagatgatat   7740
acttgttgaa caaggtgctc aaaggttagt gcaggtgggc ttgggtgacg atgatcaatg   7800
tattgaagat gactttactg cttggagaga agccttgtgg cctgaattag atactatcct   7860
tagagaagaa ggtgacactg ctgttgctac cccctacact gcagcagtcc tagaatatag   7920
agtctcaatc catgattcag aagacgccaa attcaatgat attaacatgg ccaacggtaa   7980
cggttacacc gtttttgacg cacaacatcc atacaaagct aatgttgctg ttaaaaggga   8040
acttcacacc ccagaaagtg acaggtcatg tatacatttg gaatttgata tcgctggtag   8100
tggtttgact tacgaaacag gtgaccatgt cggagtactt tgcgataatt tgtcagaaac   8160
tgttgatgaa gctttgaggt tattggatat gtcaccagat acttacttct cattgcatgc   8220
agaaaaagaa gacggaactc caatatcaag ctcgcttccc cctccattcc ctccctgtaa   8280
cttaagaaca gccctaacta gatatgcttg tttactgtct tctccaaaga aaagtgcttt   8340
ggttgcattg gcagcccacg catccgatcc taccgaagct gagagattaa agcatttggc   8400
ttcaccagcc ggtaaagatg aatacagtaa gtgggtagtg gagagccaaa gatcgctttt   8460
agaagtgatg gctgagtttc caagtgctaa acctcctctg ggtgtatttt tcgctggtgt   8520
ggccccaaga ttgcagccta gattttattc catatcctca tctccaaaaa ttgccgaaac   8580
cagaattcac gtgacatgtg ctctggtcta cgaaaagatg ccaacaggta ggattcacaa   8640
gggtgtctgt tctacctgga tgaaaaatgc tgtaccctat gaaaaatccg aaaattgttc   8700
tagtgcacca attttcgtaa gacaatctaa tttcaagtta ccaagcgatt ctaaagtacc   8760
cattattatg atcggtccag gtactggttt ggccccattc agaggcttct tgcaagaaag   8820
attggcttta gtggagagtg gagttgaatt gggtccttca gttttattct ttggttgtag   8880
aaacagaaga atggacttta tctacgaaga agaattgcag agatttgttg aaagtggtgc   8940
attggccgaa ttgagtgttg cattcagcag ggaaggtcca accaaagaat acgttcaaca   9000
caagatgatg gacaaggctt ctgatatctg gaatatgatt tcccaaggtg cttatttgta   9060
tgtttgtggt gacgctaaag gaatggctag agatgttcat agatcactgc atacaatcgc   9120
acaagaacaa ggtagcatgg attcaacaaa agcagagggc tttgtaaaga atcttcagac   9180
aagcggtaga tatctgagag atgtatggta aggtaccgcg gctagctaag atccgctcta   9240
accgaaaagg aaggagttag acaacctgaa gtctaggtcc ctatttattt ttttatagtt   9300
atgttagtat taagaacgtt atttatattt caaatttttc ttttttttct gtacagacgc   9360
gtgtacgcat gtaacattat actgaaaacc ttgcttgaga aggttttggg acgctcgaag   9420
atccagctgc attaatgaat cggccaacgc gcggggagag gcggtttgcg tattgggcgc   9480
tcttccgctt cctcgctcac tgactcgctg cgctcggtcg ttcggctgcg gcgagcggta   9540
tcagctcact caaaggcggt aatacggtta tccacagaat caggggataa cgcaggaaag   9600
aacatgtgag caaaaggcca gcaaaaggcc aggaaccgta aaaaggccgc gttgctggcg   9660
tttttccata ggctccgccc ccctgacgag catcacaaaa atcgacgctc aagtcagagg   9720
```

```
tggcgaaacc cgacaggact ataaagatac caggcgtttc cccctggaag ctccctcgtg    9780
cgctctcctg ttccgaccct gccgcttacc ggatacctgt ccgcctttct cccttcggga    9840
agcgtggcgc tttctcatag ctcacgctgt aggtatctca gttcggtgta ggtcgttcgc    9900
tccaagctgg gctgtgtgca cgaacccccc gttcagcccg accgctgcgc cttatccggt    9960
aactatcgtc ttgagtccaa cccggtaaga cacgacttat cgccactggc agcagccact   10020
ggtaacagga ttagcagagc gaggtatgta ggcggtgcta cagagttctt gaagtggtgg   10080
cctaactacg gctacactag aaggacagta tttggtatct gcgctctgct gaagccagtt   10140
accttcggaa aaagagttgg tagctcttga tccggcaaac aaaccaccgc tggtagcggt   10200
ggtttttttg tttgcaagca gcagattacg cgcagaaaaa aaggatctca agaagatcct   10260
ttgatctttt ctacggggtc tgacgctcag tggaacgaaa actcacgtta agggattttg   10320
gtcatgagat tatcaaaaag gatcttcacc tagatccttt taaattaaaa atgaagtttt   10380
aaatcaatct aaagtatata tgagtaaact tggtctgaca gttaccaatg cttaatcagt   10440
gaggcaccta tctcagcgat ctgtctattt cgttcatcca tagttgcctg actccccgtc   10500
gtgtagataa ctacgatacg ggagggctta ccatctggcc ccagtgctgc aatgataccg   10560
cgagacccac gctcaccggc tccagattta tcagcaataa accagccagc cggaagggcc   10620
gagcgcagaa gtggtcctgc aactttatcc gcctccatcc agtctattaa ttgttgccgg   10680
gaagctagag taagtagttc gccagttaat agtttgcgca acgttgttgc cattgctaca   10740
ggcatcgtgg tgtcacgctc gtcgtttggt atggcttcat tcagctccgg ttcccaacga   10800
tcaaggcgag ttacatgatc ccccatgttg tgcaaaaaag cggttagctc cttcggtcct   10860
ccgatcgttg tcagaagtaa gttggccgca gtgttatcac tcatggttat ggcagcactg   10920
cataattctc ttactgtcat gccatccgta agatgctttt ctgtgactgg tgagtactca   10980
accaagtcat tctgagaata gtgtatgcgg cgaccgagtt gctcttgccc ggcgtcaata   11040
cgggataata ccgcgccaca tagcagaact ttaaaagtgc tcatcattgg aaaacgttct   11100
tcggggcgaa aactctcaag gatcttaccg ctgttgagat ccagttcgat gtaacccact   11160
cgtgcaccca actgatcttc agcatctttt actttcacca gcgtttctgg gtgagcaaaa   11220
acaggaaggc aaaatgccgc aaaaaaggga ataagggcga cacggaaatg ttgaatactc   11280
atactcttcc tttttcaata ttattgaagc atttatcagg gttattgtct catgagcgga   11340
tacatatttg aatgtattta gaaaaataaa caaatagggg ttccgcgcac atttccccga   11400
aaagtgccac ctgaacgaag catctgtgct tcattttgta gaacaaaaat gcaacgcgag   11460
agcgctaatt tttcaaacaa agaatctgag ctgcattttt acagaacaga aatgcaacgc   11520
gaaagcgcta ttttaccaac gaagaatctg tgcttcattt ttgtaaaaca aaaatgcaac   11580
gcgagagcgc taatttttca aacaaagaat ctgagctgca tttttacaga acagaaatgc   11640
aacgcgagag cgctatttta ccaacaaaga atctatactt cttttttgtt ctacaaaaat   11700
gcatcccgag agcgctattt ttctaacaaa gcatcttaga ttactttttt tctcctttgt   11760
gcgctctata atgcagtctc ttgataactt tttgcactgt aggtccgtta aggttagaag   11820
aaggctactt tggtgtctat tttctcttcc ataaaaaaag cctgactcca cttcccgcgt   11880
ttactgatta ctagcgaagc tgcgggtgca ttttttcaag ataaaggcat ccccgattat   11940
attctatacc gatgtggatt gcgcatactt tgtgaacaga aagtgatagc gttgatgatt   12000
cttcattggt cagaaaatta tgaacggttt cttctatttt gtctctatat actacgtata   12060
ggaaatgttt acattttcgt attgttttcg attcactcta tgaatagttc ttactacaat   12120
```

```
tttttgtct aaagagtaat actagagata aacataaaaa atgtagaggt cgagtttaga  12180

tgcaagttca aggagcgaaa ggtggatggg taggttatat agggatatag cacagagata  12240

tatagcaaag agatactttt gagcaatgtt tgtggaagcg gtattcgcaa tattttagta  12300

gctcgttaca gtccggtgcg tttttggttt tttgaaagtg cgtcttcaga gcgcttttgg  12360

ttttcaaaag cgctctgaag ttcctatact ttctagagaa taggaacttc ggaataggaa  12420

cttcaaagcg tttccgaaaa cgagcgcttc cgaaaatgca acgcgagctg cgcacataca  12480

gctcactgtt cacgtcgcac ctatatctgc gtgttgcctg tatatatata tacatgagaa  12540

gaacggcata gtgcgtgttt atgcttaaat gcgtacttat atgcgtctat ttatgtagga  12600

tgaaaggtag tctagtacct cctgtgatat tatcccattc catgcggggt atcgtatgct  12660

tccttcagca ctaccottta gctgttctat atgctgccac tcctcaattg gattagtctc  12720

atccttcaat gctatcattt cctttgatat tggatcatac taagaaacca ttattatcat  12780

gacattaacc tataaaaata ggcgtatcac gaggcccttt cgtc                  12824
```

<210> SEQ ID NO 73
<211> LENGTH: 1596
<212> TYPE: DNA
<213> ORGANISM: Rhodobacter capsulatus

<400> SEQUENCE: 73

```
atgaccctgc agtcacagac ggccaaggac tgcctcgcgc tggacggggc gctgacactt    60

gtccaatgcg aggccatcgc gacacatcgc agccggattt cggtgacccc cgcgctgcgc   120

gagcgctgcg cgcgggccca tgcccggctt gagcacgcca tcgccgagca gcgccacatt   180

tacggcatca ccaccggctt cggcccgctg gcgaaccgtc tgatcggggc cgatcagggg   240

gcggagctgc agcagaacct gatctatcat ctggccaccg gcgtcgggcc gaaactgagc   300

tgggccgagg cgcgggcgtt gatgctggcg cggctcaact cgatcctgca aggcgcgtcg   360

gggcctcgc cggagacgat cgaccggatc gttgcggtgc tcaatgcggg gtttgccccc   420

gaggttccgg cgcagggaac ggtgggcgcc tcgggcgatc tgacccgct tgcgcatatg   480

gtgctggcgc tgcagggacg gggcggatg atcgacccct cgggccgcgt gcaggaggcc   540

ggggcggtga tggatcggct ctgcggcggt ccgctgacgc tggcggcccg tgacgggctg   600

gcgctggtga atggcacctc ggcgatgacc gcgattgcgg ccctgaccgg ggtcgaggcg   660

gcgcgggcga tcgacgccgc gcttcggcac agcgcggtcc tgatggaggt cttgtccggt   720

catgccgaag cctggcatcc ggctttcgca gagctgcgcc cgcatccggg gcagctgcgg   780

gcgaccgagc ggctggcgca ggcgctggat ggggcgggc gggtctgtcg gaccctgacc   840

gcggcgcggc ggctgaccgc cgcggatctg cggcccgaag atcatccggc gcaggatgcc   900

tacagtctgc gcgtggtgcc gcaactggtc ggcgcggtct gggacacgct ggactggcac   960

gatcgtgtcg tcacctgcga gctcaattcc gtcaccgaca atccgatctt tcccgagggc  1020

tgcgcggtgc ccgccctgca cggcggcaat ttcatgggcg tgcatgtcgc ccttgcctcc  1080

gatgcgctga acgcggcgct ggtgacgctg gcgggcctgg tcgagcgtca gatcgcccgg  1140

ctgaccgacg aaaagctgaa caagggcctg cccgccttcc tgcacggggg gcaggcgggg  1200

ctgcaatcgg gcttcatggg ggcgcaggtc acggcgacgg cgcttctggc ggaaatgcgg  1260

gcgaatgcca cgccggtttc ggtgcagtcg ctgtcgacca atggcgccaa tcaggatgtg  1320

gtctcgatgg gaacgattgc cgcgcggagg gcgcgggcgc agctgctgcc cctgtcgcag  1380

atccaggcga tcctggcgct tgcccttgcc caggcgatgg atctgcttga cgaccccgag  1440
```

```
gggcaggccg gatggtcgct tacggcgcgg gatctgcggg accggatccg ggcggtctcg   1500

cccgggcttc gcgccgacag accgcttgcc gggcatatcg aagcggtggc acagggtctg   1560

cgtcatccct ccgccgccgc cgatcccccg gcatga                             1596


<210> SEQ ID NO 74
<211> LENGTH: 531
<212> TYPE: PRT
<213> ORGANISM: Rhodobacter capsulatus

<400> SEQUENCE: 74

Met Thr Leu Gln Ser Gln Thr Ala Lys Asp Cys Leu Ala Leu Asp Gly
1               5                   10                  15

Ala Leu Thr Leu Val Gln Cys Glu Ala Ile Ala Thr His Arg Ser Arg
            20                  25                  30

Ile Ser Val Thr Pro Ala Leu Arg Glu Arg Cys Ala Arg Ala His Ala
        35                  40                  45

Arg Leu Glu His Ala Ile Ala Glu Gln Arg His Ile Tyr Gly Ile Thr
    50                  55                  60

Thr Gly Phe Gly Pro Leu Ala Asn Arg Leu Ile Gly Ala Asp Gln Gly
65                  70                  75                  80

Ala Glu Leu Gln Gln Asn Leu Ile Tyr His Leu Ala Thr Gly Val Gly
                85                  90                  95

Pro Lys Leu Ser Trp Ala Glu Ala Arg Ala Leu Met Leu Ala Arg Leu
            100                 105                 110

Asn Ser Ile Leu Gln Gly Ala Ser Gly Ala Ser Pro Glu Thr Ile Asp
        115                 120                 125

Arg Ile Val Ala Val Leu Asn Ala Gly Phe Ala Pro Glu Val Pro Ala
    130                 135                 140

Gln Gly Thr Val Gly Ala Ser Gly Asp Leu Thr Pro Leu Ala His Met
145                 150                 155                 160

Val Leu Ala Leu Gln Gly Arg Gly Arg Met Ile Asp Pro Ser Gly Arg
                165                 170                 175

Val Gln Glu Ala Gly Ala Val Met Asp Arg Leu Cys Gly Gly Pro Leu
            180                 185                 190

Thr Leu Ala Ala Arg Asp Gly Leu Ala Leu Val Asn Gly Thr Ser Ala
        195                 200                 205

Met Thr Ala Ile Ala Ala Leu Thr Gly Val Glu Ala Ala Arg Ala Ile
    210                 215                 220

Asp Ala Ala Leu Arg His Ser Ala Val Leu Met Glu Val Leu Ser Gly
225                 230                 235                 240

His Ala Glu Ala Trp His Pro Ala Phe Ala Glu Leu Arg Pro His Pro
                245                 250                 255

Gly Gln Leu Arg Ala Thr Glu Arg Leu Ala Gln Ala Leu Asp Gly Ala
            260                 265                 270

Gly Arg Val Cys Arg Thr Leu Thr Ala Ala Arg Arg Leu Thr Ala Ala
        275                 280                 285

Asp Leu Arg Pro Glu Asp His Pro Ala Gln Asp Ala Tyr Ser Leu Arg
    290                 295                 300

Val Val Pro Gln Leu Val Gly Ala Val Trp Asp Thr Leu Asp Trp His
305                 310                 315                 320

Asp Arg Val Val Thr Cys Glu Leu Asn Ser Val Thr Asp Asn Pro Ile
                325                 330                 335

Phe Pro Glu Gly Cys Ala Val Pro Ala Leu His Gly Gly Asn Phe Met
            340                 345                 350
```

```
Gly Val His Val Ala Leu Ala Ser Asp Ala Leu Asn Ala Ala Leu Val
        355                 360                 365

Thr Leu Ala Gly Leu Val Glu Arg Gln Ile Ala Arg Leu Thr Asp Glu
    370                 375                 380

Lys Leu Asn Lys Gly Leu Pro Ala Phe Leu His Gly Gly Gln Ala Gly
385                 390                 395                 400

Leu Gln Ser Gly Phe Met Gly Ala Gln Val Thr Ala Thr Ala Leu Leu
                405                 410                 415

Ala Glu Met Arg Ala Asn Ala Thr Pro Val Ser Val Gln Ser Leu Ser
            420                 425                 430

Thr Asn Gly Ala Asn Gln Asp Val Val Ser Met Gly Thr Ile Ala Ala
        435                 440                 445

Arg Arg Ala Arg Ala Gln Leu Leu Pro Leu Ser Gln Ile Gln Ala Ile
    450                 455                 460

Leu Ala Leu Ala Leu Ala Gln Ala Met Asp Leu Leu Asp Asp Pro Glu
465                 470                 475                 480

Gly Gln Ala Gly Trp Ser Leu Thr Ala Arg Asp Leu Arg Asp Arg Ile
                485                 490                 495

Arg Ala Val Ser Pro Gly Leu Arg Ala Asp Arg Pro Leu Ala Gly His
            500                 505                 510

Ile Glu Ala Val Ala Gln Gly Leu Arg His Pro Ser Ala Ala Ala Asp
        515                 520                 525

Pro Pro Ala
    530
```

<210> SEQ ID NO 75
<211> LENGTH: 1596
<212> TYPE: DNA
<213> ORGANISM: Artificial Sequence
<220> FEATURE:
<223> OTHER INFORMATION: Synthetic R.capsulatus gene, codon optimised for S.cerevisiae

<400> SEQUENCE: 75

```
atgaccctgc aatctcaaac agctaaagat tgtttggctt tggatggtgc cttgacatta     60

gttcaatgcg aagcgatagc aacccataga agtagaatct ctgtaacacc agccctacgt    120

gagagatgtg ctagagcaca tgctaggtta gaacatgcaa tagccgaaca gcgacacata    180

tatgggataa cgacaggctt cgggccactt gctaacaggc tgatcggagc agaccagggt    240

gctgaattac aacagaacct tatctaccat ttggcaaccg gagttggccc caaattatca    300

tgggccgaag ccagagcttt aatgctcgct cgtttgaata gtatactaca aggtgcttct    360

ggtgctagcc ctgaaacaat tgataggatc gttgcagtct taaatgccgg atttgccccg    420

gaagtcccag cccaaggaac cgttggtgct tcgggtgact taactccgtt agcacacatg    480

gtattagcat tgcaaggcag aggtcgtatg attgatcctt cagggagagt tcaagaagcc    540

ggcgctgtca tggataggtt gtgtggaggc cctttaacat tggctgccag agatggcctc    600

gccttagtaa atggtacatc tgccatgaca gctattgccg cattgaccgg tgtggaggct    660

gcaagagcga ttgatgcagc gcttagacat tccgcagtct tgatggaggt cctgtcaggg    720

catgctgagg cttggcaccc tgcctttgcg gaattgcgtc cgcatccagg acaattacgc    780

gccactgaga ggttagctca agcattggac ggcgcaggta gagtctgccg gactcttaca    840

gccgctaggc gtctaactgc agctgatctg agaccagaag atcatccagc tcaagatgca    900

tattcacttc gagtagttcc tcagctggtt ggtgccgtat gggatacgtt ggattggcac    960

gacagggttg tgacttgcga acttaactcc gtgaccgaca atccaatttt ccccgagggt   1020
```

```
tgtgcggttc cagcactaca cggtggaaac tttatgggcg tacatgtggc actagcttct   1080

gacgctttaa atgcagcgtt ggttacatta gctggtctag ttgaaaggca gattgcaaga   1140

cttactgatg agaagttgaa taagggtttg cctgcttttt tgcatggagg ccaagcaggt   1200

ttacaatcag gtttcatggg agctcaggtt actgctactg ctttgctagc ggaaatgaga   1260

gctaacgcga ctcccgtgtc cgttcaaagc ctcagcacca atggtgcaaa tcaagacgtg   1320

gtaagtatgg gtacgattgc cgcgagacga gcaagagctc aacttttacc tctgtctcaa   1380

atccaagcga ttttggcact ggctcttgca caagccatgg atctcctaga cgatcctgaa   1440

ggacaagccg gttggtcctt aacggcaaga gatttaagag accgtatacg ggctgtcagt   1500

ccagggttgc gcgcagatag accactagcg ggtcatattg aagctgtggc tcaaggtcta   1560

agacacccct cggcagctgc cgatccacct gcttaa                             1596
```

<210> SEQ ID NO 76
<211> LENGTH: 40
<212> TYPE: DNA
<213> ORGANISM: Rhodobacter capsulatus

<400> SEQUENCE: 76

```
ccgctcgagc ggatgaccct gcaatctcaa acagctaaag                          40
```

<210> SEQ ID NO 77
<211> LENGTH: 30
<212> TYPE: DNA
<213> ORGANISM: Rhodobacter capsulatus

<400> SEQUENCE: 77

```
gcggatcctt aagcaggtgg atcggcagct                                      30
```

<210> SEQ ID NO 78
<211> LENGTH: 35
<212> TYPE: DNA
<213> ORGANISM: Arabidopsis thaliana

<400> SEQUENCE: 78

```
tgccatggca atggcgccac aagaacaagc agttt                                35
```

<210> SEQ ID NO 79
<211> LENGTH: 36
<212> TYPE: DNA
<213> ORGANISM: Arabidopsis thaliana

<400> SEQUENCE: 79

```
gcggatcccc ttcacaatcc atttgctagt tttgcc                               36
```

<210> SEQ ID NO 80
<211> LENGTH: 42
<212> TYPE: DNA
<213> ORGANISM: Arabidopsis thaliana

<400> SEQUENCE: 80

```
gacaagcttg cggccagatc tcgatcccgc gaaattaata cg                        42
```

<210> SEQ ID NO 81
<211> LENGTH: 40
<212> TYPE: DNA
<213> ORGANISM: Arabidopsis thaliana

<400> SEQUENCE: 81

```
tgctcgagtg cggcctcaca atccatttgc tagttttgcc                           40
```

```
<210> SEQ ID NO 82
<211> LENGTH: 34
<212> TYPE: DNA
<213> ORGANISM: Vitis vinifera

<400> SEQUENCE: 82

cgccatatga tggcatccgt agaggagttc agaa                              34


<210> SEQ ID NO 83
<211> LENGTH: 35
<212> TYPE: DNA
<213> ORGANISM: Vitis vinifera

<400> SEQUENCE: 83

ccggatcctc attagttagt gacagttgga acaga                             35


<210> SEQ ID NO 84
<211> LENGTH: 42
<212> TYPE: DNA
<213> ORGANISM: Artificial Sequence
<220> FEATURE:
<223> OTHER INFORMATION: Synthetic primer

<400> SEQUENCE: 84

aaggagatat acatatgatg gcatccgtag aggagttcag aa                     42


<210> SEQ ID NO 85
<211> LENGTH: 45
<212> TYPE: DNA
<213> ORGANISM: Artificial Sequence
<220> FEATURE:
<223> OTHER INFORMATION: Synthetic primer

<400> SEQUENCE: 85

ctttaccaga ctcgagtcat tagttagtga cagttggaac agagt                  45
```